(12) United States Patent
Tsunoda et al.

(10) Patent No.: US 7,136,605 B2
(45) Date of Patent: Nov. 14, 2006

(54) IMAGE FORMING APPARATUS, METHOD OF EVALUATING NOISE, AND METHODS OF MANUFACTURING AND MODIFYING IMAGE FORMING APPARATUS

(75) Inventors: Koichi Tsunoda, Tokyo (JP); Motohisa Hirono, Tokyo (JP)

(73) Assignee: Ricoh Company, Ltd., Tokyo (KP)

( * ) Notice: Subject to any disclaimer, the term of this patent is extended or adjusted under 35 U.S.C. 154(b) by 160 days.

(21) Appl. No.: 10/744,044

(22) Filed: Dec. 24, 2003

(65) Prior Publication Data
US 2004/0190928 A1    Sep. 30, 2004

(30) Foreign Application Priority Data
Dec. 24, 2002   (JP)   ............... 2002-372301
Dec. 26, 2002   (JP)   ............... 2002-377256

(51) Int. Cl.
*G03G 21/20* (2006.01)
(52) U.S. Cl. ...................................... 399/91
(58) Field of Classification Search ............ 399/1, 399/91, 9, 11, 18; 381/71.1, 71.2, 71.3
See application file for complete search history.

(56) References Cited

U.S. PATENT DOCUMENTS

| | | | |
|---|---|---|---|
| 6,466,752 B1 * | 10/2002 | Tsunoda | ............... 399/91 |
| 6,697,584 B1 | 2/2004 | Tsunoda et al. | |
| 6,876,828 B1 * | 4/2005 | Tsunoda et al. | ............... 399/91 |

FOREIGN PATENT DOCUMENTS

| | | |
|---|---|---|
| JP | 9-193506 | 7/1997 |
| JP | 10-232163 | 9/1998 |
| JP | 10-253440 | 9/1998 |
| JP | 10-253442 | 9/1998 |
| JP | 10-267742 | 10/1998 |
| JP | 10-267743 | 10/1998 |
| JP | 2001-336975 | 12/2001 |
| JP | 2002-128316 | 5/2002 |
| JP | 2002-196634 | * 7/2002 |
| JP | 2002-351272 | * 12/2002 |

OTHER PUBLICATIONS

M. Ohashi, et al., The Seventh Design & Systems Conference, Sound, Vibration and Design, and Color and Design, vol. 1, No. 089B, pp. 269-272, "Binaural Sound Measurement System for Psychoacoustic Parameters", Nov. 10-11, 1997 (with English translation).

* cited by examiner

*Primary Examiner*—Hoan Tran
(74) *Attorney, Agent, or Firm*—Oblon, Spivak, McClelland, Maier & Neustadt, P.C.

(57) ABSTRACT

A method of manufacturing an image forming apparatus includes evaluating, based on a pair comparison method, sounds generated when forming an image, carrying out a multiple linear regression analysis using a difference between scores of the evaluation as a target variable and a difference between psycho-acoustic parameter values as an explanatory variable, deriving formula concerning the difference in scores of sound quality from a result of the analysis, substituting an average of the psycho-acoustic parameter values used to derive the formula into the formula, defining discomfort of the sound when all the parameter values are average values as zero, and deriving a sound quality evaluation formula, and designing each unit of the apparatus based on the sound quality evaluation formula.

156 Claims, 46 Drawing Sheets

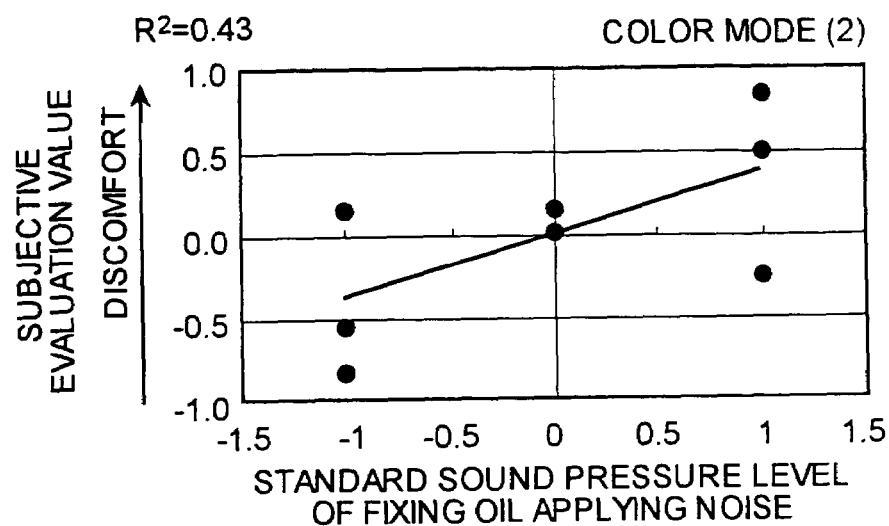
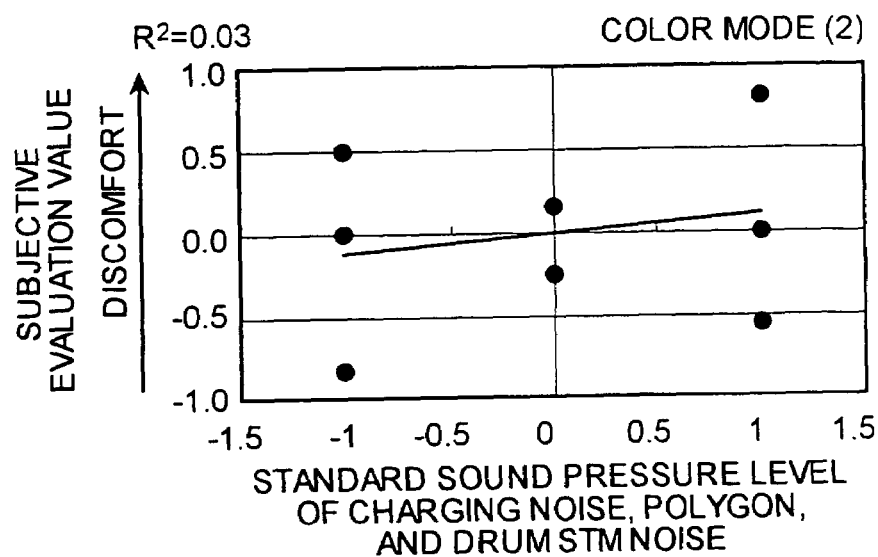

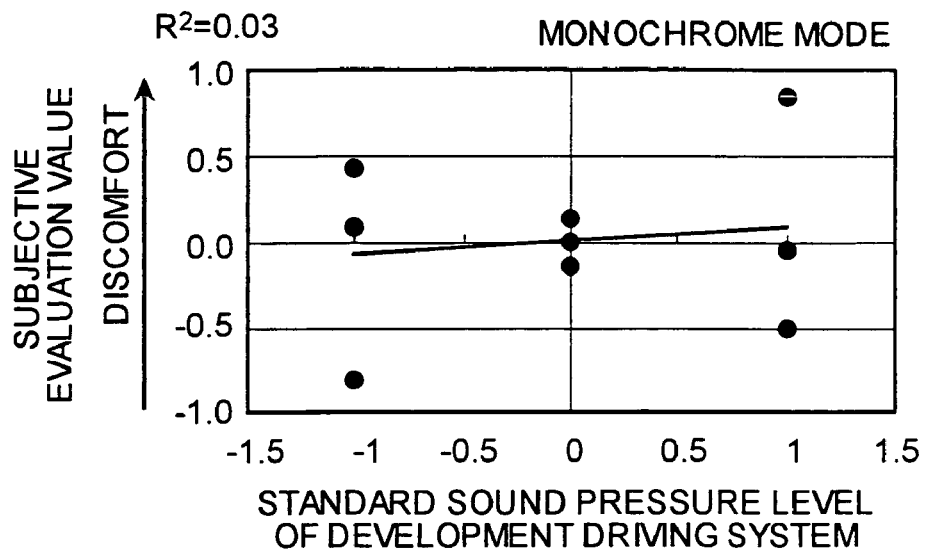
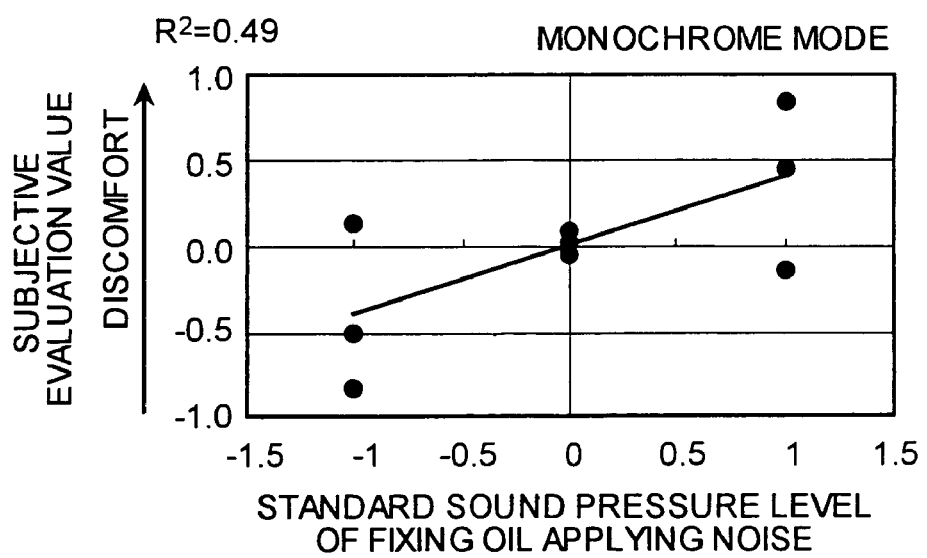

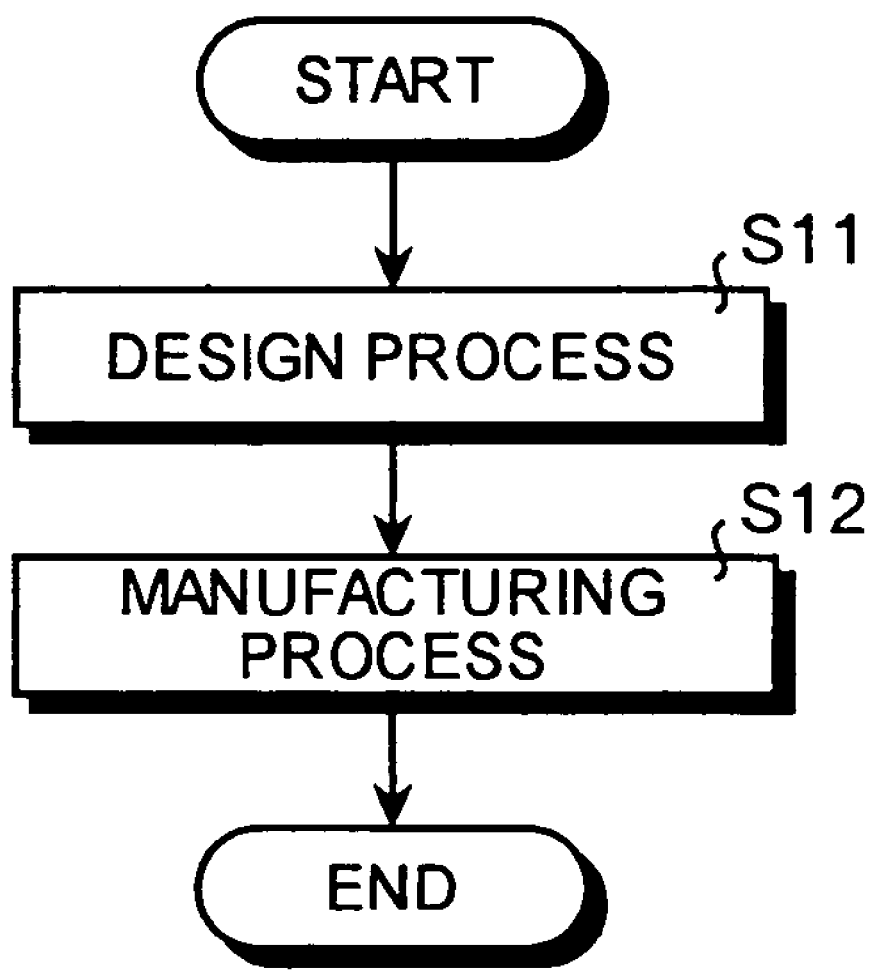

IMAGE FORMING APPARATUS, METHOD OF EVALUATING NOISE, AND METHODS OF MANUFACTURING AND MODIFYING IMAGE FORMING APPARATUS

CROSS-REFERENCE TO RELATED APPLICATIONS

The present document incorporates by reference the entire contents of Japanese priority documents, 2002-372301 filed in Japan on Dec. 24, 2002 and 2002-377256 filed in Japan on Dec. 26, 2002.

BACKGROUND OF THE INVENTION

1) Field of the Invention

The present invention relates to a technology to reduce operation noise of an image forming apparatus.

2) Description of the Related Art

Various kinds of apparatuses that are equipped with an image forming apparatus such as a copying machine, a printer, and a facsimile are installed in a place like an office. The image forming apparatus has a considerable amount of parts mechanically connected to each other. The image forming apparatus also has motors that drive motorized mechanisms. When operated, each part of the image forming apparatus generates operation noise that gives a discomfort to users.

A method of using a sound power level or a sound pressure level as a standard is currently used as a method of evaluating noise generated from the office machines, such as the International Organization for Standard (ISO) 7779. However, according to the method of evaluating noise based on the sound power level or the sound pressure level, a correlation between the evaluation and a subjective discomfort of a human may be low. Therefore, even if the evaluation based on the standard is satisfactory, a person may feel discomfort in many cases.

For example, even when two sounds have the same sound pressure, if a person hears the two sounds having different frequency distributions or different percussive noises may have different discomfort levels from each of the two sounds. In other words, even if the sound pressure level is low, sounds that include a high-frequency component or a pure tone component are apt to be felt unpleasant.

Therefore, it is considered to be necessary to take a measure against the noise of the office machines by evaluating the sound quality and taking the evaluation into account, instead of simply using the sound power level or the sound pressure level as a standard.

Japanese Patent Application Laid-open No. H9-193506 discloses a technique of providing an image forming apparatus with a masking sound generation function to mask the operation noise that is generated during the formation of an image, and decreasing the noise by generating a masking sound during the image forming process.

Japanese Patent Application Laid-open No. H10-232163 discloses a technique of evaluating only rasping as low-frequency random noise that is generated in the airflow such as exhaust sound from among various kinds of sound generated from the image forming apparatus.

Japanese Patent Application Laid-open No. H10-253440 discloses a technique of evaluating only a sound that is generated from a scanner motor or a charger.

Japanese Patent Application Laid-open No. H10-253442 discloses a technique of evaluating only a sound that is generated when a sheet of paper is rubbed as high-frequency random noise.

Japanese Patent Application Laid-open No. H10-267742 discloses a technique of evaluating only a beating sound of a pure tone having a peak in a plurality of close frequencies attributable to the beating of a driving mechanism.

Japanese Patent Application Laid-open No. H10-267743 discloses a technique of evaluating smoothness of sound that includes a pure tone, beating, a low-frequency component, and a high-frequency component that the human feels.

Japanese Patent Application Laid-open No. 2001-336975 discloses a technique of evaluating the sound quality that takes an influence of noise generated from the office machines to a subjective feeling of the human into consideration.

Japanese Patent Application Laid-open No. 2002-128316 discloses an image forming apparatus that has a paper feeding mechanism which obtains a discomfort index based on a loudness and a sharpness obtained from the sound generated from the image forming apparatus, and which makes the obtained discomfort index satisfy a predetermined condition.

However, the image forming apparatus mounted with the masking sound generation function generates the masking sound in addition to sound that the apparatus generates during the operation. Therefore, this has a risk of further increasing the noise level. It is also necessary to install a masking generation unit (such as a speaker, a controller, and a sound source) that has nothing to do with the image forming operation. Accordingly, an installation room is necessary, which prevents implementing a small apparatus, and increases cost. Consequently, this method cannot be an effective countermeasure against the noise.

The above sound quality evaluation techniques enable an evaluation of specific sound quality of the operation noise from the image forming apparatus, by taking into a human's subjective feeling into consideration. However, these techniques do not make clear a detailed method of countermeasures against noise by utilizing a result of the evaluation.

In order to evaluate sound quality and take a countermeasure against the noise based on the result of the evaluation, it is necessary to quantitatively measure the sound quality and measure the improvement in the sound quality after taking the countermeasure in comparison with the sound quality before taking the countermeasure.

However, because the sound quality is not a physical quantity, it is not possible to carry out a quantitative measurement. Therefore, it is difficult to set target variables of improvement. A person evaluates the sound quality as "improved" or "slightly improved". Since the evaluation levels are different between persons, it is also difficult to determine whether an obtained result is a general evaluation.

Psycho-acoustic parameters are known as physical quantities to evaluate sound quality. The following representative psycho-acoustic parameters are known.

(For example, "targeting for an innovative step of design and system toward the twenty-first century", The Japan Society of Mechanical Engineers, The seventh design engineering system lecture, "sound, vibration and design, and color and design (1)", 089B, Nov. 10–11, 1997.)

(1) Loudness (sone): a volume of a hearing (2) Sharpness (acum): a relative distribution of a high-frequency component (3) Tonality (tu): a relative distribution of pure tone component (4) Roughness (asper): a feeling of roughness of sound
(5) Fluctuation strings (vacil): variation strength, a feeling of beating
(6) Impulsiveness (iu): impactness
(7) Relative approach: a feeling of variation When the values of these parameters increase, the discomfort levels tend to increase.

Since the apparatuses like the copying machine and the printer have a complex structure, these apparatuses generate a sound that includes various kinds of tones. In other words, a plurality of sound sources including a motor, a solenoid, and paper generate time varying low-frequency sound, high frequency sound, and impulsive sound. A human judges whether the sound generated from the image forming apparatus is unpleasant from the total sound. It is considered that a human makes the judgment by placing a weight of discomfort in some portion of the sound. In other words, it is considered that the above kinds of psycho-acoustic parameters do not give discomfort to every person at the same rate, but the parameters have different weights of discomfort.

One of the above conventional techniques provides a paper feeding mechanism that obtains a discomfort index based on a loudness and a sharpness, and makes the obtained discomfort index satisfy a predetermined condition (as disclosed in Japanese Patent Application Laid-open No. 2002-128316). This technique takes the above points into consideration.

Some image forming apparatuses that are available in recent years can select resolution of an image, or can handle both a color image and a monochrome image. Also, some image forming apparatuses can operate differently depending on quality of a paper onto which an image is printed, or can set a printing speed. As explained above, most image forming apparatuses in recent years have a plurality of operation modes. An apparatus that has a plurality of operation modes makes different movements in the parts of the apparatus depending on the operation mode, and the apparatus generates different noises accordingly. Particularly, when the printing speed changes, the frequency component of the sound generated is different according to a change of a motor speed. The sounds generated from each mechanism also changes, and based on the change, a sound source from which a human feels discomfort also changes.

Therefore, for the image forming apparatus that has a plurality of operation modes, it is necessary to take a countermeasure against unpleasant noises in each operation mode by carrying out a complex work to evaluate sound qualities in each operation mode that has a different printing speed. However, the above problems have not yet been solved by the conventional technologies.

SUMMARY OF THE INVENTION

It is an object of the present invention to solve at least the problems in the conventional technology.

The image forming apparatus that forms an image onto a recording medium, according to one aspect of the present invention has an index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium. The index S satisfies an inequality $$S \leq 0.5664 \text{Ln}(\text{ppm})-2.1364$$

where $14 \leq \text{ppm} \leq 38$, and ppm is an output number of the recording medium per minute with A4 size in horizontal direction, wherein the sound is collected at a listening position approximately one meter from an edge of the image forming apparatus.

The image forming apparatus that forms an image onto a recording medium, according to another aspect of the present invention has an index S calculated from an equation $$S=A\times(\text{loudness value})+B\times(\text{sharpness value})+C\times(\text{tonality value})+D\times(\text{impulsiveness value})+E$$

where $A=0.2347697$, $B=0.3847411$, $C=2.6283418$, $D=1.5681529$, and $E=-3.790295483$, using loudness, sharpness, tonality, and impulsiveness of a psycho-acoustic parameter obtained from a sound generated from the image forming apparatus when forming an image onto the recording medium. The index S satisfies an inequality $$S \leq 0.5664 \text{Ln}(\text{ppm})-2.1364$$

where $14 \leq \text{ppm} \leq 38$, and ppm is an output number of the recording medium per minute with A4 size in horizontal direction, wherein the sound is collected at a listening position approximately one meter from an edge of the image forming apparatus.

The image forming apparatus that forms an image onto a recording medium, according to still another aspect of the present invention has an index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium. The index S satisfies an inequality $$S \leq 0.532 \ln(v)-2.8381$$

where $62.5 \leq v \leq 185$, and v is a speed of forming an image onto the recording medium in millimeters per second, wherein the sound is collected at a listening position approximately one meter from an edge of the image forming apparatus.

The image forming apparatus that forms an image onto a recording medium, according to still another aspect of the present invention has an index S calculated from an equation $$S=A\times(\text{loudness value})+B\times(\text{sharpness value})+C\times(\text{tonality value})+D\times(\text{impulsiveness value})+E$$

where $A=0.2347697$, $B=0.3847411$, $C=2.6283418$, $D=1.5681529$, and $E=-3.790295483$, using loudness, sharpness, tonality, and impulsiveness of a psycho-acoustic parameter obtained from a sound generated from the image forming apparatus when forming an image onto the recording medium. The index S satisfies an inequality $$S \leq 0.532 \ln(v)-2.8381$$

where $62.5 \leq v \leq 185$, and v is a speed of forming an image onto the recording medium in millimeters per second, wherein the sound is collected at a listening position approximately one meter from an edge of the image forming apparatus.

The method of manufacturing an image forming apparatus that forms an image onto a recording medium, according to still another aspect of the present invention includes designing the image forming apparatus so that an index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln}(\text{ppm}) - 2.1364$$

where $14 \leq \text{ppm} \leq 38$, and ppm is an output number of the recording medium per minute with A4 size in horizontal direction, wherein the sound is collected at a listening position approximately one meter from an edge of the image forming apparatus to be fabricated, and manufacturing the image forming apparatus based on a result of the designing.

The method of manufacturing an image forming apparatus, according to still another aspect of the present invention includes designing the image forming apparatus so that an index S calculated from an equation $$S=A\times(\text{loudness value})+B\times(\text{sharpness value})+C\times(\text{tonality value})+D\times(\text{impulsiveness value})+E$$

where $A=0.2347697$, $B=0.3847411$, $C=2.6283418$, $D=1.5681529$, and $E=-3.790295483$, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln}(\text{ppm}) - 2.1364$$

where $14 \leq \text{ppm} \leq 38$, and ppm is an output number of the recording medium per minute with A4 size in horizontal direction, wherein the sound is collected at a listening position approximately one meter from an edge of the image forming apparatus to be fabricated, and manufacturing the image forming apparatus based on a result of the designing.

The method of manufacturing an image forming apparatus that forms an image onto a recording medium, according to still another aspect of the present invention includes designing the image forming apparatus so that an index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.532 \ln(v) - 2.8381$$

where $62.5 \leq v \leq 185$, and v is a speed of forming an image onto the recording medium in millimeters per second, wherein the sound is collected at a listening position approximately one meter from an edge of the image forming apparatus to be fabricated, and manufacturing the image forming apparatus based on a result of the designing.

The method of manufacturing an image forming apparatus that forms an image onto a recording medium, according to still another aspect of the present invention includes designing the image forming apparatus so that an index S calculated from an equation $$S=A\times(\text{loudness value})+B\times(\text{sharpness value})+C\times(\text{tonality value})+D\times(\text{impulsiveness value})+E$$

where $A=0.2347697$, $B=0.3847411$, $C=2.6283418$, $D=1.5681529$, and $E=-3.790295483$, using loudness, sharpness, tonality, and impulsiveness of a psycho-acoustic parameter obtained from a sound generated from the image forming apparatus when forming an image onto the recording medium satisfies an inequality $$S \leq 0.532 \ln(v) - 2.8381$$

where $62.5 \leq v \leq 185$, and v is a speed of forming an image onto the recording medium in millimeters per second, wherein the sound is collected at a listening position approximately one meter from an edge of the image forming apparatus to be fabricated, and manufacturing the image forming apparatus based on a result of the designing.

The method of modifying an image forming apparatus that forms an image onto a recording medium, according to still another aspect of the present invention includes modifying the image forming apparatus so that an index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln}(\text{ppm}) - 2.1364$$

where $14 \leq \text{ppm} \leq 38$, and ppm is an output number of the recording medium per minute with A4 size in horizontal direction, wherein the sound is collected at a listening position approximately one meter from an edge of the image forming apparatus to be modified.

The method of modifying an image forming apparatus that forms an image onto a recording medium, according to still another aspect of the present invention includes modifying the image forming apparatus so that an index S calculated from an equation $$S=A\times(\text{loudness value})+B\times(\text{sharpness value})+C\times(\text{tonality value})+D\times(\text{impulsiveness value})+E$$

where $A=0.2347697$, $B=0.3847411$, $C=2.6283418$, $D=1.5681529$, and $E=-3.790295483$, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln}(\text{ppm}) - 2.1364$$

where $14 \leq \text{ppm} \leq 38$, and ppm is an output number of the recording medium per minute with A4 size in horizontal direction, wherein the sound is collected at a listening position approximately one meter from an edge of the image forming apparatus to be modified.

The method of modifying an image forming apparatus that forms an image onto a recording medium, still another aspect of the present invention includes modifying the image forming apparatus so that an index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.532\ln(v)-2.8381$$

where $62.5 \leq v \leq 185$, and v is a speed of forming an image onto the recording medium in millimeters per second, wherein the sound is collected at a listening position approximately one meter from an edge of the image forming apparatus to be modified.

The method of modifying an image forming apparatus that forms an image onto a recording medium, according to still another aspect of the present invention includes modifying the image forming apparatus so that an index S calculated from an equation $$S=A\times(\text{loudness value})+B\times(\text{sharpness value})+C\times(\text{tonality value})+D\times(\text{impulsiveness value})+E$$

where $A=0.2347697$, $B=0.3847411$, $C=2.6283418$, $D=1.5681529$, and $E=-3.790295483$, using loudness, sharpness, tonality, and impulsiveness of a psycho-acoustic parameter obtained from a sound generated from the image forming apparatus when forming an image onto the recording medium satisfies an inequality $$S \leq 0.532\ln(v)-2.8381$$

where $62.5 \leq v \leq 185$, and v is a speed of forming an image onto the recording medium in millimeters per second, wherein the sound is collected at a listening position approximately one meter from an edge of the image forming apparatus to be modified.

The method of evaluating sound generated from an image forming apparatus when forming an image onto a recording medium, according to still another aspect of the present invention includes evaluating a plurality of kinds of the sound based on a pair comparison method, performing a multiple linear regression analysis using a difference between scores of the evaluation as a target variable and a difference between psycho-acoustic parameter values as an explanatory variable, deriving an equation concerning the difference between scores of sound quality from a result of the analysis, as follows $$\alpha i - \alpha j = \sum_{l=1}^{L} b_l(x_{li}-x_{lj})$$

where $\alpha n$ is subjective value with respect to discomfort of the sound where $n=1,2,\ldots i,\ldots j,\ldots, n$, $b_l$ is a regression coefficient, $x_{li}$ and $x_{lj}$ are Psycho-acoustic parameter values of two sounds to be compared where $i=1,2,3\ldots, n$ and $l=1,2,3\ldots, L$, substituting an average of the psycho-acoustic parameter values used to derive the equation, into the equation, defining the discomfort of the sound when all the parameter values are average values as zero, deriving a sound quality evaluation equation to estimate a score of the discomfort of the sound, and evaluating the sound quality using the sound quality evaluation equation derived.

The method of manufacturing an image forming apparatus that forms an image onto a recording medium, according to still another aspect of the present invention includes evaluating a plurality of kinds of the sound based on a pair comparison method, performing a multiple linear regression analysis using a difference between scores of the evaluation as a target variable and a difference between psycho-acoustic parameter values as an explanatory variable, deriving an equation concerning the difference between scores of sound quality from a result of the analysis, as follows $$\alpha i - \alpha j = \sum_{l=1}^{L} b_l(x_{li}-x_{lj})$$

where $\alpha n$ is subjective value with respect to discomfort of the sound where $n=1,2,\ldots i,\ldots j,\ldots, n$, $b_l$ is a regression coefficient, $x_{li}$ and $x_{lj}$ are Psycho-acoustic parameter values of two sounds to be compared where $i=1,2,3\ldots, n$ and $l=1,2,3\ldots, L$, substituting an average of the psycho-acoustic parameter values used to derive the equation, into the equation, defining the discomfort of the sound when all the parameter values are average values as zero, deriving a sound quality evaluation equation to estimate a score of the discomfort of the sound, evaluating the sound quality using the sound quality evaluation equation derived, designing each unit of the image forming apparatus so that a result of the evaluating satisfies a predetermined condition, and manufacturing the image forming apparatus based on a result of the designing.

The method of modifying an image forming apparatus that forms an image onto a recording medium, according to still another aspect of the present invention includes evaluating a plurality of kinds of the sound based on a pair comparison method, performing a multiple linear regression analysis using a difference between scores of the evaluation as a target variable and a difference between psycho-acoustic parameter values as an explanatory variable, deriving an equation concerning the difference between scores of sound quality from a result of the analysis, as follows $$\alpha i - \alpha j = \sum_{l=1}^{L} b_l(x_{li}-x_{lj})$$

where $\alpha n$ is subjective value with respect to discomfort of the sound where $n=1,2,\ldots i,\ldots j,\ldots, n$, $b_l$ is a regression coefficient, $x_{li}$ and $x_{lj}$ are Psycho-acoustic parameter values of two sounds to be compared where $i=1,2,3\ldots, n$ and $l=1,2,3\ldots, L$, substituting an average of the psycho-acoustic parameter values used to derive the equation, defining the discomfort of the sound when all the parameter values are average values as zero, deriving a sound quality evaluation equation to estimate a score of the discomfort of the sound, evaluating the sound quality of sound generated from the image forming apparatus to be modified using the sound quality evaluation equation derived, and modifying corresponding units of the image forming apparatus to be modified based on a result of the evaluating.

The image forming apparatus that forms an image onto a recording medium, according to still another aspect of the present invention has a probability P calculated from an equation $$P=1/(1+\exp(-z))$$

where $z=A\times(\text{loudness value})+B\times(\text{sharpness value})+C\times(\text{tonality value})+D\times(\text{impulsiveness value})+E$ where $0.76545285 \leq A \leq 0.84940259$, $1.27685159 \leq B \leq 1.48461447$, $8.11323413 \leq C \leq 9.98398583$, $0.30484579 \leq D \leq 5.87837423$, $-14.10339529 \leq E \leq -12.47284396$, and a standard deviation σ is 0.721307, using loudness, sharpness, tonality, and impulsiveness of a psycho-acoustic parameter obtained from a sound generated from the image forming apparatus when forming an image onto the recording medium satisfies an inequality $$P \leq 0.3383\text{Ln}(\text{ppm})-0.8103$$

where $14 \leq \text{ppm} \leq 38$, and ppm is an output number of the recording medium per minute with A4 size in horizontal direction, wherein the sound is collected at a listening position approximately one meter from an edge of the image forming apparatus.

The image forming apparatus that forms an image onto a recording medium, according to still another aspect of the present invention has a probability P calculated from an equation $$P=1/(1+\exp(-z\pm 2\sigma))$$

where $z=A\times(\text{loudness value})+B\times(\text{sharpness value})+C\times(\text{tonality value})+D\times(\text{impulsiveness value})+E$ where A=0.80742768, B=1.38073296, C=9.04860954, D=5.59160971, and E=−13.28811895, and a standard deviation σ is 0.721307, using loudness, sharpness, tonality, and impulsiveness of a psycho-acoustic parameter obtained from a sound generated from the image forming apparatus when forming an image onto the recording medium. The probability P satisfies an inequality $$P \leq 0.3383\text{Ln}(\text{ppm})-0.8103$$

where $14 \leq \text{ppm} \leq 38$, and ppm is an output number of the recording medium per minute with A4 size in horizontal direction, wherein the sound is collected at a listening position approximately one meter from an edge of the image forming apparatus.

The image forming apparatus that forms an image onto a recording medium, according to still another aspect of the present invention has a probability P calculated from an equation $$P=1/(1+\exp(-z))$$

where $z=A\times(\text{loudness value})+B\times(\text{sharpness value})+C\times(\text{tonality value})+D\times(\text{impulsiveness value})+E$ where A=0.80742768, B=1.38073296, C=9.04860954, D=5.59160971, and E=−13.28811895, using loudness, sharpness, tonality, and impulsiveness of a psycho-acoustic parameter obtained from a sound generated from the image forming apparatus when forming an image onto the recording medium. The probability P satisfies an inequality $$P \leq 0.3383\text{Ln}(\text{ppm})-0.8103$$

where $14 \leq \text{ppm} \leq 38$, and ppm is an output number of the recording medium per minute with A4 size in horizontal direction, wherein the sound is collected at a listening position approximately one meter from an edge of the image forming apparatus.

The image forming apparatus that forms an image onto a recording medium, according to still another aspect of the present invention has a probability P calculated from an equation $$P=1/(1+\exp(-z))$$

where $z=A\times(\text{loudness value})+B\times(\text{sharpness value})+C\times(\text{tonality value})+D\times(\text{impulsiveness value})+E$ where $0.76545285 \leq A \leq 0.84940259$, $1.27685159 \leq B \leq 1.48461447$, $8.11323413 \leq C \leq 9.98398583$, $5.30484579 \leq D \leq 5.8737423$, $-14.10339529 \leq E \leq -12.17284396$, using loudness, sharpness, tonality, and impulsiveness of a psycho-acoustic parameter obtained from a sound generated from the image forming apparatus when forming an image onto the recording medium. The probability P satisfies an inequality $$P \leq 0.3201\ln(v)-1.2402$$

where $62.5 \leq v \leq 185$, and v is a speed of forming an image onto the recording medium in millimeters per second, wherein the sound is collected at a listening position approximately one meter from an edge of the image forming apparatus.

The image forming apparatus that forms an image onto a recording medium, according to still another aspect of the present invention has a probability P calculated from an equation $$P=1/(1+\exp(-z\pm 2\sigma))$$

where $z=A\times(\text{loudness value})+B\times(\text{sharpness value})+C\times(\text{tonality value})+D\times(\text{impulsiveness value})+E$ where A=0.80742768, B=1.38073296, C=9.04860954, D=5.59160971, and E=−13.28811895, and a standard deviation σ is 0.721307, using loudness, sharpness, tonality, and impulsiveness of a psycho-acoustic parameter obtained from a sound generated from the image forming apparatus when forming an image onto the recording medium. The probability P satisfies an inequality $$P \leq 0.3201\ln(v)-1.2402$$

where $62.5 \leq v \leq 185$, and v is a speed of forming an image onto the recording medium in millimeters per second, wherein the sound is collected at a listening position approximately one meter from an edge of the image forming apparatus.

The image forming apparatus that forms an image onto a recording medium, according to still another aspect of the present invention has a probability P calculated from an equation $$P=1/(1+\exp(-z))$$

where $z=A\times(\text{loudness value})+B\times(\text{sharpness value})+C\times(\text{tonality value})+D\times(\text{impulsiveness value})+E$ where A=0.80742768, B=1.38073296, C=9.04860954, D=5.59160971, and E=−13.28811895, using loudness, sharpness, tonality, and impulsiveness of a psycho-acoustic parameter obtained from a sound generated from the image forming apparatus when forming an image onto the recording medium. The probability P satisfies an inequality $$P \leq 0.3201 \mathrm{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus.

The method of manufacturing an image forming apparatus that forms an image onto a recording medium, according to still another aspect of the present invention includes designing the image forming apparatus so that a probability P calculated from an equation $$P = 1/(1 + \exp(-z))$$

where $z = A \times (\text{loudness value}) + B \times (\text{sharpness value}) + C \times (\text{tonality value}) + D \times (\text{impulsiveness value}) + E$ where $0.76545285 \leq A \leq 0.84940259$, $1.27685159 \leq B \leq 1.48461447$, $8.11323413 \leq C \leq 9.98398583$, $5.30484579 \leq D \leq 5.87837423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3383 \mathrm{Ln}(\mathrm{ppm}) - 0.8103,$$

where $14 \leq \mathrm{ppm} \leq 38$, and ppm is an output number of the recording medium per minute with A4 size in horizontal direction, wherein the sound is collected at a listening position approximately one meter from an edge of the image forming apparatus to be fabricated, and fabricating the image forming apparatus based on a result of the designing.

The method of manufacturing an image forming apparatus that forms an image onto a recording medium, according to still another aspect of the present invention includes designing the image forming apparatus so that a probability P calculated from an equation $$P = 1/(1 + \exp(-z \pm 2\sigma))$$

where $z = A \times (\text{loudness value}) + B \times (\text{sharpness value}) + C \times (\text{tonality value}) + D \times (\text{impulsiveness value}) + E$ where A=0.80742768, B=1.38073296, C=9.04860954, D=5.59160971, and E=−13.28811895, and a standard deviation σ is 0.721307, using loudness, sharpness, tonality, and impulsiveness of a psycho-acoustic parameter obtained from a sound generated from the image forming apparatus when forming an image onto the recording medium satisfies an inequality $$P \leq 0.3383 \mathrm{Ln}(\mathrm{ppm}) - 8103,$$

where $14 \leq \mathrm{ppm} \leq 38$, and ppm is an output number of the recording medium per minute with A4 size in horizontal direction, wherein the sound is collected at a listening position approximately one meter from an edge of the image forming apparatus to be fabricated, and fabricating the image forming apparatus based on a result of the designing.

The method of manufacturing an image forming apparatus that forms an image onto a recording medium, according to still another aspect of the present invention includes designing the image forming apparatus so that a probability P calculated from an equation $$P = 1/(1 + \exp(-z))$$

where $z = A \times (\text{loudness value}) + B \times (\text{sharpness value}) + C \times (\text{tonality value}) + D \times (\text{impulsiveness value}) + E$ where A=0.80742768, B=1.38073296, C=9.04860954, D=5.59160971, and E=−13.28811895, using loudness, sharpness, tonality, and impulsiveness of a psycho-acoustic parameter obtained from a sound generated from the image forming apparatus when forming an image onto the recording medium satisfies an inequality $$P \leq 0.3383 \mathrm{Ln}(\mathrm{ppm}) - 0.8103,$$

where $14 \leq \mathrm{ppm} \leq 38$, and ppm is an output number of the recording medium per minute with A4 size in horizontal direction, wherein the sound is collected at a listening position approximately one meter from an edge of the image forming apparatus to be fabricated, and fabricating the image forming apparatus based on a result of the designing.

The method of manufacturing an image forming apparatus that forms an image onto a recording medium, according to still another aspect of the present invention includes designing the image forming apparatus so that a probability P calculated from an equation $$P = 1/(1 + \exp(-z))$$

where $z = A \times (\text{loudness value}) + B \times (\text{sharpness value}) + C \times (\text{tonality value}) + D \times (\text{impulsiveness value}) + E$ where $0.76545285 \leq A \leq 0.84940259$, $1.27685159 \leq B \leq 1.48461447$, $8.11323413 \leq C \leq 9.98398583$, $5.30484579 \leq D \leq 5.87837423$, and $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3201 \mathrm{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be fabricated, and fabricating the image forming apparatus based on a result of the designing.

The method of manufacturing an image forming apparatus that forms an image onto a recording medium, according to still another aspect of the present invention includes designing the image forming apparatus so that a probability P calculated from an equation $$P = 1/(1 + \exp(-z \pm 2\sigma))$$

where $z = A \times (\text{loudness value}) + B \times (\text{sharpness value}) + C \times (\text{tonality value}) + D \times (\text{impulsiveness value}) + E$ where A=0.80742768, B=1.38073296, C=9.04860954, D=5.59160971, and E=−13.28811895, and a standard deviation σ is 0.721307, using loudness, sharpness, tonality, and impulsiveness of a psycho-acoustic parameter obtained from a sound generated from the image forming apparatus when forming an image onto the recording medium satisfies an inequality $$P \leq 0.3201 \mathrm{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be fabricated, and fabricating the image forming apparatus based on a result of the designing.

The method of manufacturing an image forming apparatus that forms an image onto a recording medium, according to still another aspect of the present invention includes designing the image forming apparatus so that a probability P calculated from an equation $$P=1/(1+\exp(-z))$$

where $z=A \times$(loudness value)$+B \times$(sharpness value)$+C \times$(tonality value)$+D \times$(impulsiveness value)$+E$ where A=0.80742768, B=1.38073296, C=9.04860954, D=5.59160971, and E=−13.28811895, using loudness, sharpness, tonality, and impulsiveness of a psycho-acoustic parameter obtained from a sound generated from the image forming apparatus when forming an image onto the recording medium satisfies an inequality $$P \leq 0.3201532 \text{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be fabricated, and fabricating the image forming apparatus based on a result of the designing.

The method of modifying an image forming apparatus that forms an image onto a recording medium, according to still another aspect of the present invention includes modifying the image forming apparatus so that a probability P calculated from an equation $$P=1/(1+\exp(-z))$$

where $z=A \times$(loudness value)$+B \times$(sharpness value)$+C \times$(tonality value)$+D \times$(impulsiveness value)$+E$ where $0.76545285 \leq A \leq 0.84940259$, $1.27685159 \leq B \leq 1.48461447$, $8.11323413 \leq C \leq 9.98398583$, $5.30484579 \leq D \leq 5.87837423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3383 \text{Ln}(\text{ppm}) - 0.8301$$

where $14 \leq \text{ppm} \leq 38$, and ppm is an output number of the recording medium per minute with A4 size in horizontal direction, wherein the sound is collected at a listening position approximately one meter from an edge of the image forming apparatus to be modified.

The method of modifying an image forming apparatus that forms an image onto a recording medium, according to still another aspect of the present invention includes modifying the image forming apparatus so that a probability P calculated from an equation $$P=1/(1+\exp(-z \pm 2\sigma))$$

where $z=A \times$(loudness value)$+B \times$(sharpness value)$+C \times$(tonality value)$+D \times$(impulsiveness value)$+E$ where A=0.80742768, B=1.38073296, C=9.04860954, D=5.59160971, and E=−13.28811895, and a standard deviation σ is 0.721307, using loudness, sharpness, tonality, and impulsiveness of a psycho-acoustic parameter obtained from a sound generated from the image forming apparatus when forming an image onto the recording medium satisfies an inequality $$P \leq 0.3383 \text{Ln}(\text{ppm}) - 0.8103,$$

where $14 \leq \text{ppm} \leq 38$, and ppm is an output number of the recording medium per minute with A4 size in horizontal direction, wherein the sound is collected at a listening position approximately one meter from an edge of the image forming apparatus to be modified.

The method of modifying an image forming apparatus that forms an image onto a recording medium, according to still another aspect of the present invention includes modifying the image forming apparatus so that a probability P calculated from an equation $$P=1/(1+\exp(-z))$$

where $z=A \times$(loudness value)$+B \times$(sharpness value)$+C \times$(tonality value)$+D \times$(impulsiveness value)$+E$ where A=0.80742768, B=1.38073296, C=9.04860954, D=5.59160971, and E=−13.28811895, using loudness, sharpness, tonality, and impulsiveness of a psycho-acoustic parameter obtained from a sound generated from the image forming apparatus when forming an image onto the recording medium satisfies an inequality $$P \leq 0.3383 \text{Ln}(\text{ppm}) - 0.8301$$

where $14 \leq \text{ppm} \leq 38$, and ppm is an output number of the recording medium per minute with A4 size in horizontal direction, wherein the sound is collected at a listening position approximately one meter from an edge of the image forming apparatus to be modified.

The method of modifying an image forming apparatus that forms an image onto a recording medium, according to still another aspect of the present invention includes modifying the image forming apparatus so that a probability P calculated from an equation $$P=1/(1+\exp(-z))$$

where $z=A \times$(loudness value)$+B \times$(sharpness value)$+C \times$(tonality value)$+D \times$(impulsiveness value)$+E$ where $0.76545285 \leq A \leq 0.84940259$, $1.27685159 \leq B \leq 1.48461447$, $8.11323413 \leq C \leq 9.98398583$, $5.30484579 \leq D \leq 5.878337423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3201 \text{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be modified.

The method of modifying an image forming apparatus that forms an image onto a recording medium, according to still another aspect of the present invention includes modifying the image forming apparatus so that a probability P calculated from an equation $$P=1/(1+\exp(-z\pm2\sigma))$$

where $z=A\times$(loudness value)$+B\times$(sharpness value)$+C\times$(tonality value)$+D\times$(impulsiveness value)$+E$ where A=0.80742768, B=1.38073296, C=9.04860954, D=5.59160971, and E=−13.28811895, and a standard deviation σ is 0.721307, using loudness, sharpness, tonality, and impulsiveness of a psycho-acoustic parameter obtained from a sound generated from the image forming apparatus when forming an image onto the recording medium satisfies an inequality $$P\leq0.3201\text{Ln}(v)-1.2402,$$

where $62.5\leq v\leq185$, and v is a speed of forming an image onto the recording medium in millimeters per second, wherein the sound is collected at a listening position approximately one meter from an edge of the image forming apparatus to be modified.

The method of modifying an image forming apparatus that forms an image onto a recording medium, according to still another aspect of the present invention includes modifying the image forming apparatus so that a probability P calculated from an equation $$P=1/(1+\exp(-z))$$

where $z=A\times$(loudness value)$+B\times$(sharpness value)$+C\times$(tonality value)$+D\times$(impulsiveness value)$+E$ where A=0.80742768, B=1.38073296, C=9.04860954, D=5.59169971, and E=−13.28811895, using loudness, sharpness, tonality, and impulsiveness of a psycho-acoustic parameter obtained from a sound generated from the image forming apparatus when forming an image onto the recording medium satisfies an inequality $$P\leq0.3201\text{Ln}(v)-1.2402,$$

where $62.5\leq v\leq185$, and v is a speed of forming an image onto the recording medium in millimeters per second, wherein the sound is collected at a listening position approximately one meter from an edge of the image forming apparatus to be modified.

The method of evaluating sound generated from an image forming apparatus when forming an image onto a recording medium, according to still another aspect of the present invention includes evaluating a plurality of kinds of the sound based on a pair comparison method, performing a logistic regression analysis using discomfort probabilities of two sounds based on the evaluating as a target variable and using a difference between psycho-acoustic parameter values as an explanatory variable, deriving an equation concerning the discomfort probability of sound quality from a result of the analysis, as follows $$\hat{P}_{ij}=1\Big/\left\{1+\exp\left[-\left(\sum_{l=1}^{L}b_1(x_{li}-x_{lj})\right)\right]\right\}$$

where $b_i$ is a regression coefficient, $x_{li}$ and $x_{lj}$ are Psycho-acoustic parameter values of two sounds to be compared where i=1,2,3 . . . , n and l=1,2,3 . . . , L, substituting an average of the psycho-acoustic parameter values used to derive the equation, into the equation, defining a probability P as 0.5, deriving a sound quality evaluation equation to estimate the discomfort probability of the sound, and evaluating the sound quality using the sound quality evaluation equation derived.

The method of manufacturing an image forming apparatus that forms an image onto a recording medium, according to still another aspect of the present invention includes evaluating a plurality of kinds of the sound based on a pair comparison method, performing a logistic regression analysis using discomfort probabilities of two sounds based on the evaluating as a target variable and using a difference between psycho-acoustic parameter values as an explanatory variable, deriving an equation concerning the discomfort probability of sound quality from a result of the analysis, as follows $$\hat{P}_{ij}=1\Big/\left\{1+\exp\left[-\left(\sum_{l=1}^{L}b_1(x_{li}-x_{lj})\right)\right]\right\}$$

where $b_i$ is a regression coefficient, $x_{li}$ and $x_{lj}$ are Psycho-acoustic parameter values of two sounds to be compared where i=1,2,3 . . . , n and l=1,2,3 . . . , L, substituting an average of the psycho-acoustic parameter values used to derive the equation, into the equation, defining a probability P as 0.5, deriving a sound quality evaluation equation to estimate the discomfort probability of the sound, evaluating the sound quality using the sound quality evaluation equation derived, designing each unit of the image forming apparatus so that a result of the evaluating satisfies a predetermined condition, and manufacturing the image forming apparatus based on a result of the designing.

The method of modifying an image forming apparatus that forms an image onto a recording medium, according to still another aspect of the present invention includes evaluating a plurality of kinds of the sound based on a pair comparison method, performing a logistic regression analysis using discomfort probabilities of two sounds based on the evaluating as a target variable and using a difference between psycho-acoustic parameter values as an explanatory variable, deriving an equation concerning the discomfort probability of sound quality from a result of the analysis, as follows $$\hat{P}_{ij}=1\Big/\left\{1+\exp\left[-\left(\sum_{l=1}^{L}b_1(x_{li}-x_{lj})\right)\right]\right\}$$

where $b_i$ is a regression coefficient, $x_{li}$ and $x_{lj}$ are Psycho-acoustic parameter values of two sounds to be compared where i=1,2,3 . . . , n and l=1,2,3 . . . , L, substituting an average of the psycho-acoustic parameter values used to derive the equation, into the equation, defining a probability P as 0.5, deriving a sound quality evaluation equation to estimate the discomfort probability of the sound, evaluating the sound quality using the sound quality evaluation equation derived, and modifying corresponding units of the image forming apparatus to be modified based on a result of the evaluating.

The other objects, features and advantages of the present invention are specifically set forth in or will become appar-

BRIEF DESCRIPTION OF THE DRAWINGS

FIG. 20 13 is a graph of a relationship between a sound pressure level of a sound of applying a fixing oil and a subjective evaluation value in color mode (2);

FIG. 21 is a graph of a relationship between a sound pressure level of charging, polygon, and drum STM noises and a subjective evaluation value in color mode (2);

FIG. 24 is a graph of a relationship between a sound pressure level of a sound of driving mechanism for development and a subjective evaluation value in monochrome mode;

FIG. 25 is a graph of a relationship between a sound pressure level of a sound of applying a fixing oil and a subjective evaluation value in monochrome mode;

FIG. 57 is another flowchart of manufacturing the image forming apparatus according to the present invention.

DETAILED DESCRIPTIONS

Exemplary embodiments of an image forming apparatus, a method of evaluating noise, and methods of manufacturing and modifying the image forming apparatus, according to the present invention are explained in detail with reference to the accompanying drawings.

Figure 1:
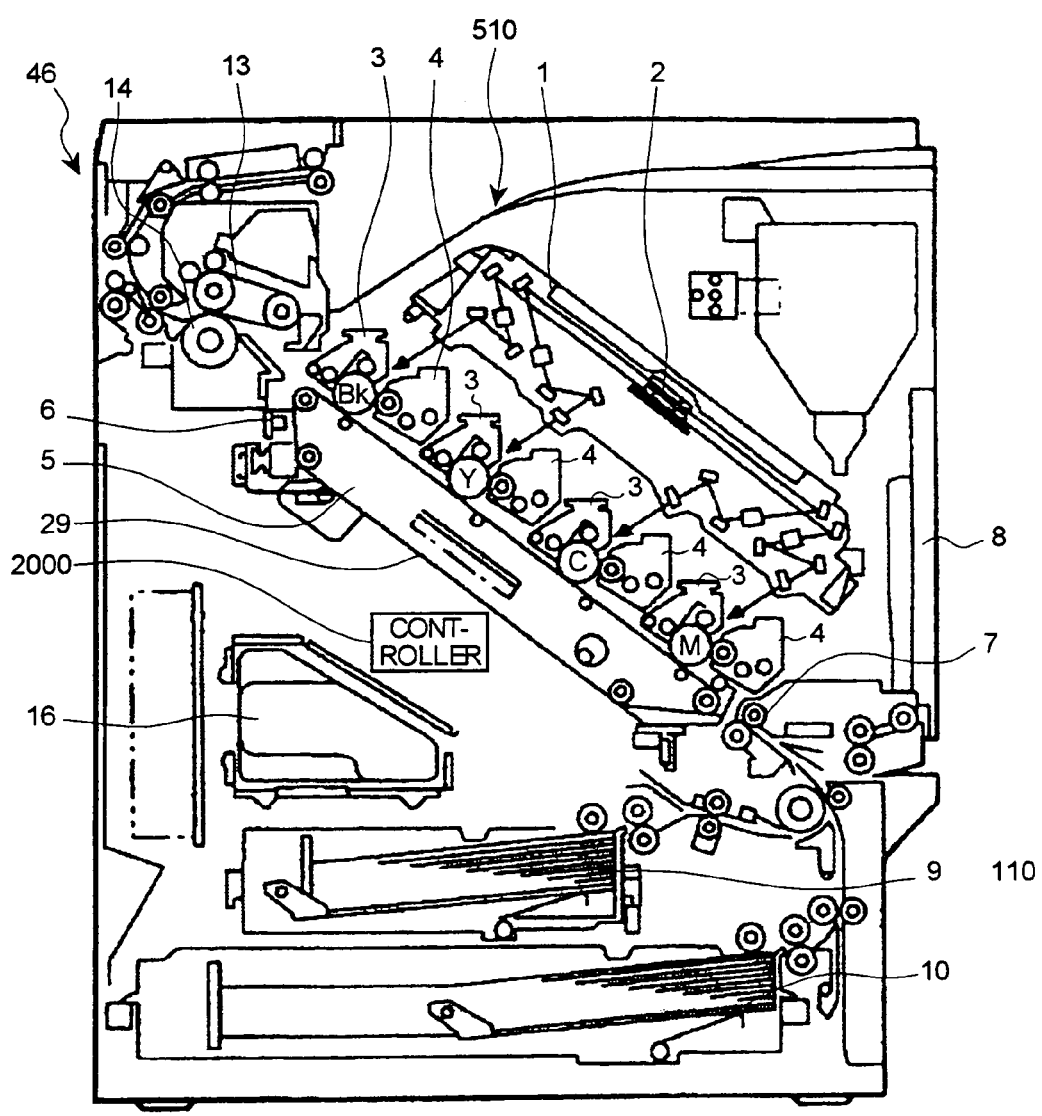
FIG. 1 is a schematic diagram of an image forming apparatus.

FIG. 1 is a schematic diagram of an image forming apparatus. According to one aspect of the present invention, there is provided a method of evaluating noise generated from an image forming apparatus distributed in general, and a modifying method of reducing discomfort that the noise gives to a person based on the evaluation. Prior to this modifying method, a configuration of the general image forming apparatus will be explained.

The image forming apparatus shown in FIG. 1 is a digital color printer employing an electro photographic system that includes an optical unit 1, photosensitive units 3, development units 4, a transfer unit 5, a fixing unit 46, and a paper feeder 110.

During an image forming, a recording medium on which an image is formed (hereinafter referred to as paper, including printing paper and an over head projector (OHP) transparency) that is accommodated in the paper feeder 110 disposed at a lowest position of the image forming apparatus is fed along a predetermined feeding route that rises from a right lower side to a left upper side in FIG. 1. The paper is supplied from the paper feeder 110, and is fed at an angle along the feeding route from the right lower side to the left upper direction above the paper feeder 110 in FIG. 1. During this period, the paper passes through between the four photosensitive units 3 and the four development units 4, and the transfer unit 5 that are disposed along the feeding route, and predetermined images are transferred onto the paper. The paper that is transferred with the images is fed to the fixing unit 46 that is disposed at a left upper side of the photosensitive units 3, the development units 4, and the transfer unit 5, and the fixing unit 46 fixes the transfer images.

Figure 2:
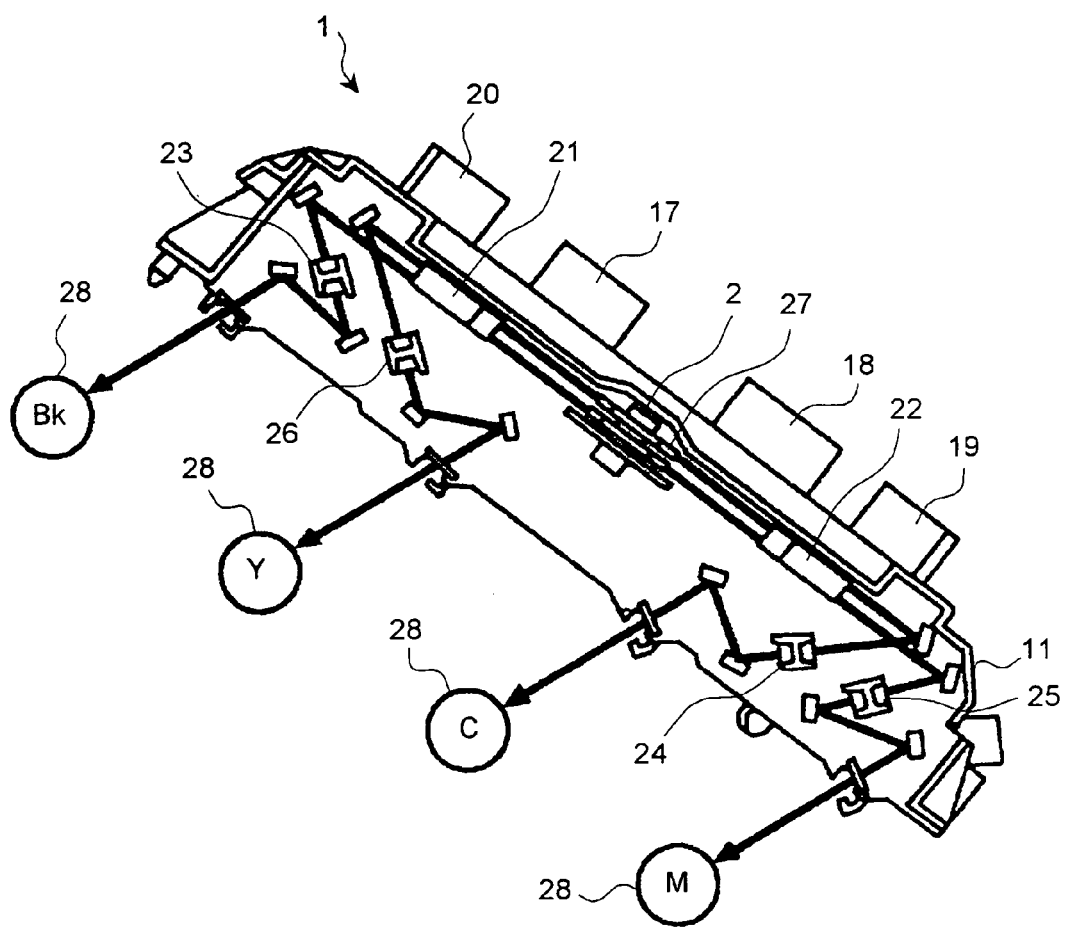
FIG. 2 is a schematic diagram of an optical unit of the image forming apparatus.

As shown in FIG. 2, the optical unit 1 extends along the paper feeding route from a right lower side to a left upper direction, and has a housing 11 that is disposed along this direction. Four laser diodes (LD) for a black (Bk) 17, a cyan (C) 18, a magenta (M) 19, and a yellow (Y) 20 are installed on the upper portion of the housing 11.

In the housing 11, there are provided a polygon mirror motor 2 to scan a main scanning line, two-layer fθ lenses 21 and 22 to correct a dot position, long WTL lenses 23, 24, 25, and 26 to correct an optical face tangle error, and a cylinder lens not shown to correct a laser beam diameter.

Two six-face mirrors 27 are integrally provided at upper and lower sides of the polygon mirror motor 2. The LDs 17, 18, 19, and 20 irradiate laser beams onto the polygon mirrors 27.

The LDs 17, 18, 19, and 20 irradiate laser beams corresponding to the respective colors to match the timing of feeding the paper. The beams as indicated by thick lines in FIG. 2 are irradiated onto photosensitive drums 28 of the corresponding colors via the cylinder lens, the polygon mirrors 27, the two-layer fθ lenses 21 and 22, and the long WTL lenses 23, 24, 25, and 26.

A two-beam system LD unit 17 is preferably applied to the black color. In other words, when the two-beam system LD is employed, two beams can be written at the same time during the formation of a monochrome image. The beams can be promptly written while suppressing the revolution speed of the polygon mirror motor 2. When the revolution speed of the polygon mirror motor 2 is suppressed, it is possible to obtain the effect of suppressing noise and the effect of extending the life of the motor. For example, in the color mode printing, when the revolution speed of the polygon mirrors 27 is 29528 revolutions per minute, the printing speed is 28 ppm. However, in the monochrome printing, the printing speed is 38 ppm although the revolution speed of the polygon mirrors 27 is as small as 21850 revolutions per minute.

Referring back to FIG. 1, configurations of the photosensitive units 3, the development units 4, and the transfer unit 5 in this image forming apparatus will be explained. The image forming apparatus employs a tandem imaging system of four continuous drums. Based on the employment of this system, the printing speeds in the full-color printing mode and the monochrome printing mode can be improved. As explained above, the installation room can be reduced when the photosensitive units 3, the development units 4, and the transfer unit 5 are laid out in an inclined direction, which makes the apparatus small in total.

The photosensitive units 3 and the development units 4 form independent units corresponding to the colors. In other words, there are the photosensitive unit 3 and the development unit 4 for magenta (M), the photosensitive unit 3 and the development unit 4 for cyan (C), the photosensitive unit 3 and the development unit 4 for yellow (Y), and the photosensitive unit 3 and the development unit 4 for black (Bk). These photosensitive units 3 and development units 4 are laid out in this order from the right lower side to the left upper side as shown in FIG. 1. The photosensitive units 3 for M, C, and Y except Bk have exactly the same configurations. Therefore, a new photosensitive unit can be used for any one of the colors M, C, and Y.

The transfer unit 5 is disposed at the lower side of the photosensitive units 3 and the development units 4 that are disposed in the inclined direction in the above order, extending along this inclined direction. The transfer unit 5 has a plurality of rollers, and an endless transfer belt 29 that is wound around the rollers. When a motor not shown rotates the rollers, the transfer belt 29 is rotated in the counterclockwise direction in FIG. 1. The paper supplied from the paper feeder 110 is mounted onto the transfer belt 29, and is fed from the right lower side to the left upper side in FIG. 1. A P sensor 6 is disposed at the downstream (i.e., a left upper side in FIG. 1) in the feeding direction of the transfer unit 5. The P sensor 6 detects the density of a P sensor pattern that is formed on the transfer belt 29. The result of the detection is utilized for the control.

Figure 3:
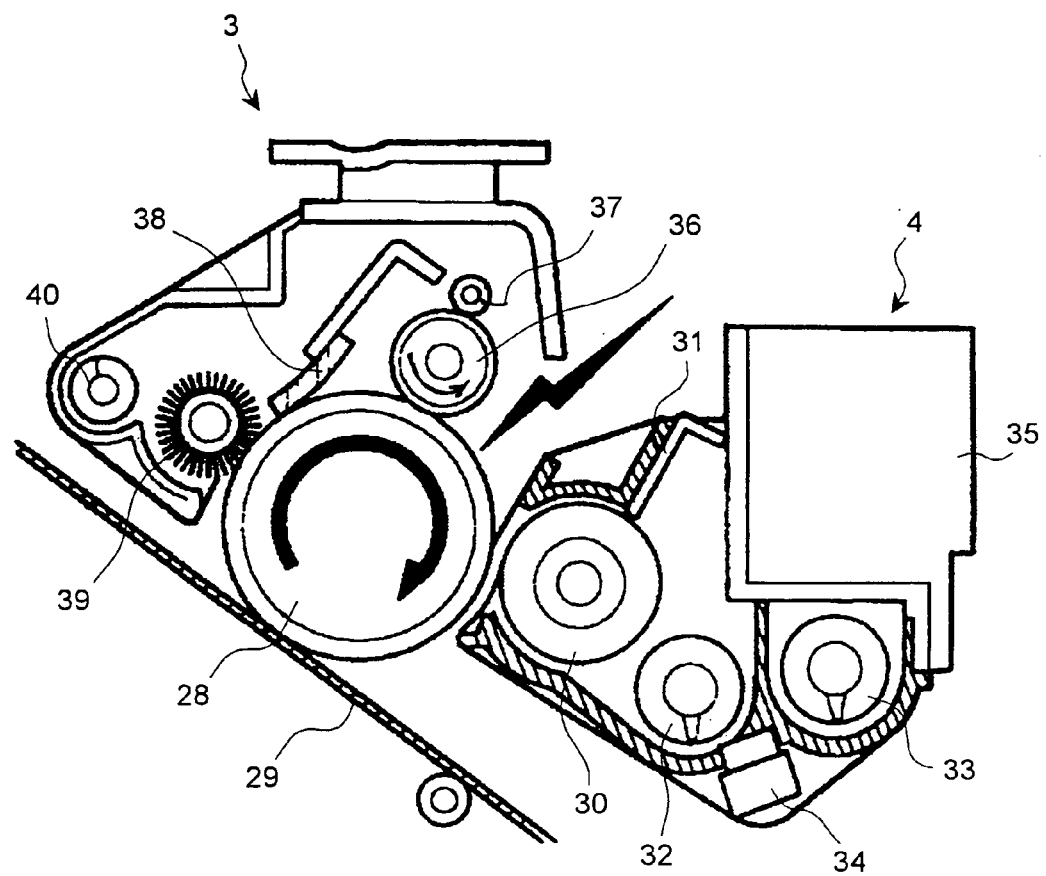
FIG. 3 is a schematic diagram of a photosensitive unit and a development unit of the image forming apparatus.
Figure 4:
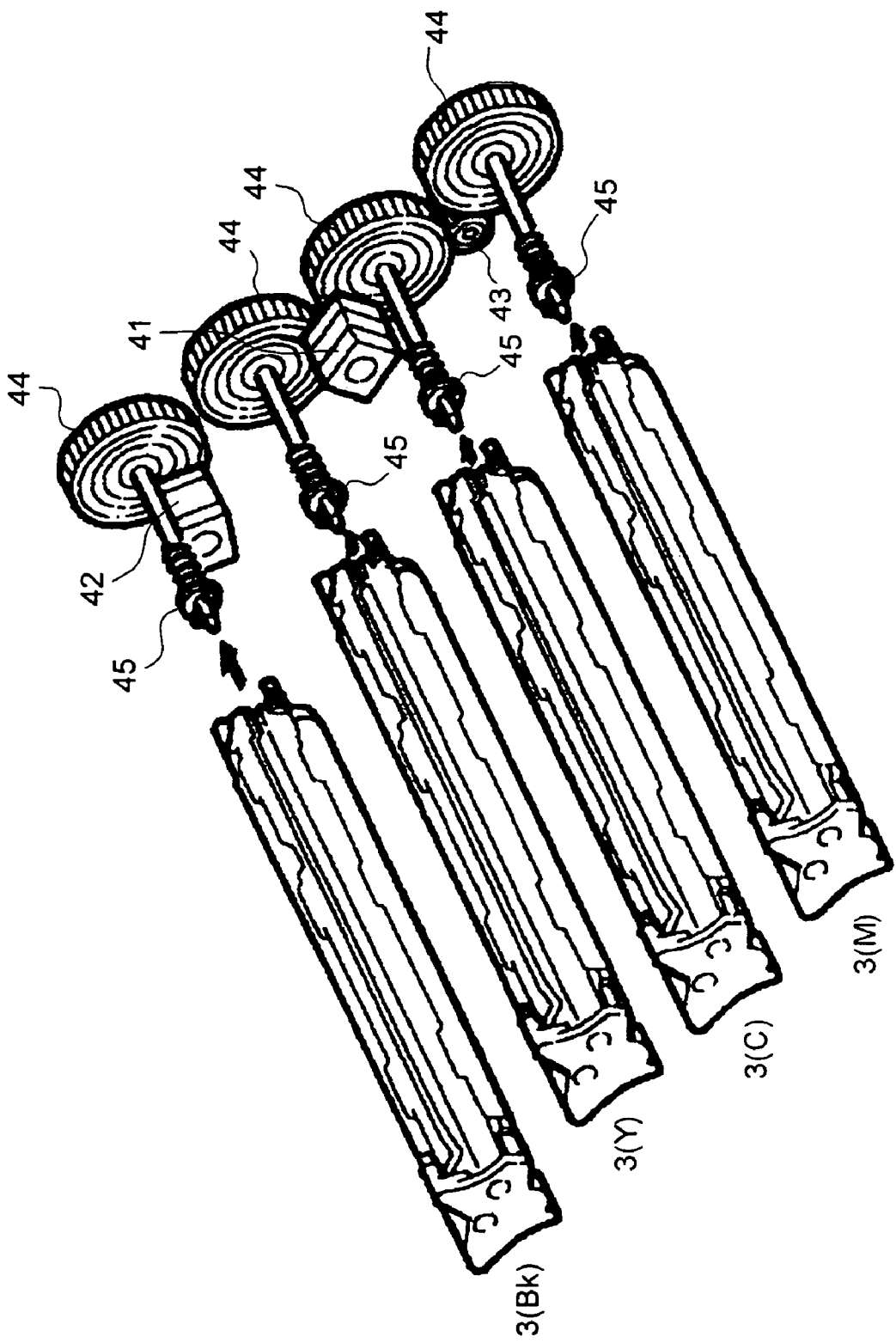
FIG. 4 is a schematic diagram of a mechanism to drive photosensitive drums.

FIG. 3 is a schematic diagram of the photosensitive unit 3 and the development unit 4 corresponding to a certain color. The photosensitive unit 3 has the photosensitive drum 28 having a diameter of φ30, for example. The photosensitive drum 28 has a hollow cylindrical shape, and is rotated in the clockwise direction in FIG. 3 by a driving mechanism described later.

A charging roller 36 having a diameter of φ11, for example, is disposed at an upper side of the photosensitive drum 28. The surface of the charging roller 36 is at a position of about 0.05 micrometers apart from the surface of the photosensitive drum 28. The charging roller 36 is rotated to a direction opposite to the rotation of the photosensitive drum 28, that is, in the counterclockwise direction in FIG. 3, thereby uniformly applying an electric charge onto the surface of the photosensitive drum 28.

A cleaning brush 37 is disposed at an upper side of the charging roller 36. A cleaning brush 39 and a counter blade 38 are disposed at a left upper side of the photosensitive drum 28, thereby cleaning the photosensitive drum 28.

A waste toner recovery coil 40 is disposed at the left of the cleaning brush 39. The waste toner recovered by the waste toner recovery coil 40 is fed to a waste toner bolt 16 shown in FIG. 1.

The development unit 4 employs a dry two-component magnetic brush development system, and includes a development roller 30, a development doctor 31, a feeder left screw 32, a feeder right screw 33, a toner concentration sensor 34, and a dosage cartridge 35.

Four photosensitive units 3 are provided corresponding to the four colors. A driving mechanism that drives the three photosensitive units 3 for M, C, and Y colors is different from the driving mechanism that drives the photosensitive unit 3 for Bk. In other words, a color drum driving motor 41 drives the color photosensitive units 3, using gears 43 and 44 and a joint 45 to transmit driving force.

On the other hand, a separate black drum driving motor 42 drives the photosensitive unit 3 for black color, using a separate gear 44 and a joint 45 to transmit driving force.

Therefore, during the printing in the color mode, only the color drum driving motor 41 operates, and the black drum driving motor 42 is at rest. On the other hand, during the printing in the monochrome mode, only the black drum driving motor 42 operates and, and the color drum driving motor 41 is at rest. The color drum driving motor 41 and the black drum driving motor 42 are stepping motors.

Figure 5:
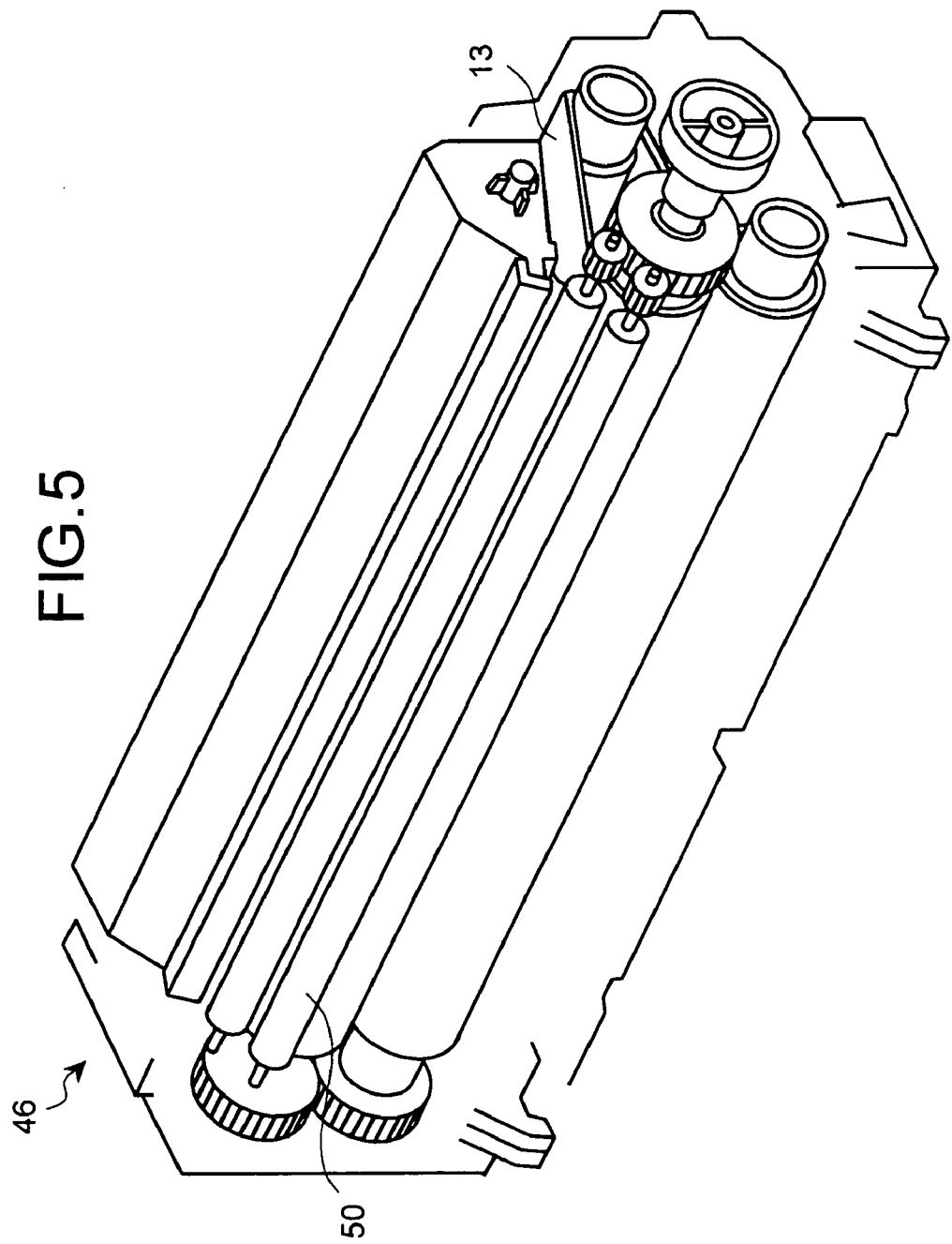
FIG. 5 is a schematic diagram of a fixing unit of the image forming apparatus.
Figure 6:
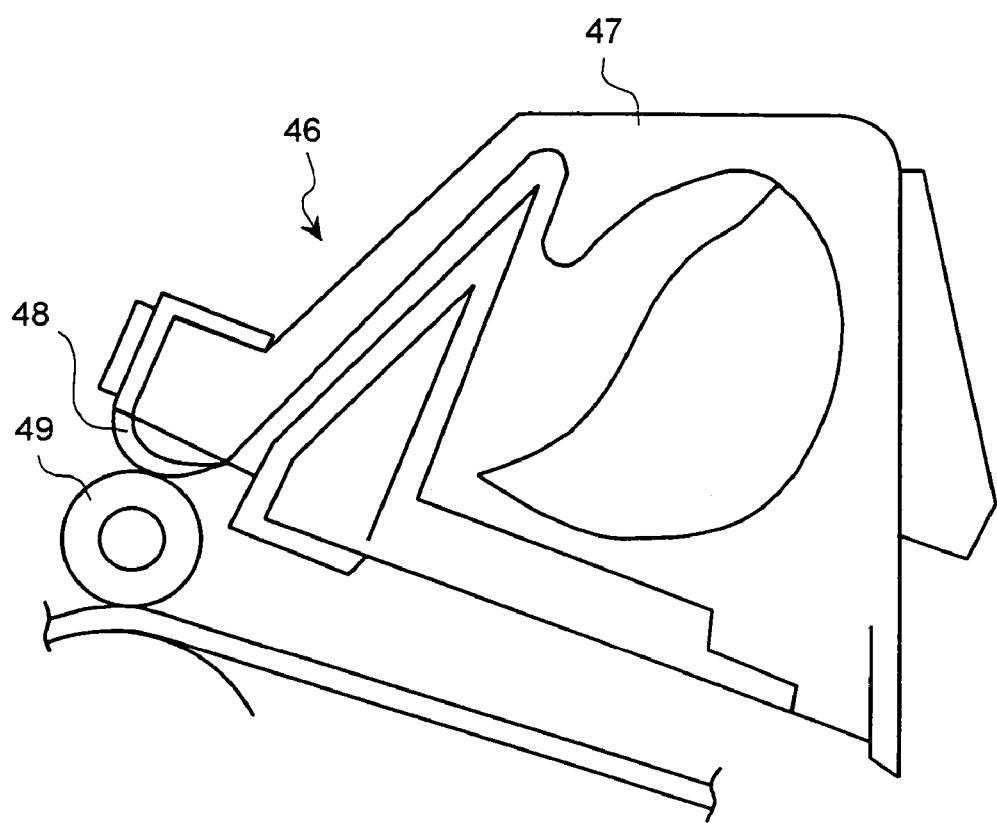
FIG. 6 is a front cross unit of the fixing unit.

As shown in FIG. 5 and FIG. 6, the fixing unit 46 employs a belt fixing system. The belt has a smaller thermal capacity than the fixing roller. Therefore, the employment of the belt fixing system has an advantage in that the warm up time can be made shorter than that of the fixing roller system, and that a roller setting temperature during the waiting can be lowered.

The fixing unit 46 heats and thermally presses paper onto which an image is transferred, and fixes a toner image on the paper. The fixing unit 46 has a fixing belt 13 and an oil applying unit 47. Gel is soaked out from oil into the oil applying unit 47, and is supplied from a applying felt 48 to an applying roller 49. The applying roller 49 coats a slight amount of silicone oil onto the fixing belt 13 while rotating. When the oil is coated onto the fixing belt 13, the paper can be separated easily from the fixing belt 13. The oil applying unit 47 carries out the applying each time when one sheet of paper is fed. A mechanism having a solenoid or a spring not shown drives the oil applying unit 47 to bring the oil applying unit 47 into contact with the fixing belt 13 each time when one sheet of paper is fed. On the other hand, when one sheet of paper passes, the above mechanism separates the oil applying unit 47 from the fixing belt 13.

A cleaning roller 50 is provided on the fixing belt 13 at the upstream of the paper feeding direction, as shown in FIG. 5. The cleaning roller 50 absorbs stain on the fixing belt 13, thereby cleaning the belt.

The fixing unit 46 has the configuration as explained above. The feeding roller feeds the paper having passed through the fixing unit 46 to a main tray 51 shown in FIG. 1.

The paper feeder 110 has three trays of a first tray 9, a second tray 10, and a manual paper feed tray 8. These trays employ a friction reverse roller (FRR) paper feeding system to feed sheets of paper accommodated in the trays. The mechanism according to the FRR paper feeding system has a reverse rotation knob that is brought into contact with a paper feeding knob that is rotated in the paper feeding direction, in order to separate each sheet of paper from a stack of paper piled within the paper feed tray.

Based on the above configuration, weak torque that is directed to an opposite direction of the paper feeding knob is applied to the reverse rotation knob through a torque limiter. Therefore, the reverse rotation knob rotates following the paper feeding knob when the reverse rotation knob is in contact with the paper feeding knob or when a sheet of paper is inserted into between both knobs. On the other hand, the reverse rotation knob rotates in the opposite direction when the reverse rotation knob is separated from the paper feeding knob or when two or more sheets of paper are inserted into between both knobs. Therefore, when sheets of paper in a superimposed state enter, the sheets of paper that are in contact with the reverse rotation knob is returned to the downstream of the paper feeding direction, thereby preventing the sheets of paper from being sent in the superimposed state.

The first paper feeding unit 51 separates a sheet of paper from the paper accommodated in the first tray 9, and feeds this sheet from the first tray 9. A relay roller 53 feeds this sheet of paper to a feeding roller 55. The feeding roller 55 turns this sheet of paper, and feeds this paper toward a resist roller 7 at a left upper side.

The fed paper is brought into contact with the suspended resist roller 7, which corrects skewing of the paper. The paper feeding timing is adjusted with the timing of the image forming process according to the photosensitive unit 3. At a predetermined timing, a resist clutch not shown is connected to the resist roller 7 to drive the resist roller 7, thereby feeding the paper to the transfer unit. The transfer belt 29 feeds the paper, and a predetermined image transfer is carried out onto the paper.

A second paper feeding unit 52 and a relay roller 54 feed a sheet of paper accommodated in the second tray 10 toward the feeding roller 55. Thereafter, the paper is fed in a similar manner to that for the paper accommodated in the first tray 9. The paper feeding unit 56 feeds the paper that is set in the manual feed tray 8 toward the resist roller 7. Thereafter, the paper is fed in a similar manner to that for the paper accommodated in the first tray 9.

Figure 8:
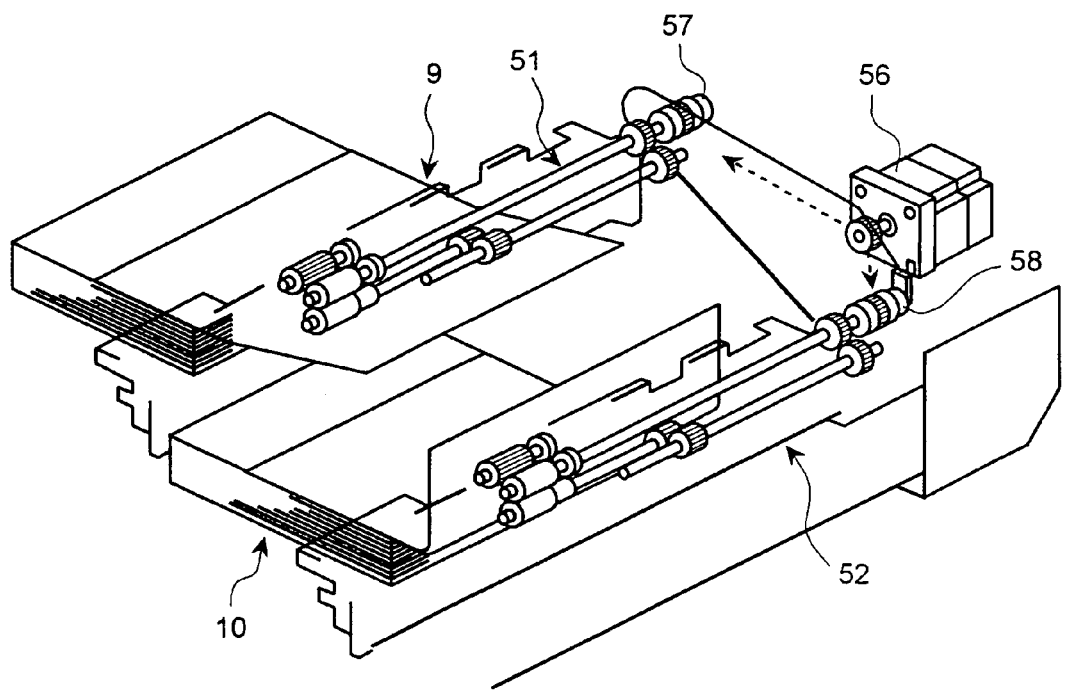
FIG. 8 is a schematic diagram of a driving mechanism of the paper feeder.

As shown in FIG. 8, one stepping motor 56 drives both units. Driving force is transmitted to both units via a first paper feeding clutch 57 and a second paper feeding clutch 58. In other words, when paper is fed from the first tray 9, only the first paper feeding clutch 57 is connected. When paper is fed from the second tray 10, only the second paper feeding clutch 58 is connected.

The image forming apparatus has the photosensitive units 3 for colors, and can carry out color printing as well as monochrome printing, as described above. More specifically, the image forming apparatus has four printing modes of a monochrome mode, a color mode (1), a color mode (2), and an OHP/thick paper mode, as shown in Table 1. When a user selects a printing mode by operating an operation unit, a controller 1000 (see FIG. 1) of the image forming apparatus controls each unit of the apparatus to make each unit operate in the selected operation mode. A controller 2000 shown in FIG. 1 is actually a circuit, and is not disposed at a position shown in FIG. 1. The controller 2000 is shown in FIG. 1 to make it clear that the image forming apparatus is equipped with this controller.

In the image forming apparatus, the controller 2000 switches the image forming speed between three kinds of speed, including 182.5 mm/s=38 ppm, 125.0 mm/s=28 ppm, and 62.5 mm/s=14 ppm. In other words, the image forming apparatus controls the revolution speed of the motor to change corresponding to the stepping motor 56, the black drum driving motor 42, and the color drum driving motor 41, according to the selected operation mode. In the present specification, "ppm" refers to the number of pages of A4 horizontal size sheets of paper that are output per minute.

TABLE 1

| Paper feeding speed (mm/s) | Mode | Resolution (dpi) | PPM |
| --- | --- | --- | --- |
| 185.0 | Monochrome | 600 × 600 | 38 |
| 125.0 | Color (1) | 600 × 600 | 28 |
| 62.5 | Color (2) | 1200 × 1200 | 14 |
| 62.5 | OHP/thick paper | 1200 × 1200 | 14 |

In the color mode (2) and the OHP/thick paper mode in high resolution, the printing speed (i.e., image forming speed) is 14 ppm. On the other hand, the printing speed is 38 ppm in the monochrome mode, which is almost three times the printing speed in high resolution. In order to achieve this large speed difference with one motor, the image forming apparatus employs stepping motors as driving sources of the paper feeding mechanism and the like.

The present invention provides a modifying method of evaluating noise that the image forming apparatus having the above configuration generates, and decreasing discomfort that the noise gives to a person based on a result of the evaluation. The method of evaluating noise that the image forming apparatus generates during the image forming will be explained.

The present inventor evaluates sound quality based on the following concept. In order to subjectively evaluate a discomfort of machine noise, a standard of measuring discomfort is necessary. As a method of setting this standard, a pair comparison method is available. According to the pair comparison method, a pair of stimuli is prepared for a stimulus for which absolute evaluation is difficult, such as sound generated from the image forming apparatus. Pairs of stimuli are prepared using all combinations of stimuli for which evaluation is to be carried out. A difference between scores of the stimuli is obtained, and a relative evaluation score is given to each stimulus. This method is provided in the light of a fact that a person finds it difficult to evaluate one stimulus but finds it relatively easy to comparatively determine which one of two stimuli is worse.

For example, assume that three stimuli A1, A2, and A3 are present. Each stimulus model is set as $y1=\mu+\alpha 1$, $y2=\mu+\alpha 2$, $y3=\mu\alpha 3$. For simplicity, it is assumed that this model includes only a total average $\mu$, and a main effect $\alpha i$ ($i=1, 2,$ and 3). The summation of the main effect is assumed as zero, like a general constraint that is necessary to estimate parameters in an experimental design.

$$\alpha 1 + \alpha 2 + \alpha 3 = 0 \quad (1)$$

A fact that an absolute evaluation cannot be carried out means that the value of $\mu$ cannot be estimated. Therefore, y1, y2, and y3 cannot be measured directly. When a difference between two stimuli is obtained, $\mu$ disappears, and only a difference between main effects can be expressed.

$$y1-y2=(\mu+\alpha 1)-(\mu+\alpha 2)=\alpha 1-\alpha 2 \quad (2)$$

$$y1-y3=(\mu+\alpha 1)-(\mu+\alpha 3)=\alpha 1-\alpha 3 \quad (3)$$

$$y2-y3=(\mu+\alpha 2)-(\mu+\alpha 3)=\alpha 2-\alpha 3 \quad (4)$$

where (2)+(3) is $$2y1-(y2+y3)=2\alpha 1-(\alpha 2+\alpha 3).$$

From the above constraint (1), $$2y1-(y2+y3)=3\alpha 1.$$

In other words, the effect of each stimulus can be obtained. When the effect of each stimulus is expressed as a primary function based on a difference between physical characteristics that the image forming apparatus has, the following function is obtained:

$$\alpha 1-\alpha 2=b(x1-x2)$$

where b represents a constant, and xi represents i=1, 2, 3, . . . , and n. An intercept is offset by modeling a difference between two stimuli.

A difference between scores is set as a target variable, and a difference between a plurality of physical characteristics (i.e., psycho-acoustic parameters, etc.) is set as an explanation variable group. When a multiple linear regression analysis is carried out, an estimating model of an evaluation difference can be obtained. In other words, when physical characteristics having two sounds to be compared are input, a model that can output an estimate difference between evaluations about different discomfort levels of the two sounds can be obtained.

Among the conventional methods, there is one for obtaining a multiple linear regression model by calculating a relative evaluation score for each stimulus according to Scheffe's pair comparison method (i.e., Ura's modified method), and using the score as a target variable and using the sound quality characteristics (such as psycho-acoustic parameters) of stimulus as an explanatory variable.

However, in the present invention, the conventional method is improved to combine a plurality of experiment results. In other words, according to the conventional method, a model expression needs to be derived in each experiment. Further, as the pair comparison needs to be carried out for all the pairs of stimuli to derive scores, the scale of experiment becomes enormously large. When the image forming apparatus has a plurality of operation modes as explained above, the characteristics of sounds generated from the image forming apparatus in each operation mode are entirely different. Therefore, it is very complex to derive model expressions corresponding to respective operation modes of the image forming apparatus.

The present inventor focuses attention on the fact that a unified model expression can be obtained by carrying out a multiple linear regression analysis using a score of a difference between stimuli as a target variable and using a difference between psycho-acoustic parameters of two stimuli as an explanatory variable based on the assumption that regression coefficients (i.e., an inclination of a straight line) of sound quality characteristics are equal in each pair comparison experiment. In the present invention, a final target evaluation object is not a difference between discomfort levels but a score of discomfort of sound. Therefore, an estimating model of a difference between discomfort levels is derived first as described above. Then, the model expression derived based on a standard is converted into an estimating model expression of a score of discomfort of a single sound.

The present inventor derives a model expression to estimate a score of discomfort of sound, according to the above concept. The sound quality of sound generated from the image forming apparatus is evaluated. The process of experiments actually carried out will be explained in detail.

The flow of the sound quality evaluation experiments of the image forming apparatus and the deriving of the sound quality evaluation expression is as follows.

(1-1) Collection of operation noise from the image forming apparatus
(1-2) Analysis of the operation noise
(1-3) Creation of sample sound from the collected operation noise
(1-4) Measurement of psycho-acoustic parameters of the sample sound
(1-5) Pair comparison method experiment using the sample sound
(1-6) Identification of a source of unpleasant noise
(1-7) Preparation of analysis data of a differential model
(1-8) Deriving of an expression to estimate a difference between scores
(1-9) Deriving of a model expression (i.e., a sound quality evaluation expression) to estimate scores
(1-10) Verification of a derived sound quality evaluation expression Details of the above process will be explained below.

First, the process of (1-1) collection of operation noise of the image forming apparatus will be explained.

A dummy head HMS (head measurement system) III manufactured by Head Acoustics GmbH is used to carry out binaural recording to collect operation noise of the image forming apparatus. When the binaural recording is carried out and the exclusive headphone is used to reproduce sound, the sound can be reproduced in the feeling that a person actually hears the sound generated from the machine. The image forming apparatus as the apparatus for sound measurement actually executes the image forming operation at three kinds of image forming speed corresponding to the operation modes. The measurement is carried out in the following conditions for each of the three operation modes (see FIG. 9).

*Recording environment . . . a semi-anechoic chamber
*Position of ears of a dummy head 203 (i.e., sound collection position) 204 . . . height 1.2 meters, a horizontal distance from the end surface of a measured apparatus 201 about 1 meter (1±0.03), and at the center of the apparatus in a lateral direction
*Recording direction . . . four directions of the front surface (i.e., the surface on which an operation unit 202 of the image forming apparatus is present), the back surface, and the left and right surfaces
*Recording mode . . . FF (free field; for anechoic chamber)
*HP (headphone) filter . . . 22 hertz The height of the dummy head is set to 1.2 meters in consideration of a fact that recently, a user gives instructions to a personal computer or the like in a seated state when the user utilizes the image forming apparatus. The dummy head can also be set to a height of 1.5 meters assuming that the user operates the image forming apparatus in standing.

Sounds generated from the image forming apparatus are always different depending on directions of the sounds. Various motors, paper feeding routes and a paper discharge port are not always located at the center of the apparatus but are located at distributed positions. Therefore, sound generated from a certain sound source (such as a motor) may be clearly audible at the right surface side and may not be clearly audible at the left surface side. Thus, collected sounds are different depending on the directions. A sample sound to be used in the experiments described later may be collected from any direction. However, in order to carry out a pair comparison experiment, the direction of collecting sounds must be consistent. In most cases, a user may hear sound at the front surface side of the image forming apparatus. On the other hand, a user may have a small opportunity to hear sound at the back surface side of the image forming apparatus that usually faces a wall. Therefore, in the present experiment, sound collected at the front surface side is used as the sample sound.

The process of (1-2) analysis of the operation noise will be explained next. In this process, the operation noise of the image forming apparatus collected during each operation mode is analyzed.

Figure 10:
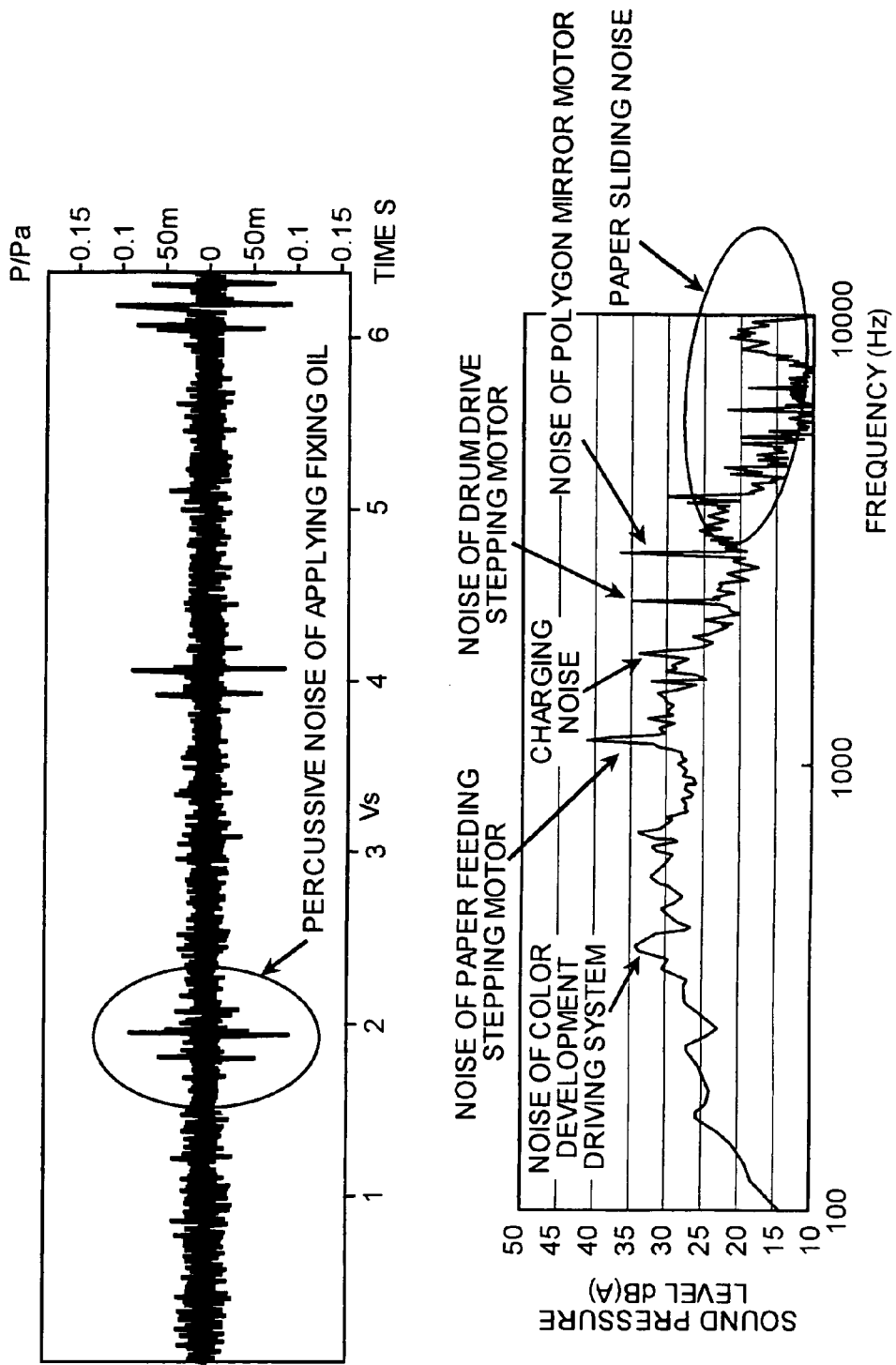
FIG. 10 is a graph of a result of an analysis of the sound measured when the image forming apparatus is operating in one mode.

When the image forming apparatus operates in the color mode (1) at the printing speed of 28 ppm, the sound generated is analyzed, and a result of the analysis is obtained as shown in FIG. 10. The upper side of the graph shown in FIG. 10 represents sound collected on the time axis, and the lower side of the graph represents sound collected on the frequency axis. From this result, seven main sound sources are extracted. First, on the time axis, applying percussive noise of fixing oil in the fixing unit 46 is extracted. On the frequency axis, noise of the color development driving system, noise of the paper feeding stepping motor, charging noise, noise of the drum drive stepping motor, noise of the polygon mirror motor, and paper sliding noise are extracted.

Figure 11:
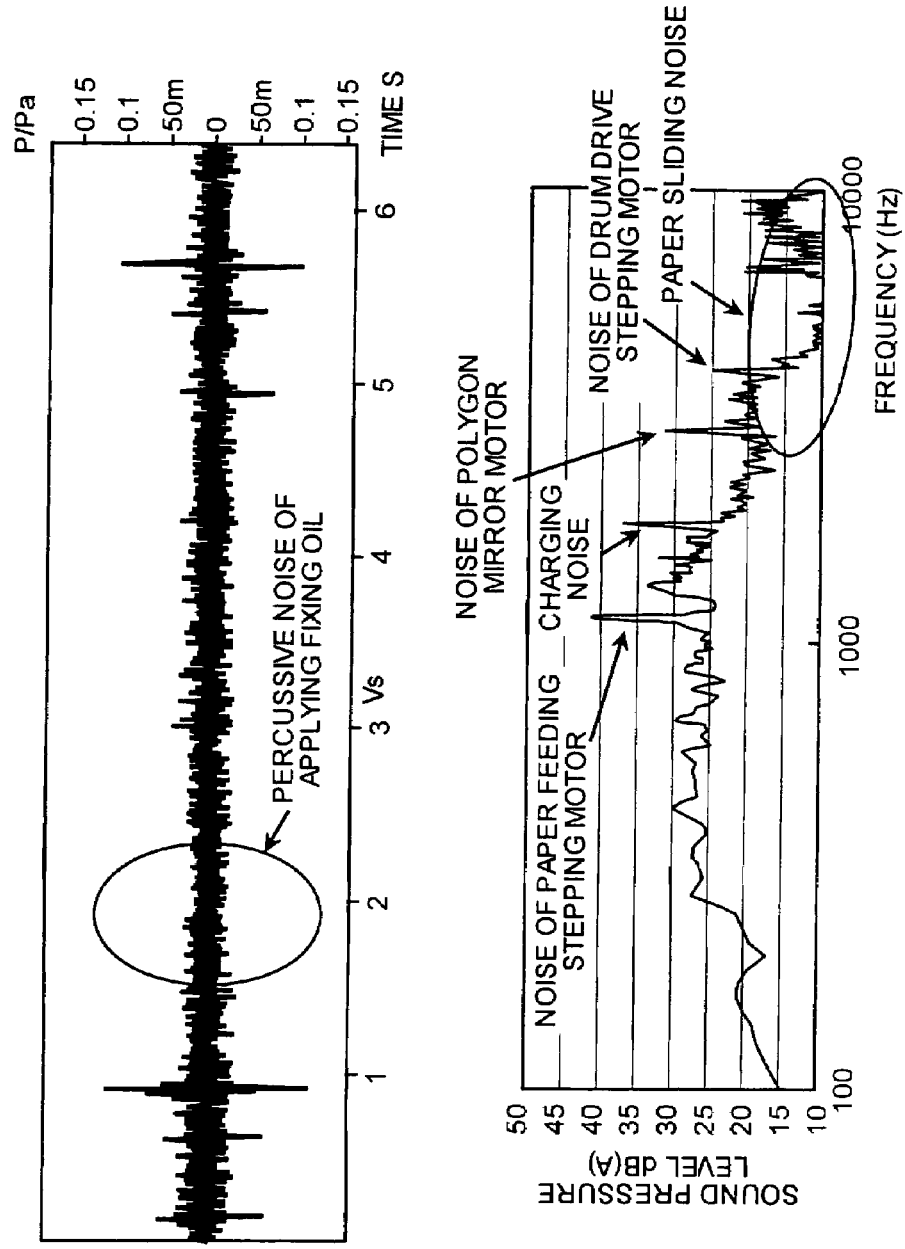
FIG. 11 is a graph of a result of an analysis of the sound measured when the image forming apparatus is operating in other mode.

When the image forming apparatus operates in the color mode (2) at the printing speed of 14 ppm, the sound generated is analyzed, and a result of the analysis is obtained as shown in FIG. 11. The upper side of the graph shown in FIG. 11 represents sound collected on the time axis, and the lower side of the graph represents sound collected on the frequency axis. From this result, the following main sound sources are extracted. On the time axis, applying percussive noise of fixing oil is extracted. On the frequency axis, noise of the paper feeding stepping motor, charging noise, noise of the drum drive stepping motor, noise of the polygon mirror motor, and paper sliding noise are extracted.

Figure 12:
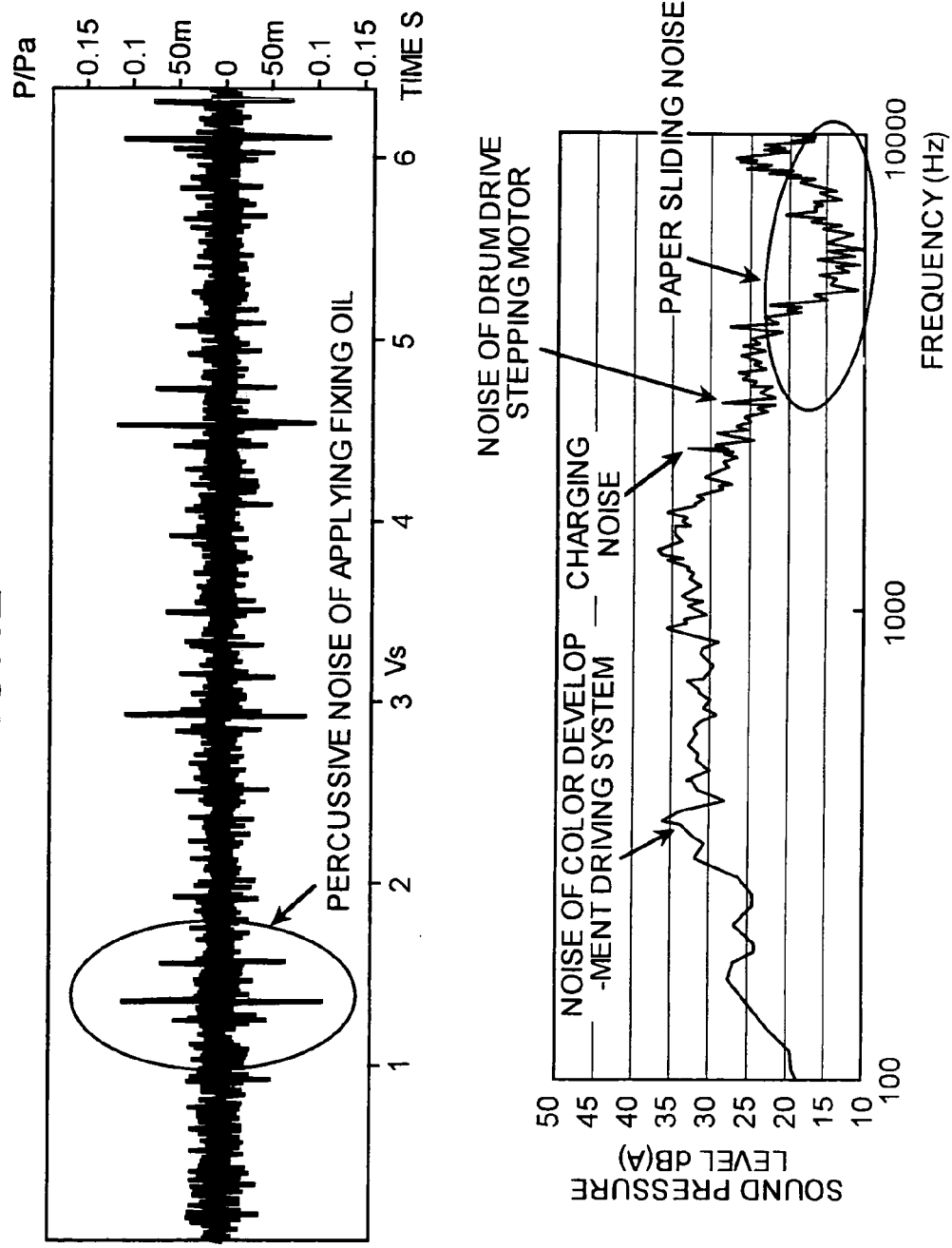
FIG. 12 is a graph of a result of an analysis of the sound measured when the image forming apparatus is operating in another mode.

When the image forming apparatus operates in the monochrome mode at the printing speed of 38 ppm, the sound generated is analyzed, and a result of the analysis is obtained as shown in FIG. 12. The upper side of the graph shown in FIG. 12 represents sound collected on the time axis, and the lower side of the graph represents sound collected on the frequency axis. From this result, the following main sound sources are extracted. On the time axis, applying percussive noise of fixing oil is extracted. On the frequency axis, noise of the color development driving system, charging noise, noise of the drum drive stepping motor, and paper sliding noise are extracted.

The process of (1-3) creation of sample sound from the collected operation noise will be explained next. In this process, "ArtemiS" as sound quality analysis software of Head Acoustics GmbH is used to collect sound at the front surface side of the apparatus and process the collected sound.

As a method of processing the sound in the present experiment, sound during one printing operation cycle is extracted from the collected original sound. Out of the sound during the one cycle, the portions of the sound concerning the extracted main sound sources are filtered on the frequency axis or the time axis and the portions are damped and emphasized. In other words, three standard sounds (i.e., emphasis, original sound, and damping) are created from sounds generated from sound sources obtained during the operation in one operation mode.

As explained above, sounds collected at the front side, the back side, the left side, and the right side of the image forming apparatus are different. On the other hand, it is confirmed that a range of psycho-acoustic parameters obtained from the three sample sounds created by emphasizing and damping the sound collected at the front surface side and created by the experiment is larger than the range of psycho-acoustic parameters that are obtained from the sounds in the four directions. In other words, when the three sounds obtained by emphasizing and damping the sound collected at the front surface side are used to carry out a subjective evaluation experiment like in the present experiment, it is possible to obtain a sound quality evaluation expression that covers characteristics of the sounds obtained from the sounds collected in the four directions. Based on this sound quality evaluation expression, discomfort levels in the four directions can be calculated.

The three standard sounds (i.e., emphasis, original sound, and damping) are created from sounds generated from the main sound sources that are extracted for each of the three operation modes, based on the sound collected at the front surface side. Nine sounds are created based on an L9 orthogonal array for combinations of different standards of the sound sources extracted for each mode. In the subjective evaluation experiment, a round-robin comparative experiment needs to be carried out. Therefore, 72 comparative experiments are carried out for the nine sounds.

Table 2 expresses a result of creating the nine sample sounds by allocating the three standard sounds based on the L9 orthogonal array, where the three standard sounds are created for seven main sound sources extracted from the sound collected when the image forming apparatus operates in the color mode (1) at the printing speed of 28 ppm. There is no correlation between factors (i.e., standard changes of the sound source). Therefore, when the sounds are allocated to the orthogonal array, the analysis can be carried out by disregarding changes in other factors.

TABLE 2

| Sample sound | Fixing oil applying noise | Paper STM noise | Paper sliding noise | Charging noise | Drum STM noise | Polygon M noise | Color development driving noise | Subjective evaluation value |
| --- | --- | --- | --- | --- | --- | --- | --- | --- |
| Color 28 ppm (1) | −1 | −1 | −1 | −1 | 1 | 0 | −1 | −0.419 |
| Color 28 ppm (2) | −1 | 1 | 0 | 1 | −1 | 1 | −1 | 0.178 |
| Color 28 ppm (3) | −1 | −1 | 1 | −1 | −1 | −1 | 0 | −0162 |
| Color 28 ppm (4) | −1 | 0 | −1 | 1 | 0 | −1 | 1 | −0.286 |
| Color 28 ppm (5) | 0 | 0 | −1 | −1 | −1 | 1 | 1 | −0.048 |
| Color 28 ppm (6) | 1 | −1 | −1 | 0 | −1 | −1 | −1 | 0.098 |
| Color 28 ppm (7) | −1 | 1 | −1 | −1 | −1 | −1 | −1 | −0.0663 |
| Color 28 ppm (8) | 1 | 0 | 1 | −1 | 1 | −1 | −1 | 0.810 |
| Color 28 ppm (9) | 0 | 0 | 0 | 0 | 0 | 0 | 0 | 0.492 |

In this table (and also in the subsequent tables), "−1" represents sound that is created by damping the sound until the sound is not audible. "0" represents sound at the original sound level. "1" represents sound that is emphasized until when there is a clear difference between the original sound level and this sound level. For example, sample sound "color 28 ppm (9)" in Table 2 has "0" for all the sound sources. Therefore, this indicates that these sounds are all original sounds.

Table 2 also expresses subjective evaluation values of sample sounds that are obtained from the comparative experiment described later.

Table 3 expresses a result of allocating the three standard sounds based on the L9 orthogonal array, where the three standard sounds are created for six main sound sources extracted from the sound collected when the image forming apparatus operates in the color mode (2) at the printing speed of 14 ppm. The charging noise, the noise of the drum drive stepping motor, and the noise of the polygon mirror motor are the sounds of the same tonality component. Therefore, these sample sounds are at the same standard levels. The noise of the paper feeding stepping motor is also the tonality component. However, as this sound is generated intermittently, this sound has a separate standard from that of the motor sound.

TABLE 3

| Sample sound | Fixing oil applying noise | Paper STM noise | Charging, polygon, drum stepping noise | Paper sliding noise | Subjective evaluation value |
|---|---|---|---|---|---|
| Color 14 ppm (1) | 0 | 0 | 0 | 0 | 0.140 |
| Color 14 ppm (2) | 0 | 1 | 1 | −1 | 0.013 |
| Color 14 ppm (3) | 0 | −1 | −1 | 1 | 0.013 |
| Color 14 ppm (4) | 1 | 0 | 1 | 1 | 0.719 |
| Color 14 ppm (5) | 1 | 1 | −1 | 0 | 0.489 |
| Color 14 ppm (6) | 1 | −1 | 0 | −1 | −0.263 |
| Color 14 ppm (7) | −1 | 0 | −1 | −1 | −0.819 |
| Color 14 ppm (8) | −1 | 1 | 0 | 1 | 0.149 |
| Color 14 ppm (9) | −1 | −1 | 1 | 0 | −0.540 |

Table 4 expresses a result of allocating the three standard sounds based on the L9 orthogonal array, where the three standard sounds are created for five main sound sources extracted from the sound collected when the image forming apparatus operates in the monochrome mode at the printing speed of 38 ppm. The charging noise and the noise of the drum drive stepping motor are the sounds of the same tonality component. Therefore, these sample sounds are at the same standard levels.

TABLE 4

| Sample sound | Fixing oil applying noise | AC charge, drum STM motor noise | Color development driving system noise | Paper sliding noise | Subjective evaluation value |
|---|---|---|---|---|---|
| Monochrome 38 ppm (1) | 0 | 0 | 0 | 0 | 0.010 |
| Monochrome 38 ppm (2) | 0 | 1 | 1 | −1 | −0.052 |
| Monochrome 38 ppm (3) | 0 | −1 | −1 | 1 | 0.087 |
| Monochrome 38 ppm (4) | 1 | 0 | 1 | 1 | 0.847 |
| Monochrome 38 ppm (5) | 1 | 1 | −1 | 0 | 0.458 |
| Monochrome 38 ppm (6) | 1 | −1 | 0 | −1 | −0.142 |
| Monochrome 38 ppm (7) | −1 | 0 | −1 | −1 | −0.837 |
| Monochrome 38 ppm (8) | −1 | 1 | 0 | 1 | 0.128 |
| Monochrome 38 ppm (9) | −1 | −1 | 1 | 0 | −0.500 |

In the present experiment, the three standard sounds (i.e., emphasis, original sound, and damping) are created from a loudness value, a sharpness value, a tonality value, and an impulsiveness value as the psycho-acoustic parameters that are obtained from the sound collected at the front surface side when the three operation modes are mixed. These sounds are allocated to create sample sounds based on the L9 orthogonal array. Table 5 expresses a result of the creation of the sample sounds.

TABLE 5

| Sample sound | Loudness (sone) | Sharpness (acum) | Tonality (tu) | Impulsiveness (iu) | Sound pressure level DB(A) | Speed | Subjective evaluation value |
|---|---|---|---|---|---|---|---|
| Mixed (1) | +1 (8.1) | +1 (2.7) | 0 (0.12) | +1 (0.78) | 54.8 | Monochrome 38 ppm | 0.832 |
| Mixed (2) | +1 (9.0) | −1 (1.9) | +1 (0.18) | 0 (0.66) | 55.1 | Monochrome 38 ppm | 0.404 |
| Mixed (3) | +1 (10.1) | 0 (2.4) | −1 (0.06) | −1 (0.44) | 55.6 | Monochrome 38 ppm | 0.249 |
| Mixed (4) | 0 (8.5) | 0 (2.4) | 0 (0.12) | 0 (0.56) | 54.0 | Color 28 ppm | 0.182 |
| Mixed (5) | 0 (7.5) | +1 (2.8) | +1 (0.18) | −1 (0.35) | 51.6 | Color 28 ppm | −1.189 |
| Mixed (6) | 0 (6.5) | −1 (1.8) | −1 (0.06) | +1 (0.84) | 52.5 | Color 28 ppm | −0.242 |

TABLE 5-continued

| Sample sound | Loudness (sone) | Sharpness (acum) | Tonality (tu) | Impulsiveness (iu) | Sound pressure level DB(A) | Speed | Subjective evaluation value |
|---|---|---|---|---|---|---|---|
| Mixed (7) | −1 (7.0) | −1 (1.9) | 0 (0.13) | −1 (0.42) | 50.8 | Color 14 ppm | −0.653 |
| Mixed (8) | −1 (6.0) | 0 (2.3) | +1 (0.17) | 0 (0.76) | 51.9 | Color 14 ppm | 0.067 |
| Mixed (9) | −1 (5.0) | +1 (2.8) | −1 (0.06) | +1 (0.77) | 48.6 | Color 14 ppm | −0.350 |

For the loudness value, the allocation is carried out as follows. Emphasized sound is allocated to the monochrome mode at the printing speed of 38 ppm. Intermediate sound is allocated to the color mode (1) at the printing speed of 28 ppm. Damped sound is allocated to the color mode (2) at the printing speed of 14 ppm. In other words, standard values of loudness are allocated corresponding to the printing speeds. Numerals within parentheses in Table 5 represent parameter values. In the present experiment, the influence of the printing speed (ppm), that is, the effect of the printing speed, is also confirmed. When the printing speed and the loudness value change completely proportionately, the effect cannot be analyzed. Therefore, as shown in Table 5, a difference of about 1 (sone) is provided, although the loudness values are at the same standard, thereby providing a difference in the loudness.

The process of creating the sample sounds from the collected operation noise is explained in detail above.

The process of (1-4) measurement of psycho-acoustic parameters of the sample sound will be explained next.

In this process, the sound quality analysis software "ArtemiS" of Head Acoustics GmbH is used to obtain psycho-acoustic parameters for the sample sounds created above. According to this sound quality analysis software, various settings can be selected to obtain the psycho-acoustic parameters. In the present experiment, a default setting is employed.

For example, "FFT/IS00532", "Filter/IS00532", and "FFT/HEAD" can be selected as "Calculation method" for loudness. In the present experiment, default "FFT/IS00532" is employed. Default "4096" is used for "Spectrum Size". Default "FFT/IS0532" is employed for "Calculation method" for sharpness. For "Sharpness method", default "Aures" is employed out of "Aures" and "von Bismarck". Default "4096" is used for "Spectrum Size". Other psycho-acoustic parameters have correlation with loudness, and changes automatically based on the setting of loudness.

The psycho-acoustic parameter values of the sample sounds created in the process of (1-3) are obtained by using the sound quality analysis software that is set above. Table 6 expresses a result of obtained psycho-acoustic parameter values.

TABLE 6

| Sample sound | Sound pressure level dB(A) | Loudness (sone) | Sharpness (acum) | Tonality (tu) | Roughness (asper) | Impulsiveness (iu) | Relative approach | PPM |
|---|---|---|---|---|---|---|---|---|
| Color 28 ppm (1) | 47.4 | 5.38 | 1.89 | 0.14 | 1.12 | 0.42 | 1.36 | 28.0 |
| Color 28 ppm (2) | 53.1 | 7.33 | 2.32 | 0.15 | 1.36 | 0.38 | 1.51 | 28.0 |
| Color 28 ppm (3) | 49.2 | 6.75 | 2.66 | 0.06 | 1.43 | 0.46 | 1.55 | 28.0 |
| Color 28 ppm (4) | 50.2 | 6.29 | 1.68 | 0.16 | 1.19 | 0.38 | 1.45 | 28.0 |
| Color 28 ppm (5) | 50.9 | 6.42 | 1.75 | 0.10 | 1.48 | 0.63 | 1.59 | 28.0 |
| Color 28 ppm (6) | 50.9 | 5.77 | 1.88 | 0.07 | 1.54 | 0.79 | 1.59 | 28.0 |
| Color 28 ppm (7) | 50.8 | 5.64 | 1.72 | 0.09 | 1.22 | 0.45 | 1.41 | 28.0 |
| Color 28 ppm (8) | 56.1 | 8.23 | 2.82 | 0.13 | 1.89 | 0.67 | 1.82 | 28.0 |
| Color 28 ppm (9) | 52.2 | 7.51 | 2.34 | 0.13 | 1.66 | 0.57 | 1.70 | 28.0 |
| Color 14 ppm (1) | 49.8 | 5.91 | 2.28 | 0.18 | 1.39 | 0.60 | 1.59 | 14.0 |
| Color 14 ppm (2) | 51.6 | 6.19 | 1.96 | 0.25 | 1.20 | 0.59 | 1.49 | 14.0 |
| Color 14 ppm (3) | 48.3 | 5.08 | 2.74 | 0.05 | 1.36 | 0.77 | 1.60 | 14.0 |
| Color 14 ppm (4) | 55.3 | 7.19 | 2.60 | 0.19 | 1.82 | 0.73 | 1.89 | 14.0 |
| Color 14 ppm (5) | 51.6 | 6.02 | 2.50 | 0.16 | 1.53 | 0.80 | 1.74 | 14.0 |
| Color 14 ppm (6) | 50.0 | 4.76 | 1.60 | 0.13 | 1.30 | 0.90 | 1.63 | 14.0 |
| Color 14 ppm (7) | 43.4 | 4.10 | 1.79 | 0.11 | 0.83 | 0.50 | 1.20 | 14.0 |
| Color 14 ppm (8) | 50.0 | 6.63 | 2.66 | 0.21 | 1.23 | 0.38 | 1.40 | 14.0 |
| Color 14 ppm (9) | 50.1 | 5.39 | 2.08 | 0.15 | 1.11 | 0.45 | 1.35 | 14.0 |
| Monochromatic 38 ppm (1) | 53.8 | 8.52 | 2.47 | 0.06 | 1.97 | 0.65 | 1.76 | 38.0 |
| Monochromatic 38 ppm (2) | 55.0 | 8.92 | 2.00 | 0.09 | 1.87 | 0.65 | 1.71 | 38.0 |
| Monochromatic 38 ppm (3) | 53.5 | 7.98 | 2.96 | 0.05 | 1.85 | 0.67 | 1.73 | 38.0 |
| Monochromatic 38 ppm (4) | 59.2 | 10.73 | 2.79 | 0.07 | 2.47 | 0.80 | 2.03 | 38.0 |
| Monochromatic 38 ppm (5) | 55.9 | 8.76 | 2.69 | 0.07 | 2.12 | 0.80 | 1.83 | 38.0 |
| Monochromatic 38 ppm (6) | 54.2 | 7.47 | 1.86 | 0.05 | 2.02 | 0.86 | 1.75 | 38.0 |
| Monochromatic 38 ppm (7) | 48.3 | 6.16 | 2.00 | 0.07 | 1.28 | 0.45 | 1.44 | 38.0 |
| Monochromatic 38 ppm (8) | 53.7 | 9.13 | 2.83 | 0.08 | 1.69 | 0.43 | 1.69 | 38.0 |
| Monochromatic 38 ppm (9) | 53.9 | 8.48 | 2.22 | 0.08 | 1.69 | 0.45 | 1.65 | 38.0 |
| Mixed (1) | 54.8 | 8.06 | 2.71 | 0.12 | 1.93 | 0.78 | 1.75 | 38.0 |
| Mixed (2) | 55.1 | 8.99 | 1.85 | 0.18 | 1.56 | 0.66 | 1.70 | 38.0 |
| Mixed (3) | 55.6 | 10.11 | 2.39 | 0.06 | 1.84 | 0.44 | 1.81 | 38.0 |

TABLE 6-continued

| Sample sound | Sound pressure level dB(A) | Loudness (sone) | Sharpness (acum) | Tonality (tu) | Roughness (asper) | Impulsiveness (iu) | Relative approach | PPM |
|---|---|---|---|---|---|---|---|---|
| Mixed (4) | 54.0 | 8.49 | 2.36 | 0.12 | 1.78 | 0.56 | 1.79 | 28.0 |
| Mixed (5) | 51.6 | 7.46 | 2.81 | 0.18 | 1.32 | 0.35 | 1.49 | 28.0 |
| Mixed (6) | 52.5 | 6.53 | 1.80 | 0.06 | 1.72 | 0.84 | 1.71 | 28.0 |
| Mixed (7) | 50.8 | 7.01 | 1.93 | 0.13 | 1.42 | 0.42 | 1.58 | 14.0 |
| Mixed (8) | 51.9 | 6.00 | 2.29 | 0.17 | 1.62 | 0.76 | 1.77 | 14.0 |
| Mixed (9) | 48.6 | 5.05 | 2.82 | 0.06 | 1.41 | 0.77 | 1.58 | 14.0 |
| Total average | 52.0 | 7.07 | 2.28 | 0.12 | 1.56 | 0.61 | 1.63 | 26.7 |
| Color 28 ppm average | 51.2 | 6.59 | 2.12 | 0.11 | 1.43 | 0.53 | 1.55 | 28.0 |
| Color 14 ppm average | 50.0 | 5.70 | 2.25 | 0.16 | 1.31 | 0.64 | 1.55 | 14.0 |
| Monochromatic 38 ppm average | 54.2 | 8.46 | 2.42 | 0.07 | 1.88 | 0.64 | 1.73 | 38.0 |
| Mixed average | 52.8 | 7.52 | 2.33 | 0.12 | 1.62 | 0.62 | 1.69 | 26.7 |

The process of (1-5) pair comparison method experiment using the sample sound will be explained next. In this process, testers who evaluate the sample sounds created above are assembled. The testers carry out the pair comparison of the sample sounds (1) to (9) that are created for each mode (i.e., the color mode (1), the color mode (2), the monochrome mode. and a mixed mode), and judge which sound is unpleasant.

In this comparative experiment, all combinations of two sample sounds are extracted from the nine sample sounds. N testers compare all the combinations of sounds. In other words, as one mode has nine sample sounds, there are 72 combinations of sound in total. The testers compare these combinations of sound. Therefore, the evaluation of a combination of the sample sound (1) and the sample sound (2) is different from the evaluation of a combination of the sample sound (2) and the sample sound (1). The testers test these combinations of sample sounds, of which order of hearing the sounds is different.

In this comparison, a tester compares the sample sound (1) with the sample sound (2). When the tester evaluates that the sample sound (1) is unpleasant, the tester gives "score 1", and when the tester evaluates that the sample sound (2) is unpleasant, the tester gives "score −1". The results of evaluations are statistically processed, and a relative subjective evaluation value is obtained for the nine sample sounds within the range from −1 to 1. Table 2 to Table 5 express these subjective evaluation values. When certain sound has a larger value of subjective evaluation, this means that this sound is more unpleasant.

The process of (1-6) identification of a source of unpleasant noise will be explained next. In this process, a source of unpleasant noise is identified for each result of experiment that is carried out for the three modes of the color mode (1), the color mode (2), and the monochrome mode. FIG. 13 to FIG. 27 are graphs each of which expresses a relationship between the standard (emphasis, original sound, and damping) of each sound source shown in Table 2 to Table 4 and subjective evaluation values. The ordinate of the graph represents the subjective evaluation value α. When the evaluation value is higher, this means that the sound is unpleasant. The abscissa of the graph represents a standard of the sound source, that is, a standard of the sound pressure level. "−1" represents damping of the sound source, "0" represents the original sound, and "+1" represents emphasis of the sound source.

Figure 13:
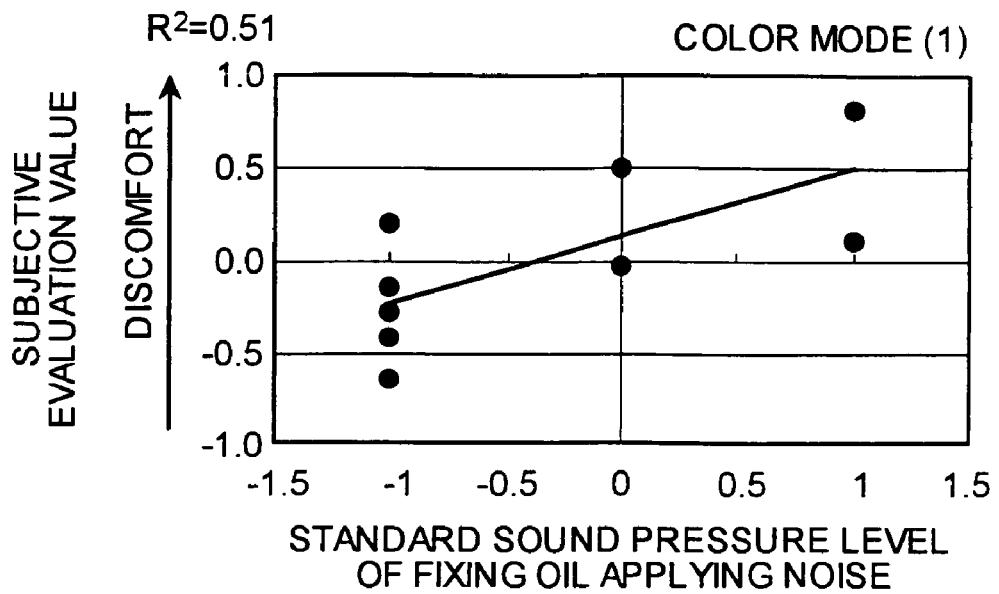
FIG. 13 is a graph of a relationship between a sound pressure level of a sound of applying a fixing oil and a subjective evaluation value in color mode (1)
Figure 14:
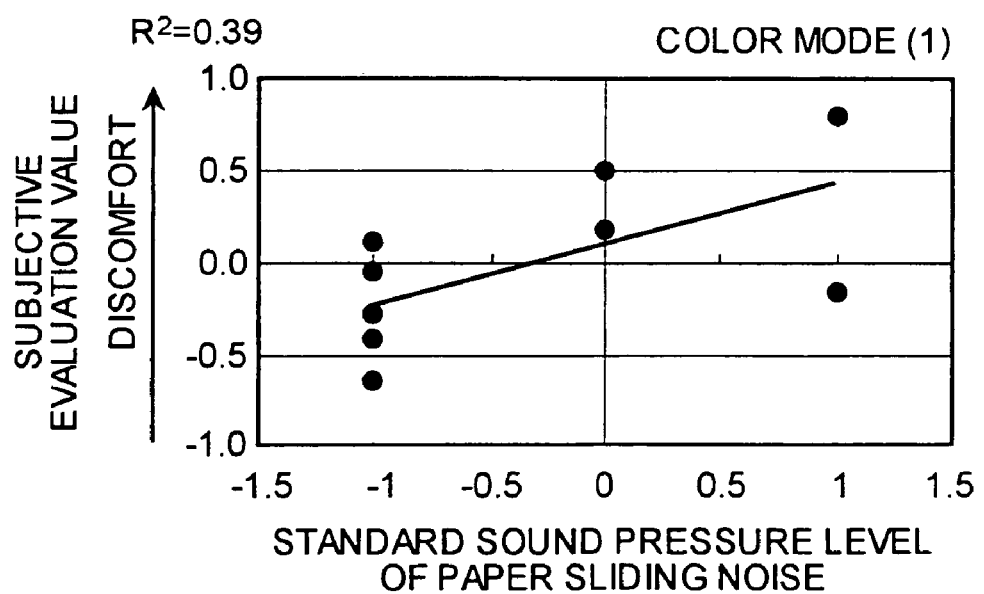
FIG. 14 is a graph of a relationship between a sound pressure level of a paper sliding noise and a subjective evaluation value in color mode (1)
Figure 15:
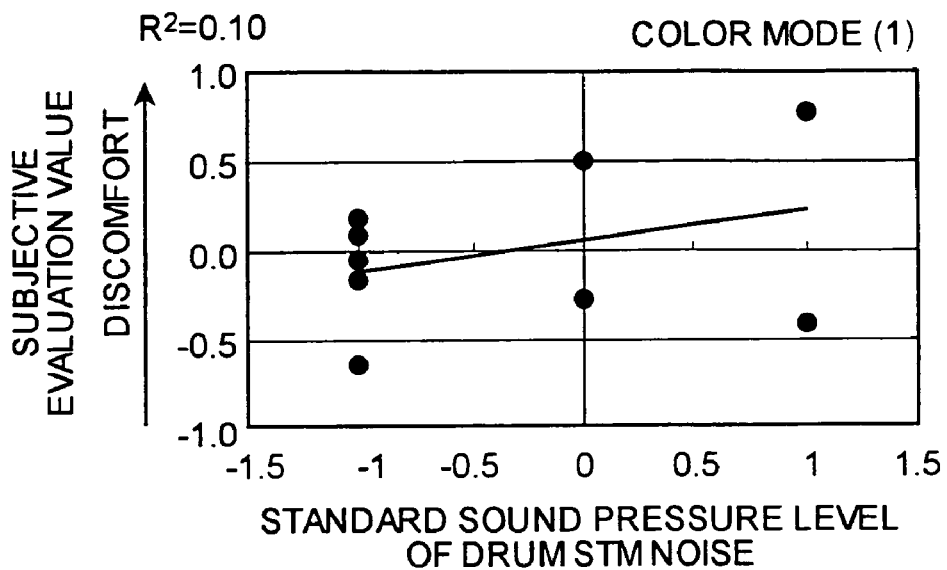
FIG. 15 is a graph of a relationship between a sound pressure level of a drum STM noise and a subjective evaluation value in color mode (1)
Figure 16:
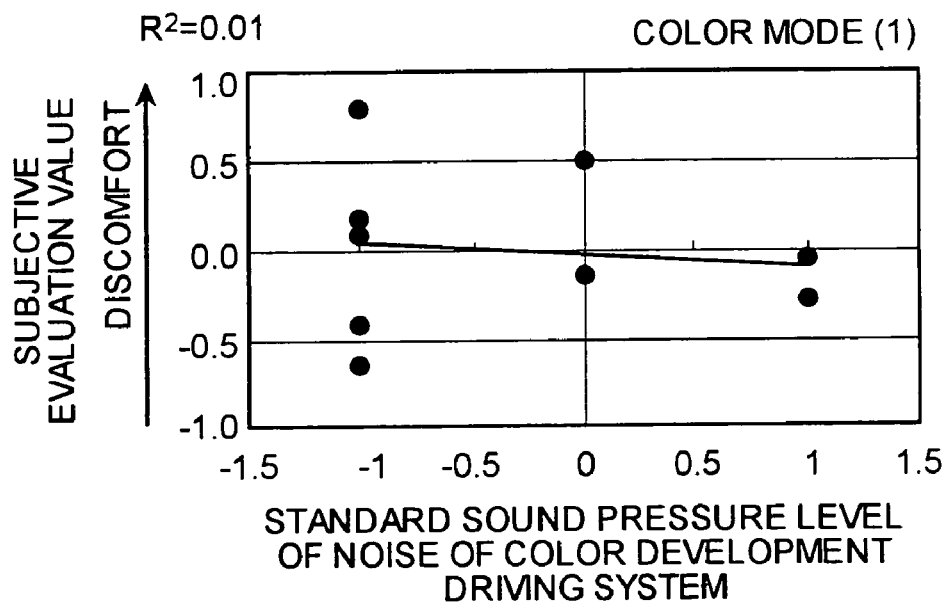
FIG. 16 is a graph of a relationship between a sound pressure level of a sound of driving a color development and a subjective evaluation value in color mode (1)
Figure 17:
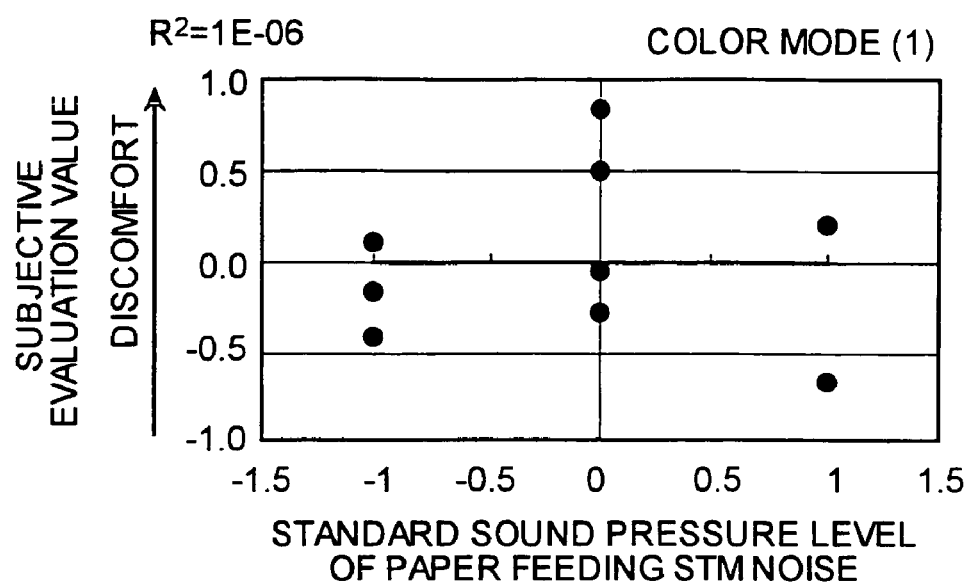
FIG. 17 is a graph of a relationship between a sound pressure level of a paper feeding STM noise and a subjective evaluation value in color mode (1)
Figure 18:
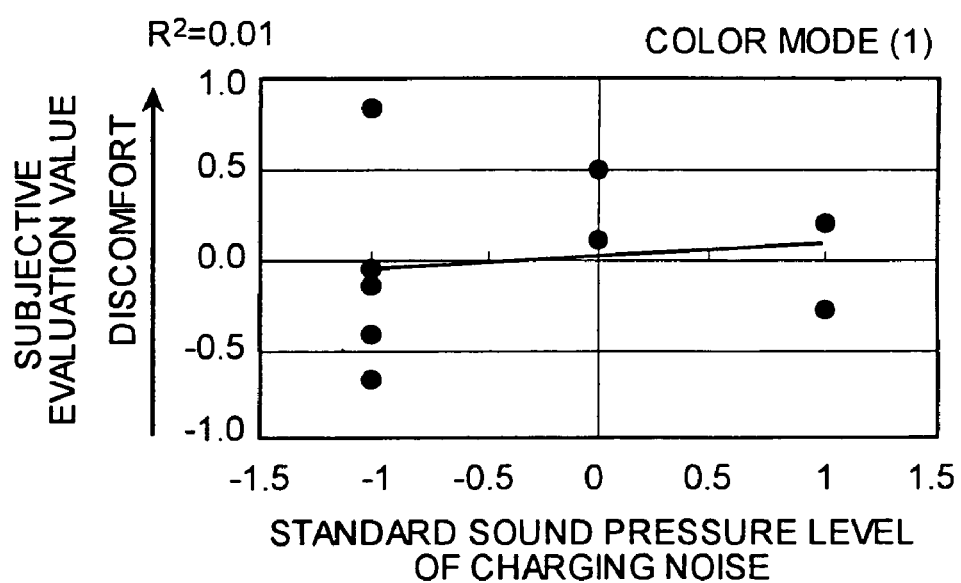
FIG. 18 is a graph of a relationship between a sound pressure level of a charging noise and a subjective evaluation value in color mode (1)
Figure 19:
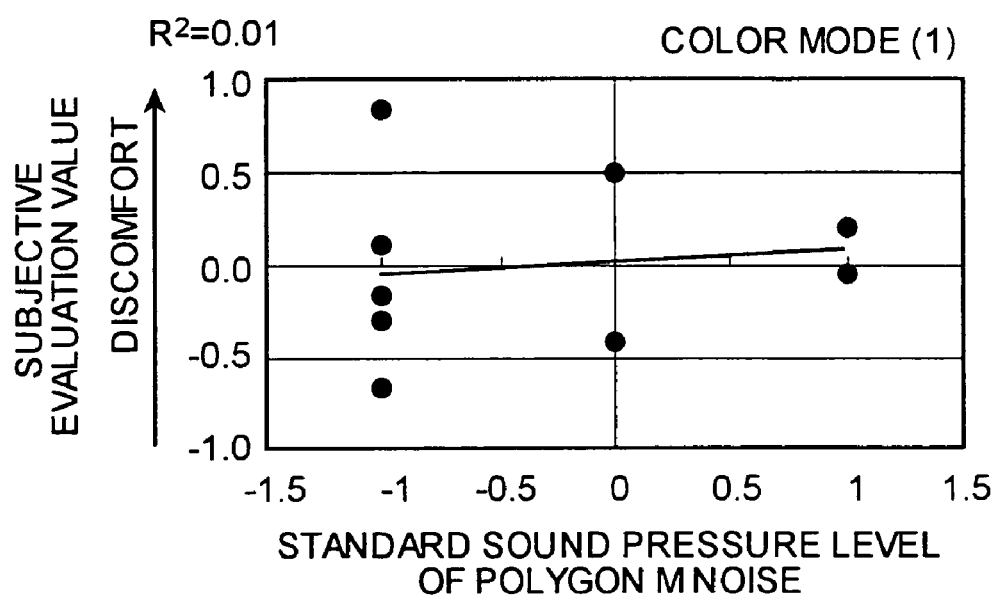
FIG. 19 is a graph of a relationship between a sound pressure level of a polygon M noise and a subjective evaluation value in color mode (1)
Figure 22:
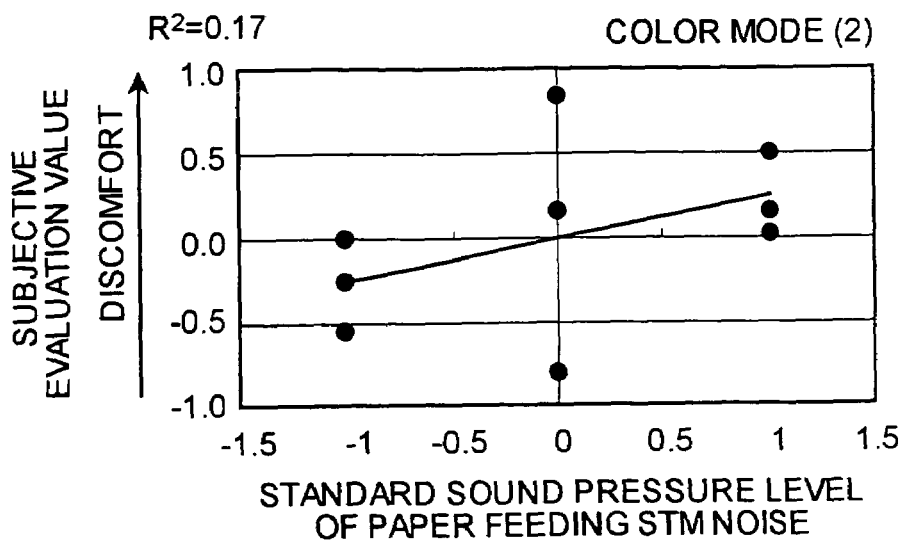
FIG. 22 is a graph of a relationship between a sound pressure level of a paper feeding STM noise and a subjective evaluation value in color mode (2)
Figure 23:
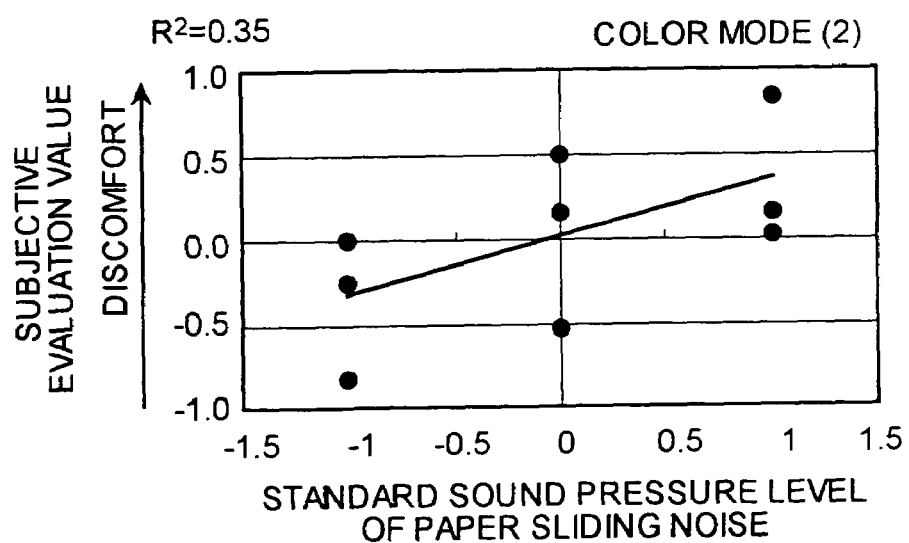
FIG. 23 is a graph of a relationship between a sound pressure level of a paper sliding noise and a subjective evaluation value in color mode (2)
Figure 26:
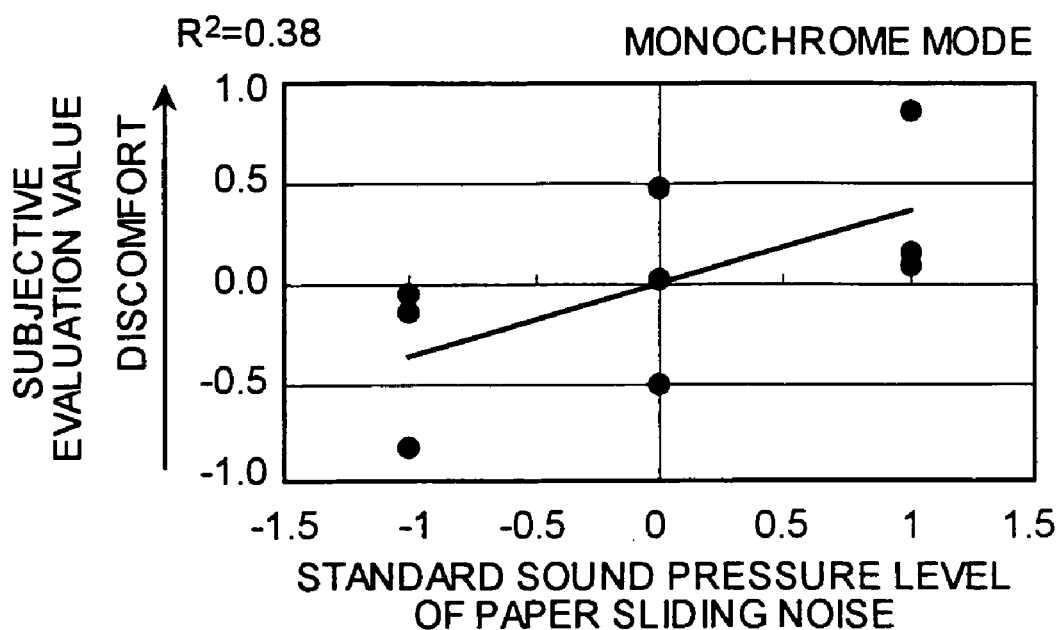
FIG. 26 is a graph of a relationship between a sound pressure level of a paper sliding noise and a subjective evaluation value in monochrome mode.
Figure 27:
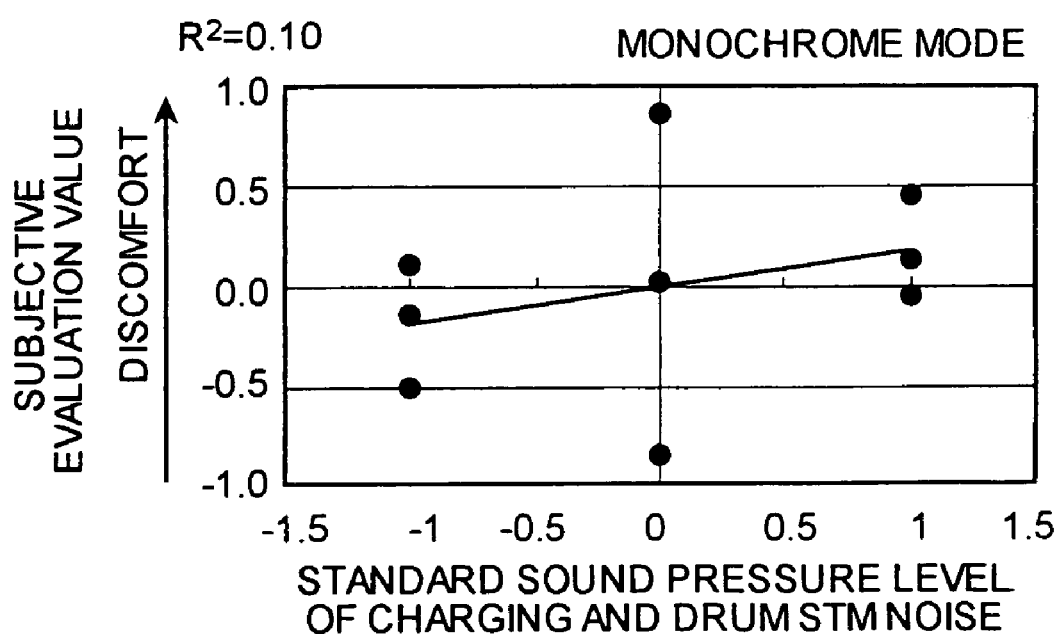
FIG. 27 is a graph of a relationship between a sound pressure level of charging and drum STM noises and a subjective evaluation value in monochrome mode.

In each drawing, "$R^2$" represents a contribution rate, and "R" represents a correlation function. The contribution rate indicates a percentage of the contribution of the sound source to the discomfort. The $R^2$ shown in FIG. 13 represents that the applying percussive noise of the fixing oil contributes 51 percent to the discomfort. In other words, when the change in the level of the sound source and the change in the subjective evaluation value (i.e., discomfort) have a high correlation, the contribution rate becomes large. A sum of the contribution rates of each sound source becomes 100 percent in one mode. However, the sum may not be exactly 100 percent because of rounding of the scores.

When the contribution rate of each sound source in the color mode (1) shown in FIG. 13 to FIG. 19 is referred to, it is clear that the noise of the color development driving system, the noise of the paper feeding stepping motor, the charging noise, and the noise of the polygon mirror motor make little contribution to the discomfort. However, in the later analysis, it is clear that the three sound sources of the noise of the paper feeding stepping motor, the charging noise, and the noise of the polygon mirror motor have a strong relationship with the tonality (i.e., pure tone) component. It is also clear that although these three sound sources are actually unpleasant, the discomfort cannot be improved unless countermeasures are taken simultaneously to these sound sources when the frequency of the pure tone is close. Therefore, in other modes, these sound sources are set to the same standard for each sample sound (refer to the process of (3) and Table 3 and Table 4). As only the noise of the color development driving system makes little contribution to the discomfort among the sound sources, this sound is considered as not requiring a countermeasure. However, improvement may be necessary in the evaluation of the sound power level.

On the other hand, the applying percussive noise of the fixing oil contributes most to discomfort in the color mode (1). The paper sliding noise contributes next, to discomfort in the color mode (1).

According to a result of the analysis of the sources of unpleasant noise in the color mode (2) shown in FIG. 20 to FIG. 23, contribution rates of the sound sources are as follows: 43 percent from the applying percussive noise of the fixing oil; 35 percent from the paper sliding noise; 17 percent from the noise of the paper feeding stepping motor; and 3 percent from the total of the charging noise, the noise of the polygon mirror motor, and the noise of the drum drive stepping motor.

According to a result of the analysis of the sources of unpleasant noise in the monochrome mode shown in FIG. 24 to FIG. 27, contribution rates of the sound sources are as follows: 43 percent from the applying percussive noise of the fixing oil; 35 percent from the paper sliding noise; 10 percent from the total of the charging noise and the noise of the drum drive stepping motor; and 3 percent from the noise of the color development driving system.

It is clear from the above result of the analysis that the sound sources other than the noise of the development driving system contribute to discomfort, and that when countermeasures are taken against these sound sources, the discomfort can be reduced.

The process of (1-7) preparation of analysis data of a differential model will be explained next. In the present process, a difference between subjective evaluation values (i.e., scores) of two sounds is calculated, data of linear difference between psycho-acoustic parameters is created, and a multiple linear regression analysis of both values are carried out, using the results of the experiment obtained from the pair comparison experiment in the process of (1-5). The data of these differences are obtained as follows.

Assume that there are 35 testers who carry out the pair comparison experiment. When a tester evaluates that the sample sound (1) is unpleasant, after comparing sample noise (1) with sample noise (2), the tester gives "score 1", and when the tester evaluates that the sample sound (2) is unpleasant, the tester gives "score −1". Assume that two testers evaluate that the sample sound (1) is unpleasant, and 33 testers evaluate that the sample sound (2) is unpleasant. Then, a total of the scores becomes 2−33=−31. A value obtained by dividing −31 by the total number of testers 35 gives a difference "−0.886" of the subjective evaluation values (scores).

The difference between the subjective evaluation values and the difference between the psycho-acoustic parameters, that is, the difference of the psycho-acoustic parameter values (refer to Table 6) between the sample sound (1) and the sample sound (2) are calculated for all the combinations of the sample sounds (i.e., 72 combinations per one mode, and a total of 288 combinations for the four modes.

Table 7 expresses a part of the result of the calculated difference between the calculated scores and the difference between psycho-acoustic parameter values (analysis data of the differential model). Table 7 expresses a part of the result of the calculations for the sample sounds in the color mode (1).

The process of (1-8) deriving of an expression to estimate a difference between scores will be explained next. As explained above in the concept of the present inventor, in order to measure the subjective evaluation values (i.e., target variables) in high precision, it is effective to carry out a multiple linear regression analysis using a plurality of psycho-acoustic parameters (explanatory variables). In other words, a simple linear regression analysis is to estimate a target variable using a single explanatory variable, and may have low precision. However, as the multiple linear regression analysis is to estimate a target variable using a plurality of explanatory variable, the estimation precision is high, and the analysis is effective. Therefore, the multiple linear regression analysis is used in the present process.

The multiple linear regression analysis can be carried out using various kinds of spreadsheet software or statistical analysis software that are commercially available. For example, it is possible to use regression analysis of analysis tool of spreadsheet software "Excel (a registered trademark of Microsoft Corporation)", or statistical analysis software "JMP (a registered trademark of SAS Institute Inc.)", or "SPSS (a registered trademark of SPSS Inc.)". The data (i.e., a difference between the subjective evaluation values and a difference between psycho-acoustic parameters) in Table 7 are input to Excel or JMP, and analysis is carried out while selecting explanatory variable. Based on this analysis, statistical results such as P values of regression coefficients and selected explanatory coefficients, and contribution rates of expressions are output. The P value refers to a probability of a test of a significant difference. When the probability is 5 percent or less, the result is determined as significant. When the probability is 5 percent or more, the result is determined as insignificant (i.e., irrelevant).

By using the above software, differences of scores calculated in the process of (1-7) are set as target variables. Differences of psycho-acoustic parameters and differences of ppm values are set as explanatory variables. The multiple linear regression analysis is carried out based on the above assumption. In this multiple linear regression analysis, the scores are not used as target variables but the differences of the scores are used as target variables. Therefore, the intercept (i.e., a constant term) is set as zero. In the selection of variables, the psycho-acoustic parameter values of loudness, sharpness, tonality, and impulsiveness are selected. As a result of carrying out the multiple linear regression analysis, a scatter analysis table shown in Table 8 and a regression

TABLE 7

| Order of presentation I j | Difference of sound pressure level | Difference of loudness | Difference of sharpness | Difference of tonality | Difference of roughness | Difference of impulsiveness | Difference of relative approach | Total score | Number of testers | Difference of subjective evaluations |
|---|---|---|---|---|---|---|---|---|---|---|
| (1)–(2) | −5.70 | −1.95 | −0.42 | −0.01 | −0.24 | 0.05 | −0.15 | −31 | 35 | −0.886 |
| (2)–(1) | 5.70 | 1.95 | 0.42 | 0.01 | 0.24 | −0.05 | 0.15 | 19 | 35 | 0.543 |
| (1)–(3) | −1.80 | −1.37 | −0.76 | 0.08 | −0.31 | −0.04 | −0.19 | −19 | 35 | −0.543 |
| (3)–(1) | 1.80 | 1.37 | 0.76 | −0.08 | 0.31 | 0.04 | 0.19 | 11 | 35 | 0.314 |
| (1)–(4) | −2.85 | −0.90 | 0.21 | −0.01 | −0.07 | 0.04 | −0.09 | −15 | 35 | −0.429 |
| (4)–(1) | 2.85 | 0.90 | −0.21 | 0.01 | 0.07 | −0.04 | 0.09 | 15 | 35 | 0.429 |
| (1)–(5) | −3.50 | −1.04 | 0.14 | 0.04 | −0.36 | −0.21 | −0.23 | −19 | 35 | −0.543 |
| (5)–(1) | 3.50 | 1.04 | −0.14 | −0.04 | 0.36 | 0.21 | 0.23 | 13 | 35 | 0.371 |
| (1)–(6) | −3.55 | −0.38 | 0.01 | 0.07 | −0.43 | −0.37 | −0.24 | −19 | 35 | −0.543 |
| (6)–(1) | 3.55 | 0.38 | −0.01 | −0.07 | 0.43 | 0.37 | 0.24 | 13 | 35 | 0.371 | analysis result shown in Table 9 are obtained. As the ppm values have a high correlation with the loudness values, the ppm values are not selected.

TABLE 8

| Cause | Degree of freedom | Sum of squares | Average square | F value |
|---|---|---|---|---|
| Regression | 4 | 118.4123 | 29.6031 | 404.3466 |
| Error | 284 | 20.79225 | 0.0732 | p value (Prob > F) |
| Total | 288 | 139.2046 | | <.0001 |

TABLE 9

| Item | Partial regression coefficient | Standard error | t value | p value (Prob > \|t\|) | Lower limit 95 percent | Upper limit 95 percent |
|---|---|---|---|---|---|---|
| Intercept (0 constraint) | 0 | 0 | | | 0 | 0 |
| Loudness | 0.2347697 | 0.01063 | 22.8 | <.0001 | 0.213845 | 0.255694 |
| Sharpness | 0.3847411 | 0.029918 | 12.86 | <.0001 | 0.325852 | 0.443631 |
| Tonality | 2.6283418 | 0.294076 | 8.94 | <.0001 | 2.049496 | 3.207187 |
| Impulsiveness | 1.5681529 | 0.071256 | 22.01 | <.0001 | 1.427895 | 1.708411 |

The contribution rate is obtained as sum of squares/total sum of squares. Therefore, from the result shown in Table 8, the contribution rate is obtained as 118.4123/139.2046=0.85. In other words, it is clear that the selected four parameters including loudness, sharpness, tonality, and impulsiveness contribute 85 percent to discomfort.

As shown in Table 9, the regression analysis result includes an upper limit value and a lower limit value of partial regression coefficients having reliability of 95 percent or above (i.e., a range of partial regression coefficients having reliability of 95 percent or above), in addition to partial regression coefficients (i.e., regression coefficients in the multiple linear regression analysis) of the selected four parameters. The upper limit value and lower limit value are obtained by adding or subtracting a value of about two times a standard deviation (i.e., $2\hat{\sigma}$) to or from each corresponding estimate value of the partial regression coefficients. Each partial regression coefficient has a positive value. Therefore, it is clear that when a difference between parameter values becomes larger toward the plus direction, a difference between discomforts becomes larger.

A result of the multiple linear regression analysis is expressed as a model expression (A) of difference as follows.

$$\alpha i - \alpha j = +0.2347697 \times (x \text{ loudness } i - x \text{ loudness } j) + \quad (A)$$
$$0.3847411 \times (x \text{ sharpness } i - x \text{ sharpness } j) +$$
$$2.6283418 \times (x \text{ tonality } i - x \text{ tonality } j) +$$
$$1.5681529 \times$$
$$(x \text{ impulsiveness } i - x \text{ impulsiveness } j)$$

$\alpha n$ (n=1, 2, ... i, ... j, ... n): A subjective evaluation value (i.e., score) of discomfort of sound The linear expression capable of calculating a difference between discomfort levels (i.e., score) is derived by substituting the two psycho-acoustic parameter values as shown above.

Figure 28:
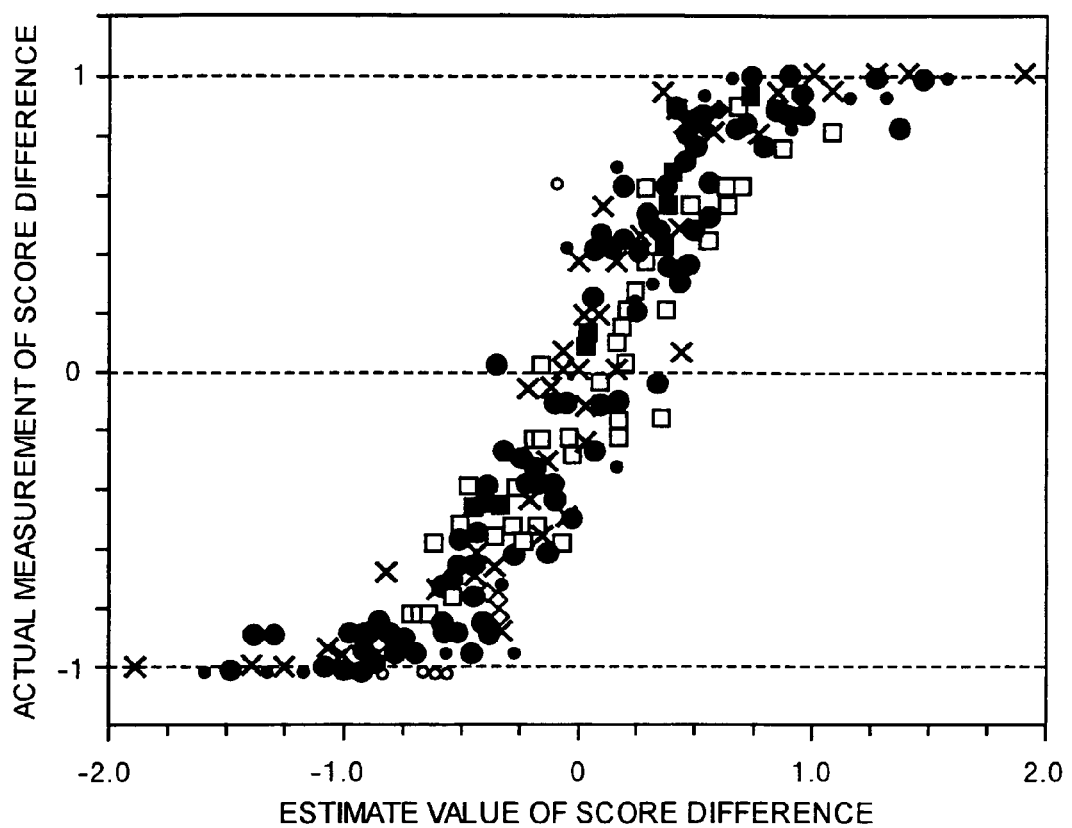
FIG. 28 is a plot of a relationship between an estimate value of a difference between scores derived from a linear expression capable of calculating a difference between discomforts (i.e., scores) obtained, and an actual measurement, in one process according to the present invention.

FIG. 28 is a plot of a relationship between an actual measurement and an estimate value of a difference between scores derived from the linear expression (A). From FIG. 28, it is clear that although the actual measurements of a difference between scores can take a range from −1 to 1, the estimate values can take a range from about −2 to 2.

The process of (1-9) deriving a sound quality evaluation expression to estimate scores will be explained next.

While the above expression (A) can derive an estimate value of a difference between scores, what is finally necessary in the sound quality evaluation is the score itself. A sound quality evaluation expression capable of estimating a score from the model of a difference between scores is derived as follows.

First, an average of each sample sound that is used in the experiment is substituted into the expression (A) as each psycho-acoustic parameter. Discomfort when α0=0, that is, when each parameter value is an average is defined as "0", thereby obtaining an intercept.

In other words, the average of the sample sound (refer to Table. 6) used in the experiment is substituted into the expression (A), by assuming that the effect α0 of the coordinate of the center is 0, x loudness is 0, x sharpness is 0, x tonality is 0, and x impulsiveness is 0, in this case respectively.

The average of each psycho-acoustic parameter is substituted into the expression (A);

$$\alpha i - \alpha 0 = +0.2347697 \, (x \text{ loudness } i - x \text{ loudness } 0) +$$
$$0.3847411 \times (x \text{ sharpness } i - x \text{ sharpness } 0) +$$
$$2.6283418 \times (x \text{ tonality } i - x \text{ tonality } 0) +$$
$$1.5681529 \times$$
$$(x \text{ impulsiveness } i - x \text{ impulsiveness } 0)$$

to obtain:

$$\alpha i = 0.2347697 \times \text{loudness } i + 0.3847411 \times$$
$$\text{sharpness } i + 2.6283418 \times \text{tonality } i +$$
$$1.5681529 \times \text{impulsiveness } i - 3.790295483.$$

This αi is defined as a discomfort index S of sound as follows.

$$S = 0.2347697 \times \text{loudness } i + 0.3847411 \times \text{sharpness } i +$$
$$1.5681529 \times \text{impulsiveness } i - 3.790295483$$

From the above expression, it is clear that discomfort can be decreased when the sound element corresponding to each psycho-acoustic parameter is decreased, that is, when (1) the loudness is made smaller, (2) the higher-frequency component (sharpness) is decreased, (3) the pure tone component (tonality) is decreased, and (4) the impulse noise (impulsiveness) is decreased.

As explained in the process of (1-8), the partial regression coefficients have reliability of 95 percent or above that is obtained as a result of the regression analysis shown in Table 9. Therefore, a range of the intercept is also obtained by substituting the upper limit value and the lower limit value of each partial regression coefficient (i.e., the intercept when the upper limit value is substituted is −4.224266, and the intercept when the lower limit value is substituted is −3.356324).

When the above expression is modified to take coefficients and an intercept within the above range, the following expression (a) is obtained.

$$S = A \times (\text{loudness}) + B \times (\text{sharpness}) + C \times (\text{tonality}) + D \times (\text{impulsiveness}) + E$$

Ranges of regression coefficients of parameters $$0.213845 \leq A \leq 0.255694$$

$$0.325852 \leq B \leq 0.443631$$

$$2.049496 \leq C \leq 3.207187$$

$$1.427895 \leq D \leq 1.70841$$

$$-4.224266 \leq E \leq -3.356324 \quad (a)$$

The process of (1-10) verification of a derived sound quality evaluation expression will be explained next. In this process, the estimation precision of the estimation expression (i.e., a sound quality evaluation expression) of scores derived above is verified.

Figure 29:
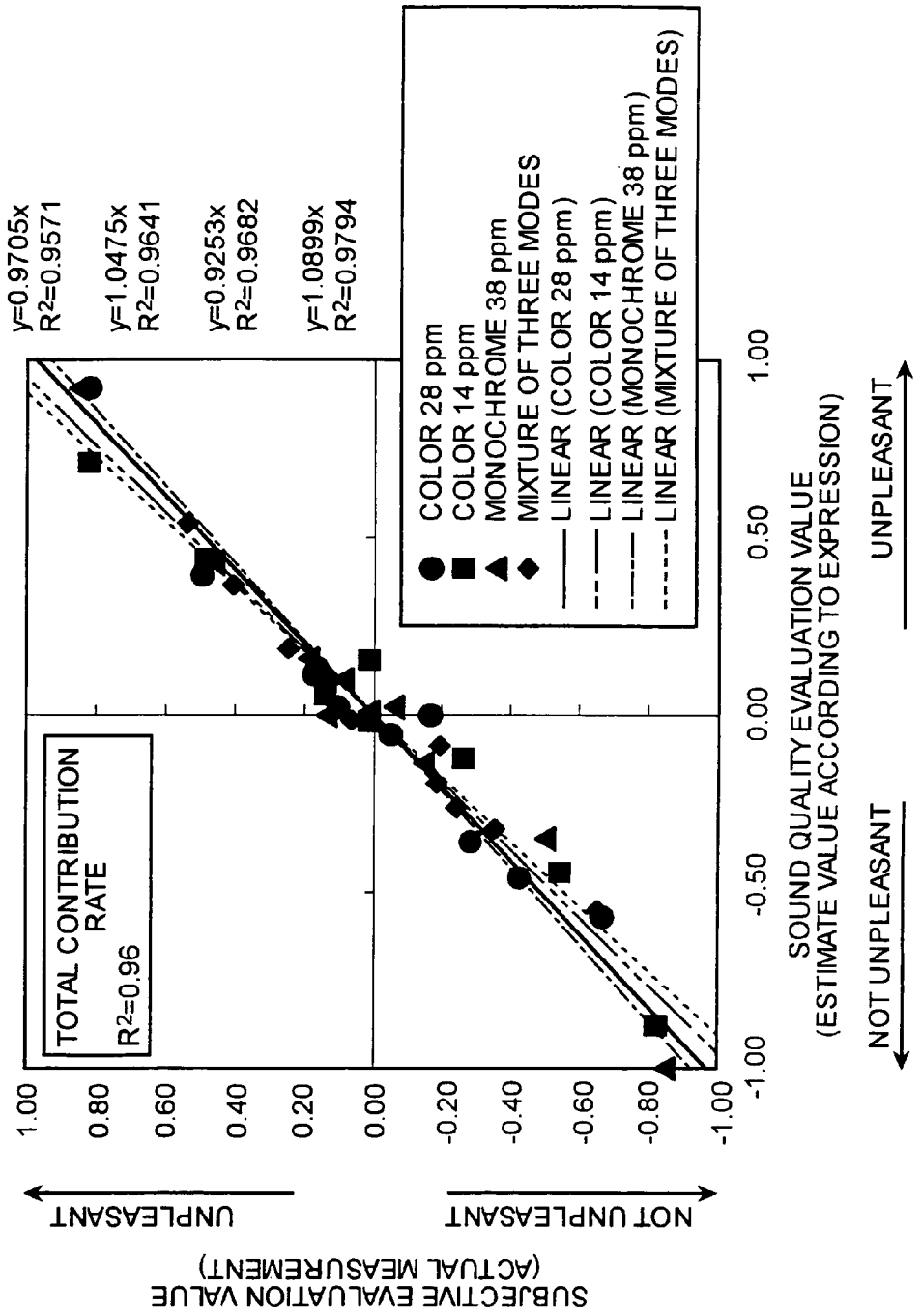
FIG. 29 is a plot of a comparison between an estimate value derived from a sound quality evaluation expression according to the present invention and an actual measurement, in each operation mode of the image forming apparatus.

FIG. 29 is a plot of a comparison between an estimate value (as expressed in the abscissa) derived from the sound quality evaluation expression (a) and an actual measurement value (as expressed in the ordinate), for each operation mode of the color mode (1), the color mode (2), the monochrome mode, and the mixed mode, in the four experiments. As shown in FIG. 29, the inclination of the graph is approximately 1, and the contribution rate is 96 percent which is larger than 95 percent. Therefore, the precision of the estimate values of scores derived from the expression (a) is considered to be high in each of the four experiments, that is, the four modes. In the estimate value of a difference between scores shown in FIG. 28, a deviation of this value from the actual measurement is observed near "1" and "−1" as the difference between scores. However, from the result shown in FIG. 29, the precision of the estimate values of scores derived from the expression (a) is considered to be improved. This is considered because the variation of 36 plots of the estimate values is averaged in the expression (A), while 288 estimate values are plotted in the expression of deriving the difference between scores.

Actually, an intercept (i.e., a constant term) is set for each of the four experiments. This is because a relative original point (i.e., a center) is adjusted in each experiment at the time of obtaining a score (a subjective evaluation value=an actually measured value). The constant term is necessary because the calculation is carried out by setting a constraint to make the sum of the score zero in each experiment. In other words, while in the above process of (9), the intercept is obtained by substituting the average of loudness, sharpness, tonality, and impulsiveness of the sample sound used in the experiment, the averages are different between the four experiments (refer to Table 6). For example, while the average of loudness in the color mode (1) is 6.59 (sone), the average of loudness in the color mode (2) is 5.70 (sone).

The estimate values plotted in the graph shown in FIG. 29 are obtained by substituting the averages in each experiment as described above.

On the other hand, the expression (A) derived this time has no constraint that the sum of scores of the sample sound must be zero. Instead of this, attention needs to be focused on coincidence of inclinations of the expression. Therefore, in order to obtain the graph shown in FIG. 29, it is not necessary to carry out the adjustment to substitute the averages in each experiment. The adjustment is carried out to obtain the graph shown in FIG. 29 because it is necessary to verify the precision of the estimate value by comparing the actual measurement with the estimate value in each experiment. Table 10 expresses the adjustment values for reference. When a value of a "difference from a total average" is added to a value of the intercept obtained by substituting the average in each mode, an expression similar to the expression (A) is obtained.

TABLE 10

|  | Loudness | Sharpness | Tonality | Impulsiveness | PPM | Intercept | Difference from total average |
|---|---|---|---|---|---|---|---|
| Total average | 7.07 | 2.28 | 0.12 | 0.61 | 26.7 | −3.790 | 0.000 |
| Color 28 ppm average | 6.59 | 2.12 | 0.11 | 0.53 | 28.0 | −3.493 | −0.297 |
| Color 14 ppm average | 5.70 | 2.25 | 0.16 | 0.64 | 14.0 | −3.620 | −0.171 |
| Monochrome 38 ppm average | 8.46 | 2.42 | 0.07 | 0.61 | 38.0 | −4.110 | 0.319 |
| Three-mode mixed average | 7.52 | 2.33 | 0.12 | 0.62 | 26.7 | −3.954 | 0.164 |

The estimate value (i.e., score) obtained from the expression (A) derived above is considered to have high precision. It is necessary to confirm at what level of the discomfort index S of the obtained evaluation a person feels the sound unpleasant. The following experiment is carried out to confirm this. After each tester hears all the sample sounds (1) to (9), the tester hears each sound again one by one and evaluates discomfort of each sample sound at three stages. Table 11, Table 12, and Table 13 express results obtained from this experiment. Table 11 expresses the result of the experiment carried out for the sample sound in the color mode (1). Table 12 expresses the result of the experiment carried out for the sample sound in the color mode (2). Table 13 expresses the result of the experiment carried out for the sample sound in the monochrome mode.

TABLE 11

| Sample sound | Actual measurement subjective evaluation value | Sound quality evaluation value considering difference from total average | Sound quality evaluation value according to expression (A) | Score |
|---|---|---|---|---|
| Color 28 ppm (8) | 0.810 | 0.923 | 0.622 | C |
| Color 28 ppm (9) | 0.492 | 0.395 | 0.093 | C |
| Color 28 ppm (2) | 0.178 | 0.115 | −0.186 | C |
| Color 28 ppm (6) | 0.098 | 0.022 | −0.279 | B |
| Color 28 ppm (5) | −0.048 | −0.057 | −0.358 | B |
| Color 28 ppm (3) | −0.162 | −0.006 | −0.307 | A |
| Color 28 ppm (4) | −0.286 | −0.361 | −0.661 | A |
| Color 28 ppm (1) | −03419 | −0.461 | −0.761 | A |
| Color 28 ppm (7) | −0.663 | −0.570 | −0.870 | A |

TABLE 12

| Sample sound | Actual measurement subjective evaluation value | Sound quality evaluation value considering difference from total average | Sound quality evaluation value according to expression (A) | Score |
|---|---|---|---|---|
| Color 14 ppm (4) | 0.819 | 0.717 | 0.542 | C |
| Color 14 ppm (5) | 0.489 | 0.440 | 0.263 | C |
| Color 14 ppm (8) | 0.149 | 0.109 | −0.066 | C |
| Color 14 ppm (1) | 0.140 | 0.055 | −0.120 | C |
| Color 14 ppm (2) | 0.013 | 0.155 | −0.020 | C |
| Color 14 ppm (3) | 0.013 | −0.021 | −0.194 | B |
| Color 14 ppm (6) | −0.263 | −0.122 | −0.296 | B |
| Color 14 ppm (9) | −0.540 | −0.450 | −0.624 | A |
| Color 14 ppm (7) | −0.819 | −0.883 | −1.056 | A |

TABLE 13

| Sample sound | Actual measurement subjective evaluation value | Sound quality evaluation value considering difference from total average | Sound quality evaluation value according to expression (A) | Score |
|---|---|---|---|---|
| Monochrome 38 ppm (4) | 0.847 | 0.928 | 1.242 | C |
| Monochrome 38 ppm (5) | 0.458 | 0.428 | 0.743 | C |
| Monochrome 38 ppm (8) | 0.128 | 0.005 | 0.320 | C |
| Monochrome 38 ppm (1) | 0.087 | 0.094 | 0.409 | C |
| Monochrome 38 ppm (2) | 0.010 | 0.011 | 0.326 | B |
| Monochrome 38 ppm (3) | −0.052 | 0.018 | 0.333 | B |
| Monochrome 38 ppm (6) | −0.142 | −0.142 | 0.173 | B |
| Monochrome 38 ppm (9) | −0.500 | −0.351 | −0.036 | A |
| Monochrome 38 ppm (7) | −0.837 | −0.990 | −03674 | A |

In the tables, "A" represents an evaluation that the sound is permissible. "C" represents an evaluation that the sound is not permissible. "B" represents an evaluation that the sound is between permissible and not permissible. When a largest value among the sound quality evaluation values that are evaluated as "A" (i.e., values calculated by the expression (A)) is a tolerance, a tolerance for each ppm and for each image forming speed (mm/s) in each mode is obtained as shown in Table 14.

TABLE 14

| ppm | Image forming speed V (mm/s) | Tolerance |
|---|---|---|
| Color 14 ppm | 62.5 | −0.624 |
| Color 28 ppm | 125.0 | −0.307 |
| Monochrome 38 ppm | 185.0 | −0.036 |

Figure 30:
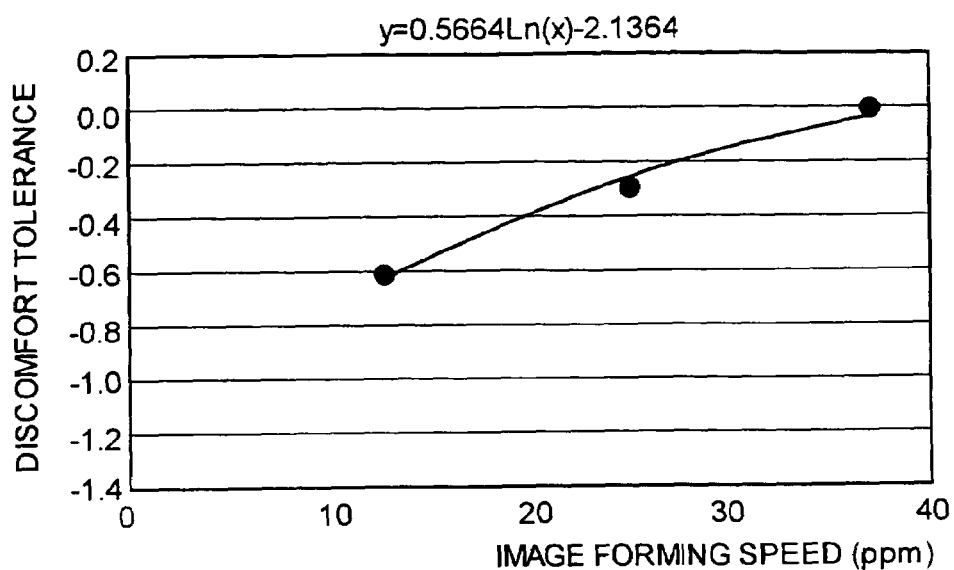
FIG. 30 is a graph that expresses a relationship between an image forming speed in pages-per-minute (ppm) value obtained from a result of an experiment and a tolerance of an index derived from the sound quality evaluation expression.

FIG. 30 is a graph of an approximate relationship between a ppm value and a tolerance based on the result shown in Table 14. The approximate expression is as follows.

$$S \leq 0.5664 \text{Ln}(\text{ppm}) - 2.1364 \quad (b)$$

When a tolerance is calculated for each 10 ppm from the approximate expression (b), a result shown in Table 15 is obtained.

TABLE 15

| ppm | Tolerance |
| --- | --- |
| 10 | −0.832 |
| 20 | −0.440 |
| 30 | −0.210 |
| 40 | −0.047 |

Figure 31:
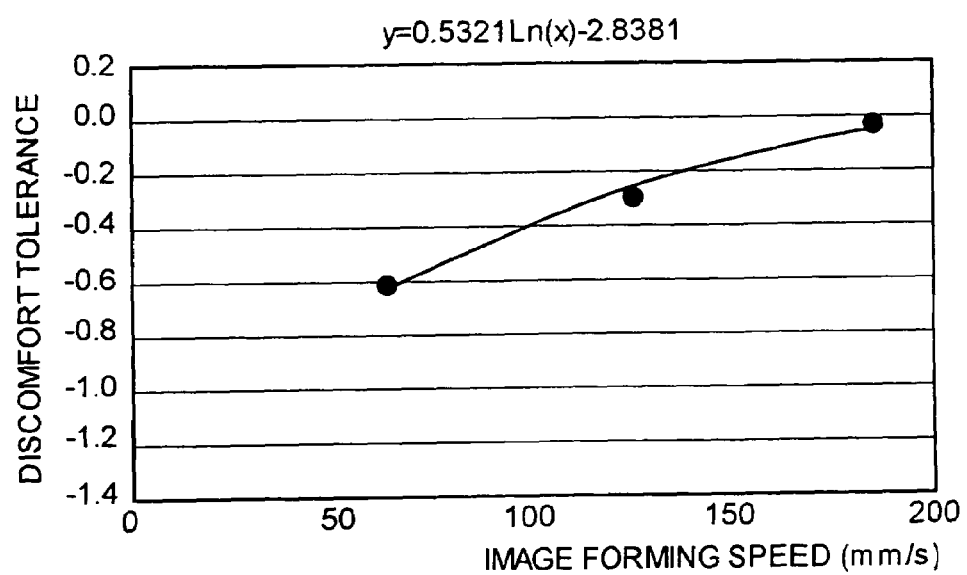
FIG. 31 is a graph of a relationship between the image forming speed in mm/s obtained from a result of an experiment and a tolerance of an index derived from the sound quality evaluation expression.

FIG. 31 is a graph of an approximate relationship between an image forming speed (mm/s) and a tolerance based on the results shown in Table 14. The approximate expression is as follows.

$$S \leq 0.5321 \text{Ln}(\text{mm/s}) - 2.8381 \quad (d)$$

A tolerance for each image forming speed of 40 mm/s is calculated from this approximate expression (d), as shown in Table 16.

TABLE 16

| Image forming speed V (mm/s) | Tolerance |
| --- | --- |
| 60 | −0.659 |
| 100 | −0.388 |
| 140 | −0.209 |
| 180 | −0.075 |
| 220 | 0.032 |

As shown in Table 15 and Table 16, when the discomfort index S calculated based on the sound generated when the apparatus operates at each speed (i.e., ppm, or image forming speed of mm/s) is at or below a tolerance, discomfort is barely felt.

As explained above, when the expression (A) or (a) is used, the discomfort index S can be obtained as the evaluation of discomfort by only obtaining psycho-acoustic parameter values that can be derived from the physical quantity of sound, without actually carrying out a subjective evaluation experiment. From the expression (b) or (d), a level of the discomfort index S at which discomfort is not felt can be determined in each mode, even if the apparatus has a plurality of operation modes having different image forming speeds (mm/s or ppm).

The above explains about the method of evaluating the quality of sound generated from the image forming apparatus and the method of deriving the sound quality evaluation expression that is used to evaluate the sound quality.

As explained above, the present invention provides the modifying method of evaluating noise that the image forming apparatus generates, and decreasing discomfort that the noise gives to a person based on a result of the evaluation. A detailed example of modifying the image forming apparatus having the above configuration and a countermeasure of decreasing discomfort that the sound generated from the image forming apparatus gives to a person will be explained.

First, sound generated from the image forming apparatus is collected according to a method similar to that used in the process (1-1), in order to evaluate the sound generated from the image forming apparatus. Sound is collected at a position where a person is present nearby (see FIG. 9) as prescribed in the ISO7779. This position is at a distance of 1.00±0.03 meters from a projection of a horizontal plane of a reference box, at a height of 1.2±0.03 meters or 1.50±0.03 meters from the floor.

Figure 9:
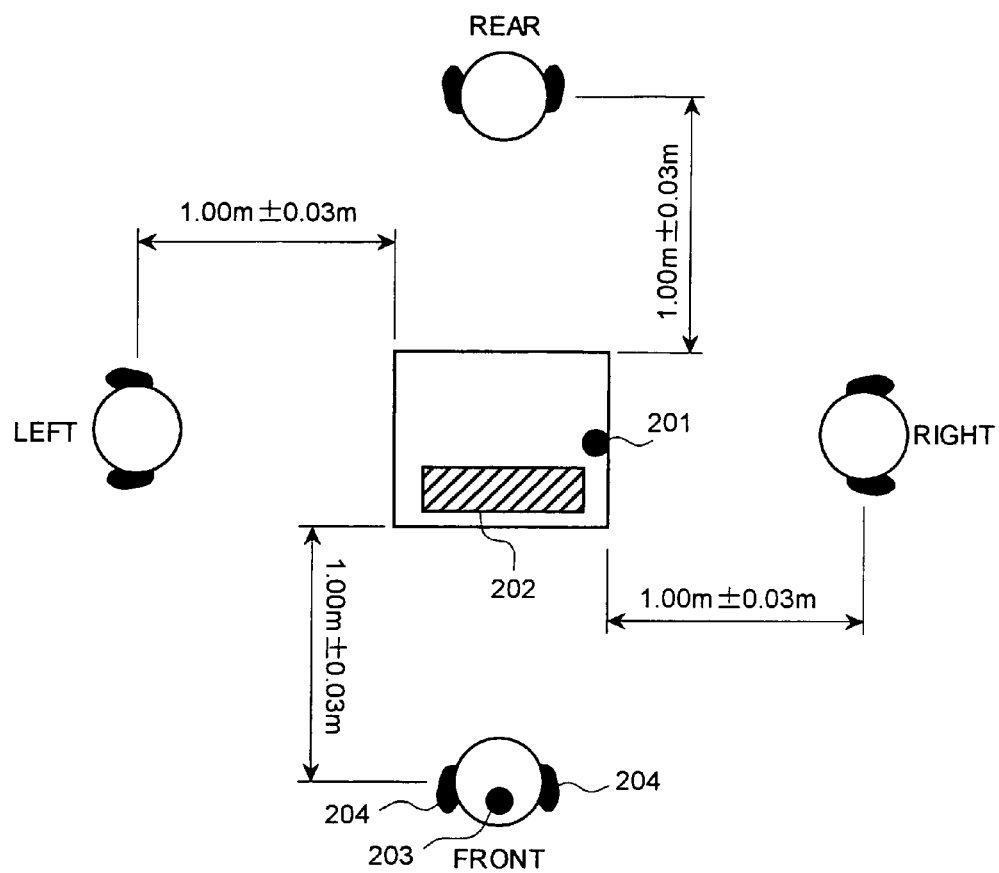
FIG. 9 is a schematic diagram for illustrating a measurement condition for measuring sound generated from the image forming apparatus to obtain a sound quality evaluation expression.

Further, as shown in FIG. 9, sounds may be collected from all the four sides of the front surface, the left and right surfaces, and the back surface of the operation unit. Psycho-acoustic parameters are obtained from each result of collection, and the discomfort index S is obtained from the sound quality evaluation expression. Then, it is determined whether the discomfort index S on each surface is within a tolerance. Alternatively, the discomfort index S may be obtained from a result of the collection of sound from only the front surface or any one surface, and a decision is made. Alternatively, an average of psycho-acoustic parameter values obtained from the sounds collected from the four sides may be derived. Then, it is determined whether the discomfort index S obtained from this average is within a tolerance.

In order to enable all persons at the four surface sides to feel no discomfort, it is preferable to collect sounds at all positions of the four surface sides. A noise countermeasure for only one surface can also be taken. In the case of collecting sound at only one surface side, the collection of sound at the front surface side that has a high possibility of presence of a person can provide a sufficient evaluation.

The index S may be derived from sounds collected from the four directions of the image forming apparatus, and the average of the indices may be used. This arrangement can provide an effect of suppressing the discomfort of operation noise to an average level given to a user regardless of a direction in which the user is present.

When the discomfort index S obtained in the above method exceeds the tolerance, there is a high risk that a person feels unpleasant. Therefore, in this case, various kinds of modifying are provided to units of the apparatus so as to make the discomfort index S equal to or smaller than the tolerance. On the other hand, when the discomfort index S is equal to or smaller than the tolerance, there is a small risk that a person feels unpleasant. Therefore, in this case, it can be determined that a noise countermeasure is not particularly necessary.

As described above, the discomfort index S can be made smaller by making loudness smaller, decreasing the high-frequency component (sharpness), decreasing the pure tone component (tonality), and decreasing impulse noise (impulsiveness). When the discomfort index S is made smaller, discomfort that is given to a person can be decreased. Therefore, a detailed example of a measure to decrease the psycho-acoustic parameters will be explained.

First, the measure to decrease tonality (i.e., pure tone component) will be explained.

As a measure to decrease tonality, there is a method of decreasing the noise of the drum drive stepping motor. As shown in FIG. 10, FIG. 11, and FIG. 12, the drum drive stepping motor generates noise in all the operation modes. This noise includes many frequency components of an input pulse to the stepping motor.

Figure 32:
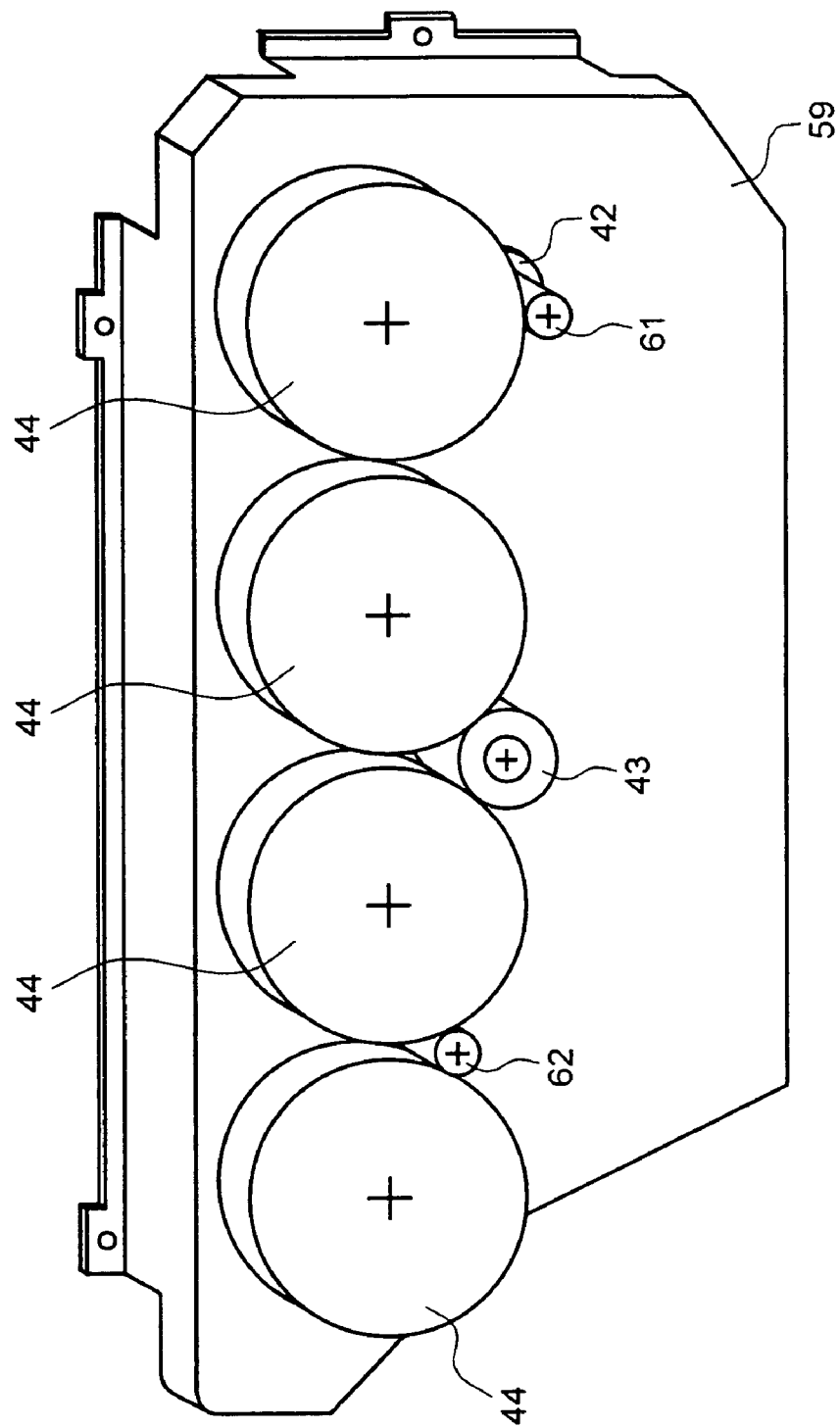
FIG. 32 is a schematic diagram of a photosensitive drum driving mechanism before a modification for illustrating an example of a modifying method according to the present invention.
Figure 33:
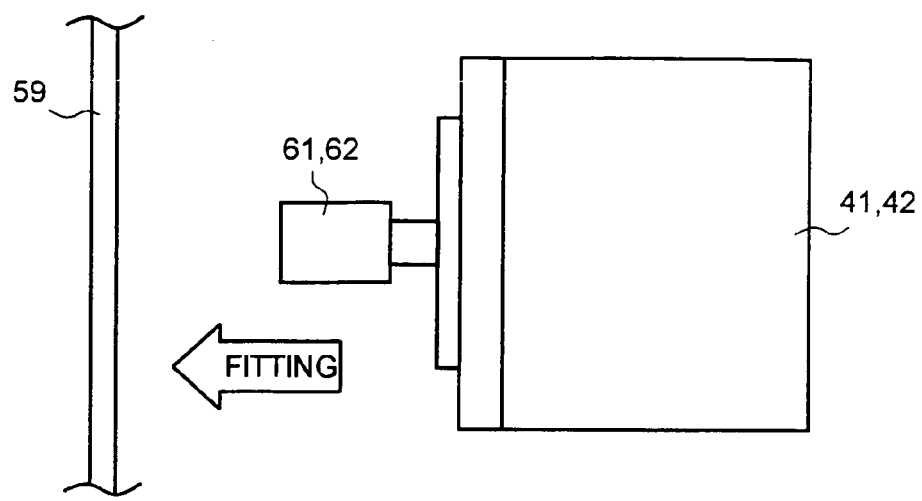
FIG. 33 is a schematic diagram for illustrating an installation of a driving motor that drives the photosensitive drum before a modification.

FIG. 32 and FIG. 33 are schematic diagrams of a drum driving mechanism including the color drum driving motor 41 and the black drum driving motor 42 before modifying. As shown in FIG. 32 and FIG. 33, the color drum driving motor 41, the black drum driving motor 42, and the gears 43 and 44 are held by a motor bracket 59.

The motor bracket 59 is a member having strength by pressing a sheet metal. This member is provided with a fitting unit (i.e., screw holes) by bending to fix this member to the casing of the image forming apparatus. The motor bracket 59 is fixed to the casing at this fitting unit.

The four gears 44 are rotationally held by this motor bracket 59. Among these gears 44, the gear 44 at the rightmost in FIG. 32 is meshed with a gear 61 that is fitted to the motor shaft of the black drum driving motor 42. In this layout, the black drum driving motor 42 rotates the gear 44, which rotates the photosensitive drum 28 (see FIG. 3) for monochrome image forming.

Among the three gears 44 other than the rightmost gear 44, the left two gears 44 in FIG. 32 are rotated by a motor shaft 62 of the color drum driving motor 41. The second gear 44 and the third gear 44 from the left are meshed with the relay gear 43. In this layout, the third gear 44 is rotated following the rotation of the second gear 44. In other words, the three gears 44 are rotated following the rotation of the color drum driving motor 41. Accordingly, the photosensitive drums 28 for C, M, and Y (see FIG. 3) are rotated at the same time.

The gears to drive the photosensitive drums do not have a special vibration absorption mechanism in fitting the motor, so as to be able to accurately match the design value of the center distance between the gears in the module 0.5. In other words, the black drum driving motor 42 and the color drum driving motor 41 are directly fixed to the motor bracket 59.

In the configuration of directly fitting the motor to the motor bracket 59, the vibration of the motor during the operation is solidly propagated to the motor bracket 59, amplified, and discharged. The sound generated from this vibration includes many driving frequency components of the stepping motor as the drum driving motor.

Figure 34:
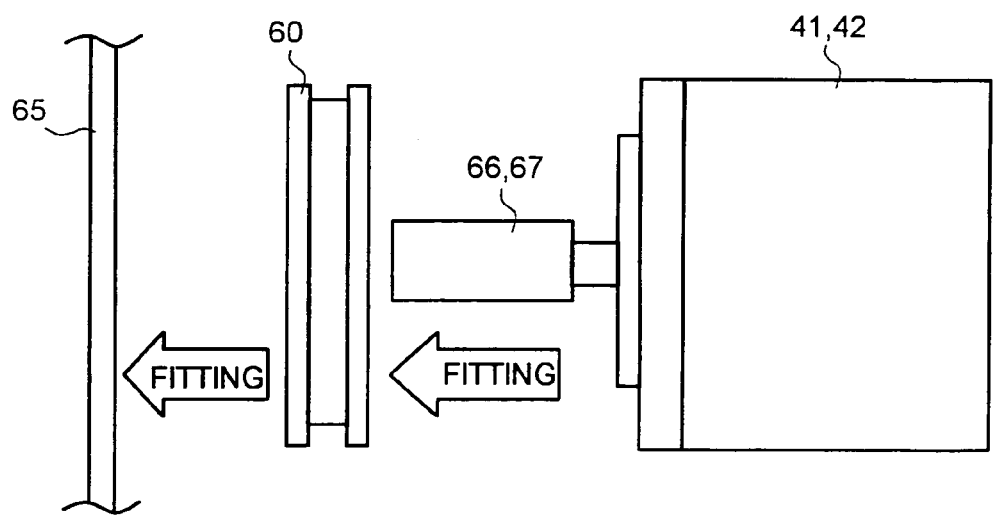
FIG. 34 is a schematic diagram for illustrating an installation of a driving motor that drives the photosensitive drum after the modification.
Figure 35:
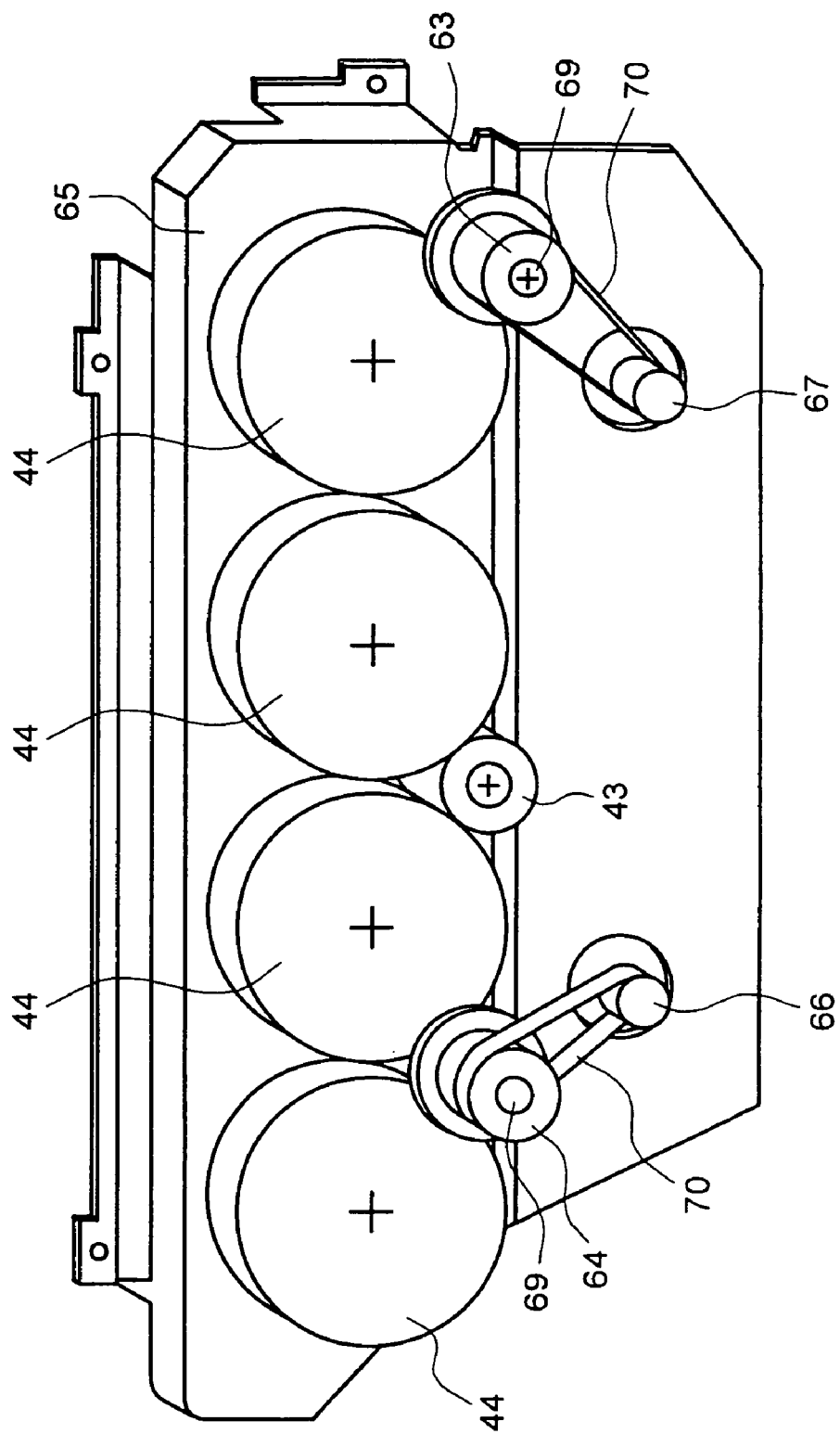
FIG. 35 is a schematic diagram of the photosensitive drum driving mechanism after the modification.

In order to decrease the generation of the conspicuous sound that includes many driving frequency components of the stepping motor, the color drum driving motor 41 and the black drum driving motor 42 are fitted to the motor bracket 65 via a vibration absorption rubber mount 60 as shown in FIG. 34. In other words, this vibration absorption rubber mount 60 becomes a constituent element of a reduction unit that reduces the generated sound.

For the vibration absorption rubber mount 60, a stepping motor mount manufactured by NOK Corporation, for example, can be used. This stepping motor mount is used in experiments to test the effects of a noise measurement that is described later.

When the vibration absorption rubber mount 60 is provided between the drum driving motor and the motor bracket 65, the precision of the center distance between the gears become worse. Therefore, in the present drum driving mechanism, the motor shaft is not directly meshed with the gears, but the driving force is transmitted from the motor shaft to the gears 44 via a timing belt mechanism.

Specifically, timing pulleys 66 and 67 are fitted to the motor shafts of the color drum driving motor 41 and the black drum driving motor 42 respectively. The driving force of the motor is transmitted to two-stage gears/pulleys 63 and 64 with a timing belt that is wound around the timing pulleys 66 and 67. In other words, the two-stage gears/pulleys 63 and 64 are rotated following the rotation of the motor shaft.

The gears of the two-stage gears/pulleys are meshed with the drum driving gears 44. With this arrangement, the gears 44 can be rotated following the rotation of the drum driving motor, and the photosensitive drums 28 (see FIG. 3) can be rotated, like in the configuration before the modifying.

A portion (i.e., a lower portion in FIG. 36) of the motor bracket 65 that holds the motor is bent to stretch to the opposite side of the motor from the upper portion. The vibration absorption rubber mount 60 is disposed to be in contact with the motor bracket 65, in the room formed at the stretched portion. The motors 41 and 42 are disposed on the vibration absorption rubber mount 60 at the opposite side of the motor bracket 65, such that the motor shafts stretch to the opposite side of the motor bracket 65 (i.e., the left side in FIG. 36). As explained above, the motor bracket 65 and the motors are not directly held, but are held via the vibration absorption rubber mount 60.

Figure 36:
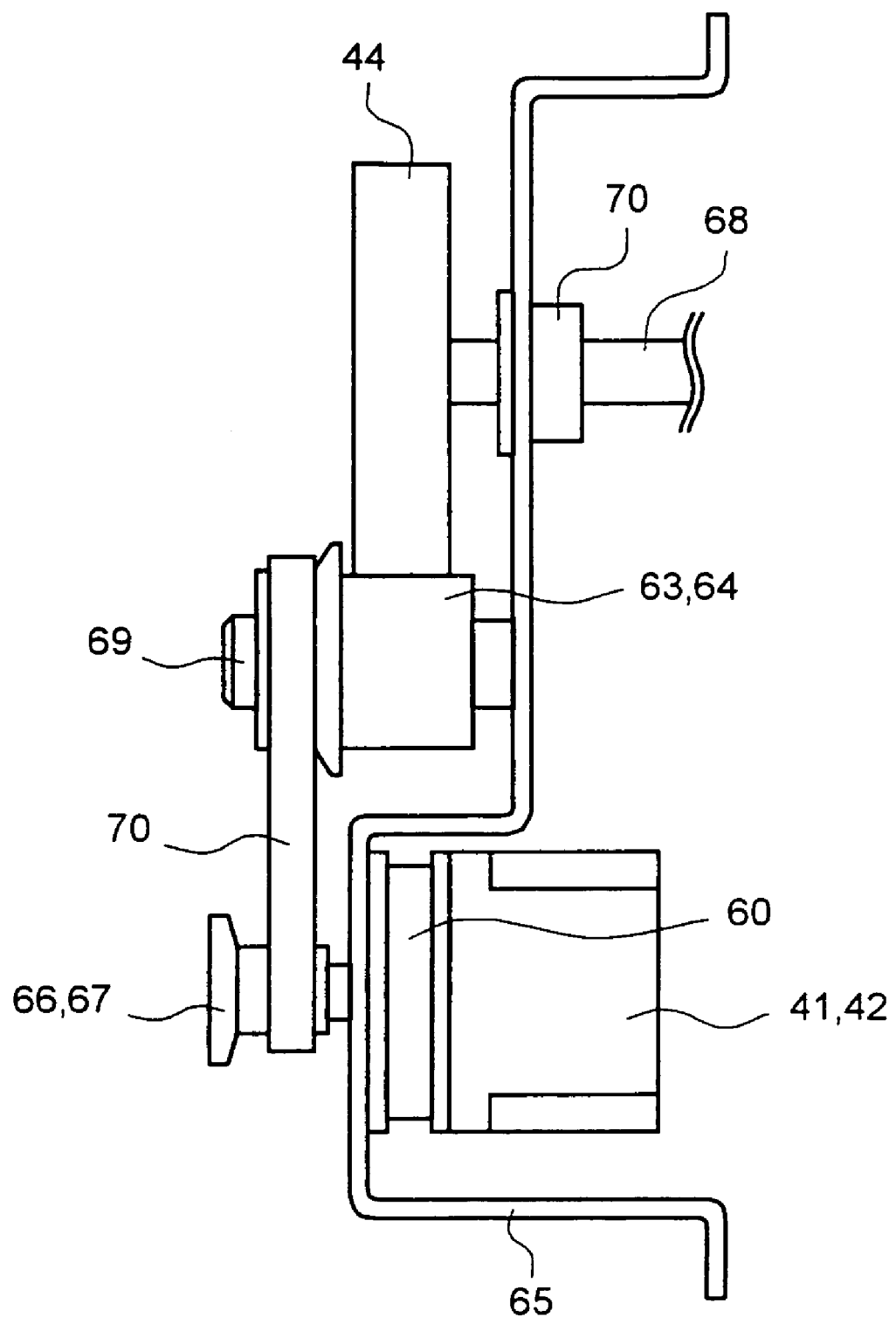
FIG. 36 is a side view of the photosensitive drum driving mechanism after the modification.

In the present configuration, the two-stage gears/pulleys 63 and 64 are disposed at the left side (i.e., the side at which the gears 44 are disposed) of the motor bracket 65 in FIG. 36. Therefore, the motor shafts need to stretch to the left position in FIG. 36 by this portion. However, the provision of the stretch portion in the motor bracket 65 makes it possible locate the motors at the left side in FIG. 36, and this avoids the need to have a long motor shaft. Consequently, it is possible to suppress the eccentricity of the motor shaft due to the long motor shaft or the generation of noise due to this eccentricity.

In the present configuration, it is preferable that a stud 69 to fit the two-stage gears/pulleys 63 and 64 has large strength. When the stud 69 has insufficient strength, the gears 44 and the two-stage gears/pulleys are meshed in eccentricity, which also brings about the eccentricity of the drum shaft 68 via the bearing 70. The eccentricity of the drum shaft 68 may affect the image formed on the paper. In order to avoid the occurrence of this inconvenience, the strength of the stud 69 needs to be increased.

An elastic material that can absorb the vibration of the motors to some extent may be used in addition to the above vibration absorption rubber mount.

The above explains the measure to decrease the noise of the drum driving stepping motor.

A measure to decrease the noise of the paper feeding stepping motor will be explained as an example of a measure to decrease tonality. As described above, the paper feeding motor of the image forming apparatus is the stepping motor 56 (see FIG. 8). By controlling the driving of the stepping motor, paper is fed from the tray. In order to decrease noise of this motor, the following method of driving of the stepping motor 56 is available. The contents of this control will be explained below.

Figure 37:
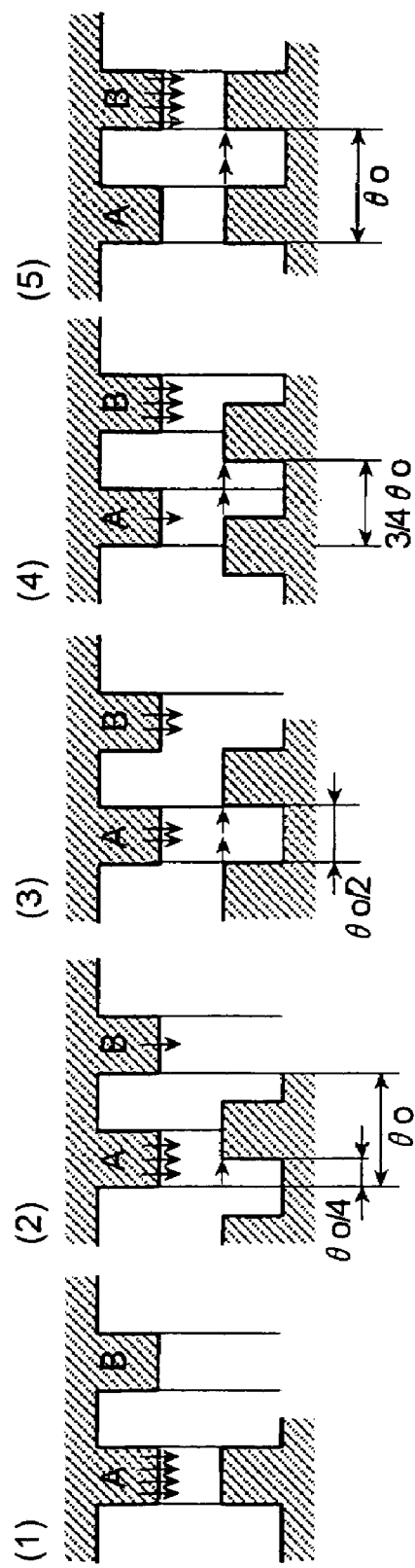
FIG. 37 depicts a driving control of a paper feeding stepping motor for illustrating another example of a modifying method according to the present invention.

FIG. 37 depicts a movement of the rotor of the stepping motor that is driven at a step angle of θ0. The step angle of θ0 of the stepping motor is determined based on a mechanical configuration. Usually, the rotor moves at one time at each step angle θ0. Therefore, when the step angle θ0 is large, the move of the rotor is not smooth, and generates vibration, which becomes a cause of noise.

In the present configuration, the stepping motor is driven at a step angle smaller than the step angle θ0 that is determined based on a mechanical configuration according to the control of an electronic circuit as shown in FIG. 37. In other words, what is called a micro step driving is carried out. Current supply is controlled as follows. Current to be supplied to one phase of an excitation phase is gradually increased on one hand, and current to be supplied to the other phase is gradually decreased on the other hand (see (1) to (5) in FIG. 37). This control makes it possible to drive the stepping motor at a step angle smaller than the step angle θ0. This move is smoothed to decrease noise.

Figure 38:
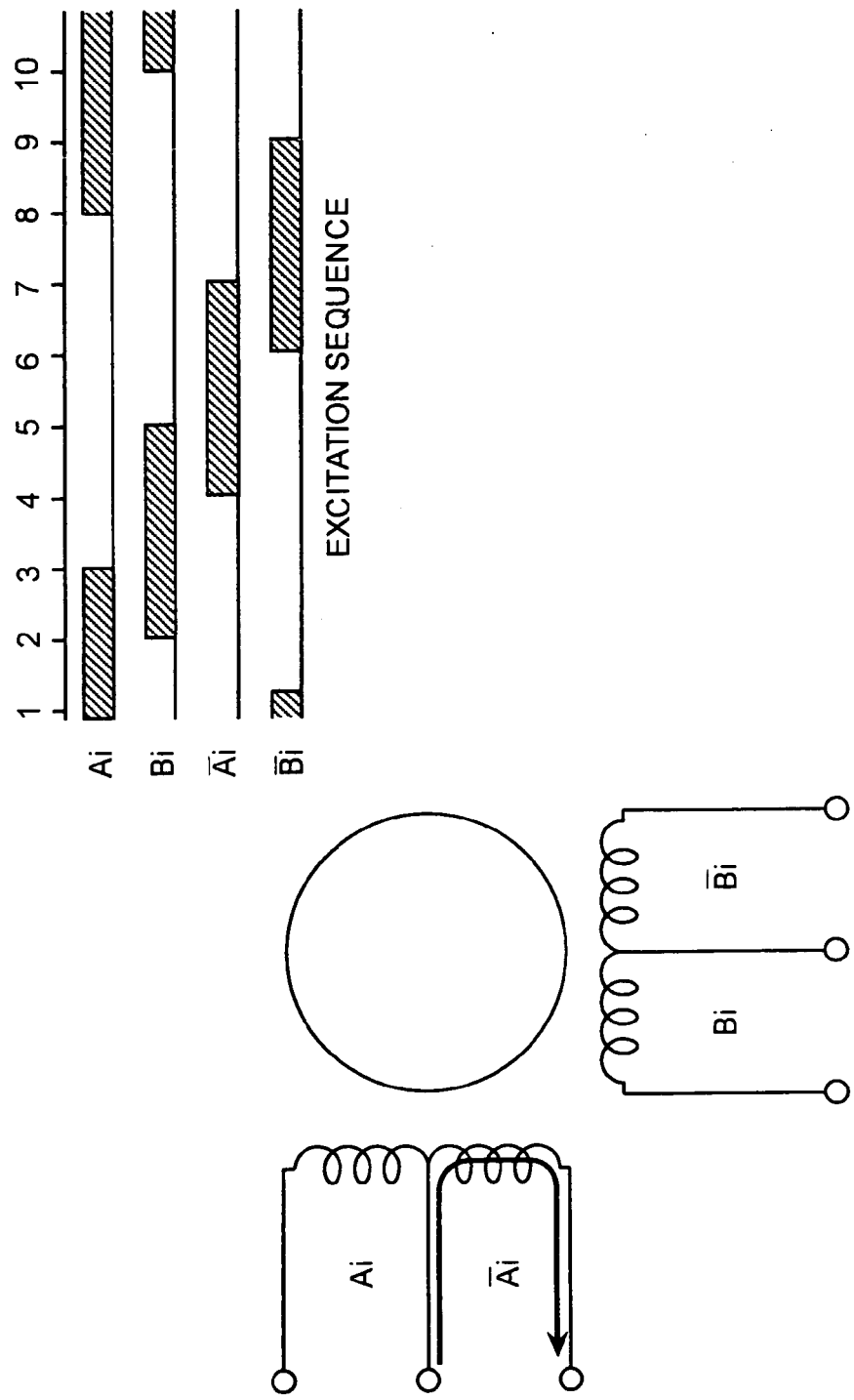
FIG. 38 depicts an excitation sequence of micro-step driving of the paper feeding stepping motor for illustrating still another example of a modifying method according to the present invention.

FIG. 38 depicts a one-two phase excitation sequence as one micro-step driving of the stepping motor. The one-two phase excitation is an excitation system of alternately repeating one-phase excitation to excite a coil in each one phase and two-phase excitation to excite a coil in each two phases. When the stepping motor is driven using this excitation system, the step angle of the motor becomes ½, which makes the rotor move smoother than when the rotor usually rotates. This smooth move can decrease vibration.

Figure 39:
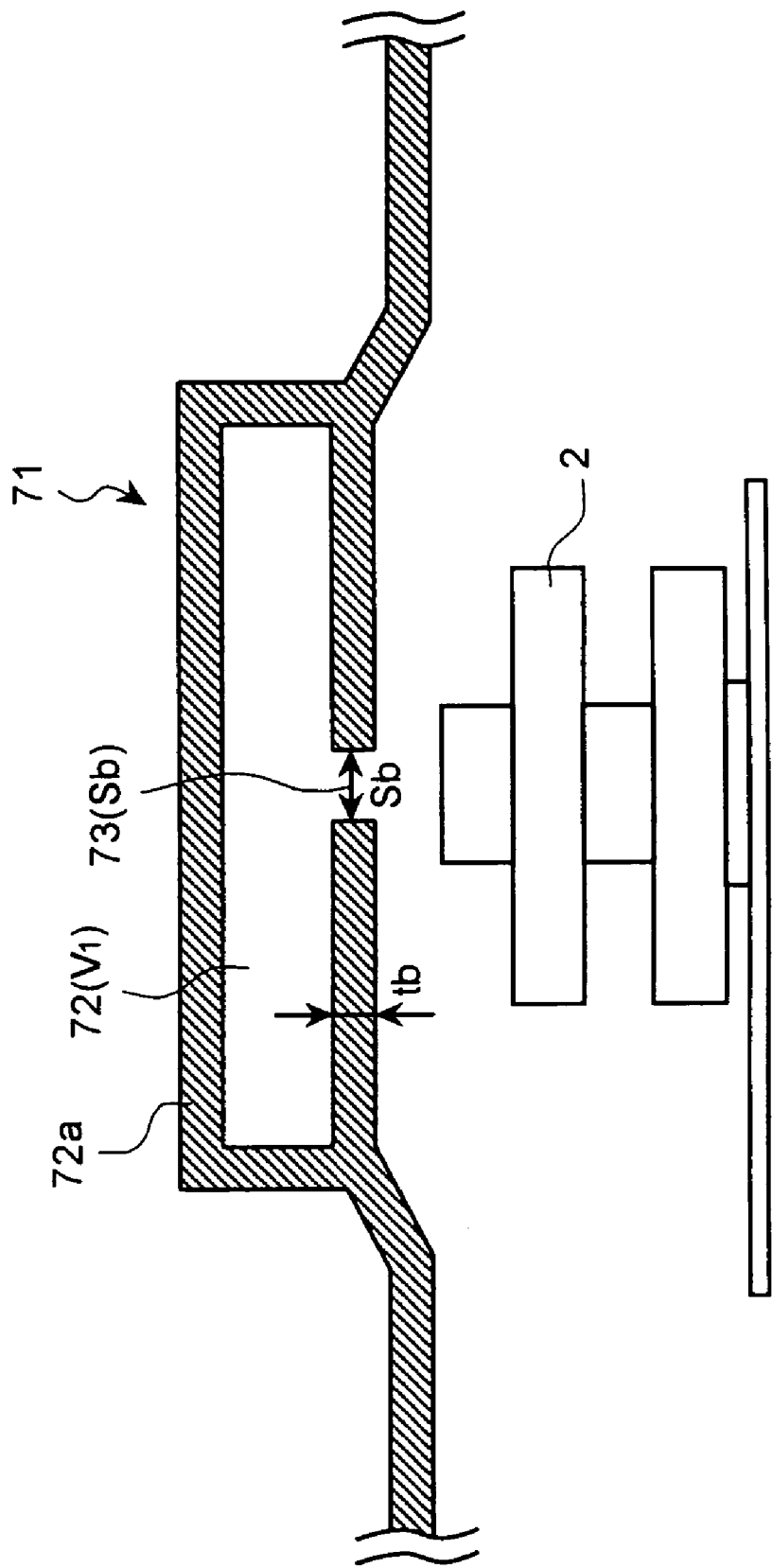
FIG. 39 is a cross-unit of a Helmholtz resonator provided near a polygon mirror motor for illustrating still another example of a modifying method according to the present invention.

A measure to decrease sound generated from the polygon mirror motor will be explained with reference to FIG. 39, as an example of a measure to decrease tonality. A Helmholtz resonator 71 is provided near the polygon mirror motor 2. Specifically, the Helmholtz resonator 71 is provided on the upper portion of the housing 11 that holds the polygon mirror motor 2.

The Helmholtz resonator 71 has a cavity formation member 72a to form a cavity 72 having a volume V1. The cavity formation member 72a is formed integrally with the housing 11. An aperture 73 (having a cross-unital area Sb) that communicates to the cavity 72 is formed at a portion of a position opposite to the polygon mirror motor. When the portion on which the aperture 73 is formed has a plate thickness of Tb, this aperture 73 corresponds to a short tube having a length Tb and an aperture area Sb in a general Helmholtz resonator. This structure functions as the Helmholtz resonator 71.

The polygon mirror motor 2 is driven in this configuration. When the sound pressure works on the entrance of the aperture 73 due to the vibration, the air (i.e., a medium) within the aperture 73 (i.e., the short tube) carries out a unified operation, thereby generating a change in the air pressure within the cavity 72. This phenomenon becomes equivalent to a mass point-spring model of a dynamic system, when the air within the aperture 73 (i.e., short tube) is the mass point and when the pressure change due to the change in the volume of the air within the cavity 72 is the spring. This phenomenon generates resonance in the frequency (Helmholtz resonance frequency) to be described later. In other words, as the acoustic energy of the Helmholtz resonance frequency is confined in the cavity 72, sound in exterior space can be decreased.

The Helmholtz resonance frequency Fh (hertz) is calculated from the following expression.

$$Fh = C/2\pi (Sb/(V1 \cdot Tb))^{1/2}$$

C: Acoustic velocity

In other words, the resonance frequency Fh, that is, the frequency of the sound to be decreased, can be changed by changing the aperture area Sb and the length Tb (i.e., the plate thickness of the portion of the housing 11 on which the aperture 73 is provided) of the aperture 73, and the volume V1 of the cavity 72 formed by the cavity formation member 72a. The sizes of each unit are designed such that the Helmholtz resonance frequency coincides with the frequency of the sound in which the sound level is the highest among the sound generated when the polygon mirror motor 2 is driven. With this arrangement, the sound generated from the polygon mirror motor 2 can be decreased effectively.

From the above result of the noise measurement (see FIG. 10 to FIG. 12), it is known that the sound from the polygon mirror motor is extracted as noise during the color mode, but this sound is not so conspicuously felt as noise during the monochrome mode. In this case, as described above, the sizes of each unit are determined such that the Helmholtz resonance frequency coincides with the frequency of the sound in which the sound level is the highest among the sound generated when the polygon mirror motor 2 is driven. On the other hand, when other frequency is higher during the monochrome mode, a Helmholtz resonator that makes this frequency equivalent to the resonance frequency may be provided separately.

While a Helmholtz resonator may be provided for each corresponding frequency, a mechanism of changing the aperture area Sb of the aperture 73 between the color mode and the monochrome mode may be provided. For example, a lid member or the like that can slidably move between a position of closing the aperture 73 to some extent and a position of not closing the aperture is provided. Alternatively, this lid member is moved corresponding to the mode. In this way, the resonance frequency in each mode can be changed to coincide with the frequency in which the sound level becomes large during each mode.

A measure to decrease the charging noise will be explained next, as an example of a measure to decrease tonality. The charging noise is generated as follows. When the charging roller 36 charges the photosensitive drums 28 (see FIG. 3), generally, attracting force and repulsive force work alternately between the surface of the charging roller 36 and the photosensitive drums 28 due to the AC component of a bias voltage. The sound generated from the photosensitive drums 28 due to this vibration is the charging noise. This noise is abrasive pure tone having a high frequency. In general, the charging noise includes a frequency of AC component and a frequency component (i.e., higher harmonic component) of an integer times this frequency.

Figure 40:
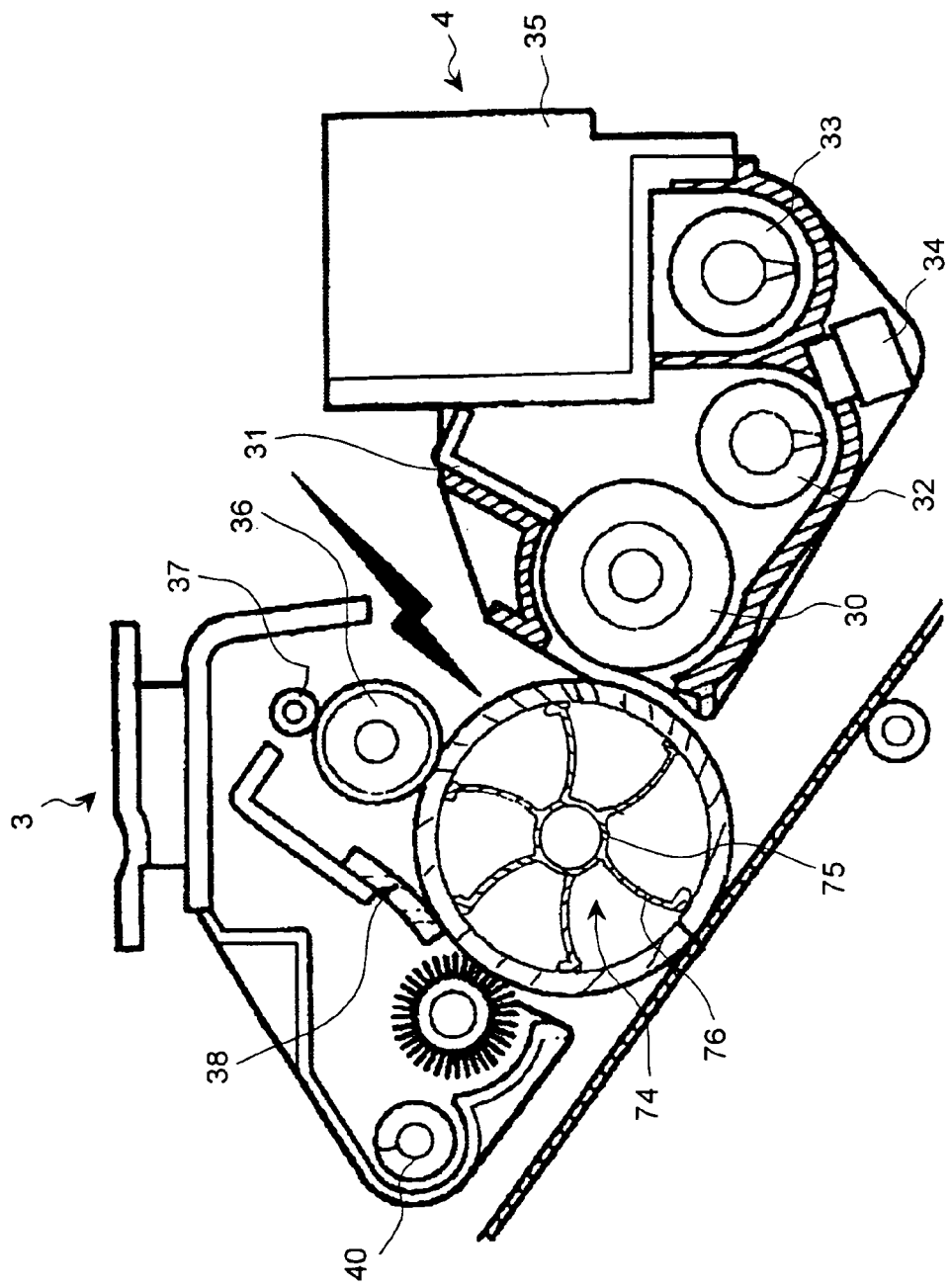
FIG. 40 is a schematic diagram of a mechanism of suppressing vibration of the photosensitive drum for illustrating still another example of a modifying method according to the present invention.
Figure 41:
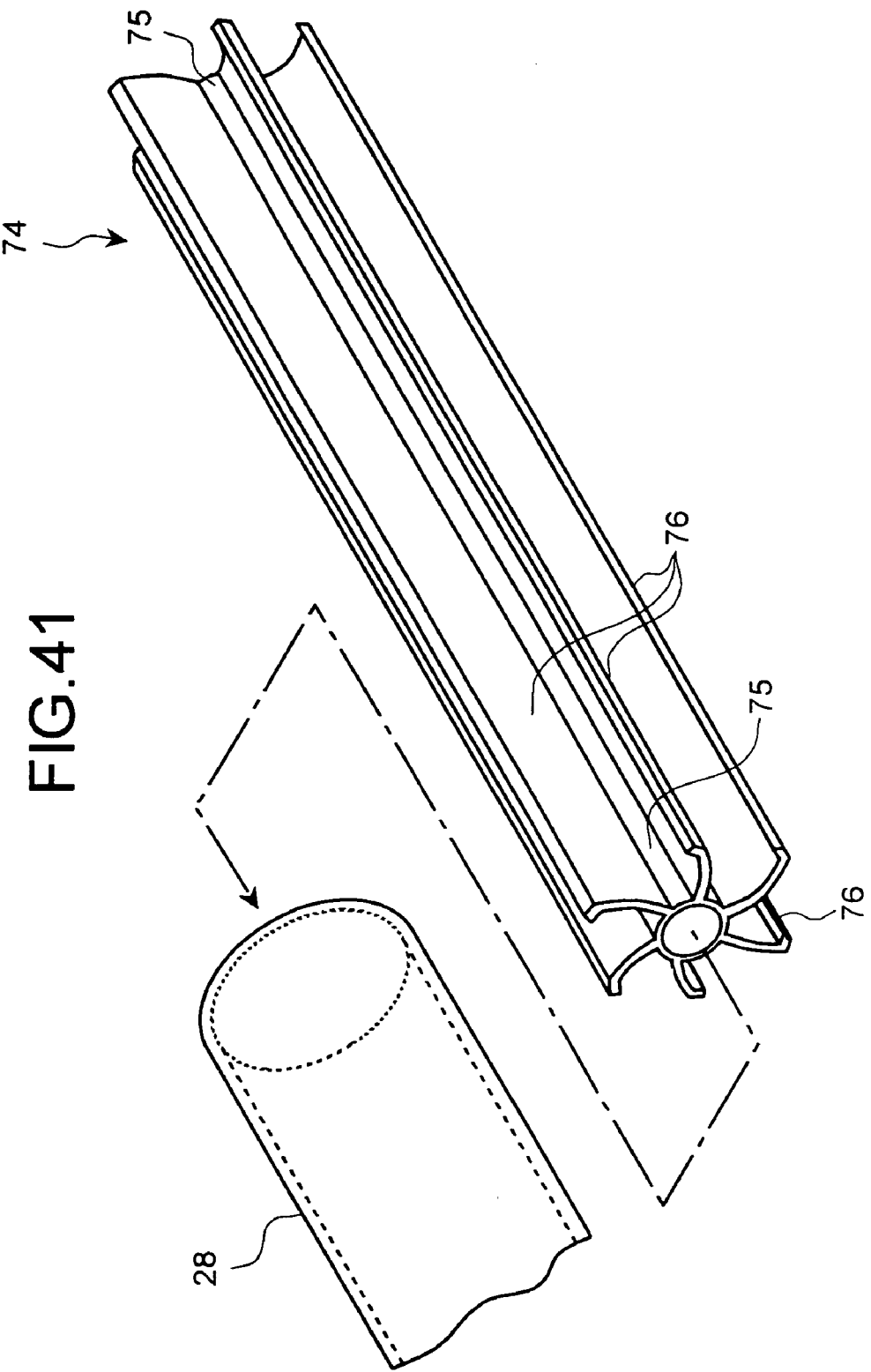
FIG. 41 is a disassembled perspective view of the mechanism of suppressing vibration of the photosensitive drum.

A measure to decrease the charging noise will be explained with reference to FIG. 40 and FIG. 41. A damping material 74 is disposed in a room portion of the photosensitive drum 28 that is provided with a measure against the charging noise. The damping material 74 has a hollow cylindrical base unit 75 that extends to the axial direction of the photosensitive drum 28, and a plurality of blades 76 that project radially from the base unit 75. The central axis of the base unit 75 approximately coincides with the central axis of the photosensitive drum 28.

The front end of each blade 76 of the damping material is in pressure contact with the inner surface of the photosensitive drum 28, thereby holding the damping material 74 within the photosensitive drum 28. Each blade 76 preferably includes an elastic material like rubber or resin, or a material containing these materials, such as a material containing urethane rubber, or a thermoplastic resin such as polypropylene resin or polyamide resin. When an elastic material is used for the blade 76, the front end of the blade 76 is crimped against and is held by the photosensitive drum 28, due to the elastic force. Therefore, a bonding work using an adhesive agent or aligning is not necessary, which facilitates the mounting and dismounting work.

As described above, when the damping material 74 is disposed such that the blades 76 are crimped against the inner surface of the photosensitive drum 28, the damping material 74 works to suppress the vibration of the photosensitive drum 28. Therefore, the vibration of the photosensitive drum 28 that is generated when the charging roller 36 charges the photosensitive drum can be suppressed. As the member to suppress the vibration of the photosensitive drum 28 is disposed within the photosensitive drum 28, no room to install the damping material needs to be provided.

In order to decrease noise by suppressing the vibration of the photosensitive drum 28, a metal pillar may be engaged with the hollow portion of the photosensitive drum 28, instead of using the damping material 74 having the above configuration. A commercially available damping material (for example, Hama Damper manufactured by Yokohama Rubber Co., Ltd.)

The above explains about a detail example of the measure to decrease tonality. A measure to decrease sharpness (i.e., higher harmonic component) will be explained next, based on a detailed example.

As a measure to decrease sharpness the paper sliding noise may be decreased. The paper sliding noise is generated when the fed paper slides against members.

Figure 7:
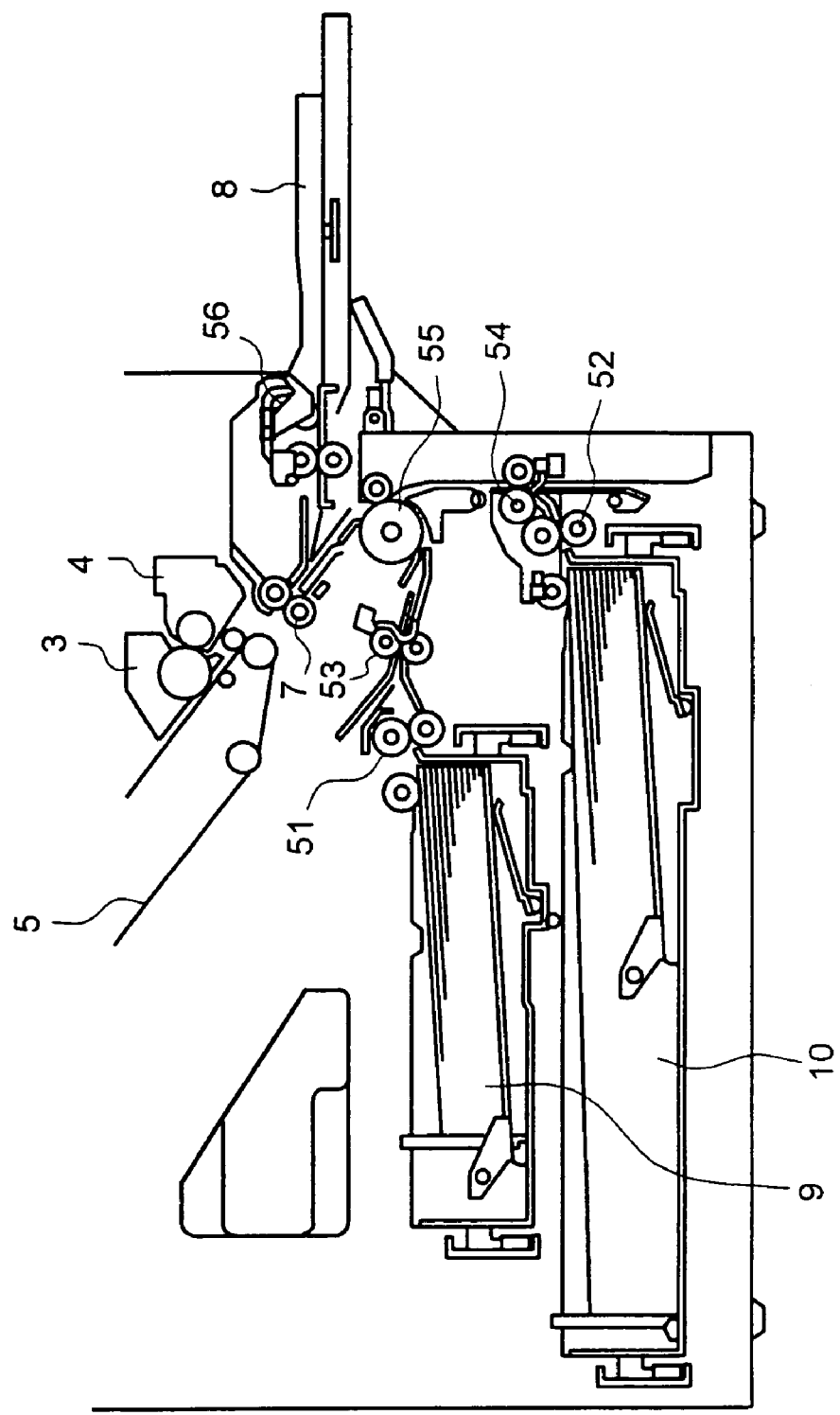
FIG. 7 is a front cross unit of a paper feeder of the image forming apparatus.

As described above, the first paper feeding unit 51 or the second paper feeding unit 52 feeds the paper accommodated in the first tray 9 or the second tray 10. The relay roller 53 and the feeding roller 55 feed the paper to the position of the resist roller 7 (see FIG. 7).

Figure 42:
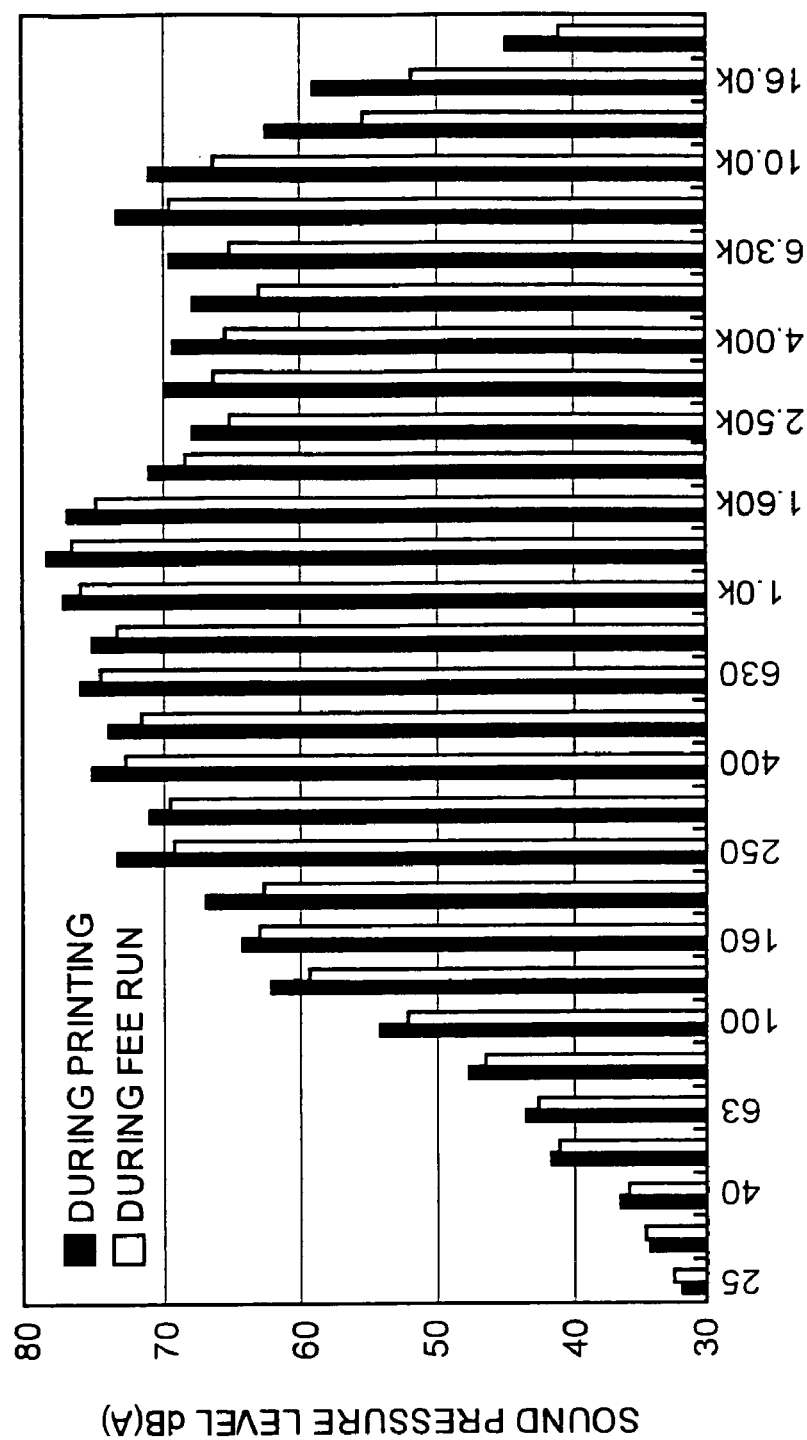
FIG. 42 is a histogram of the sound pressure level for each frequency band of sound generated from the image forming apparatus during an image forming operation with feeding paper and without feeding paper (i.e., during a free run)
Figure 43:
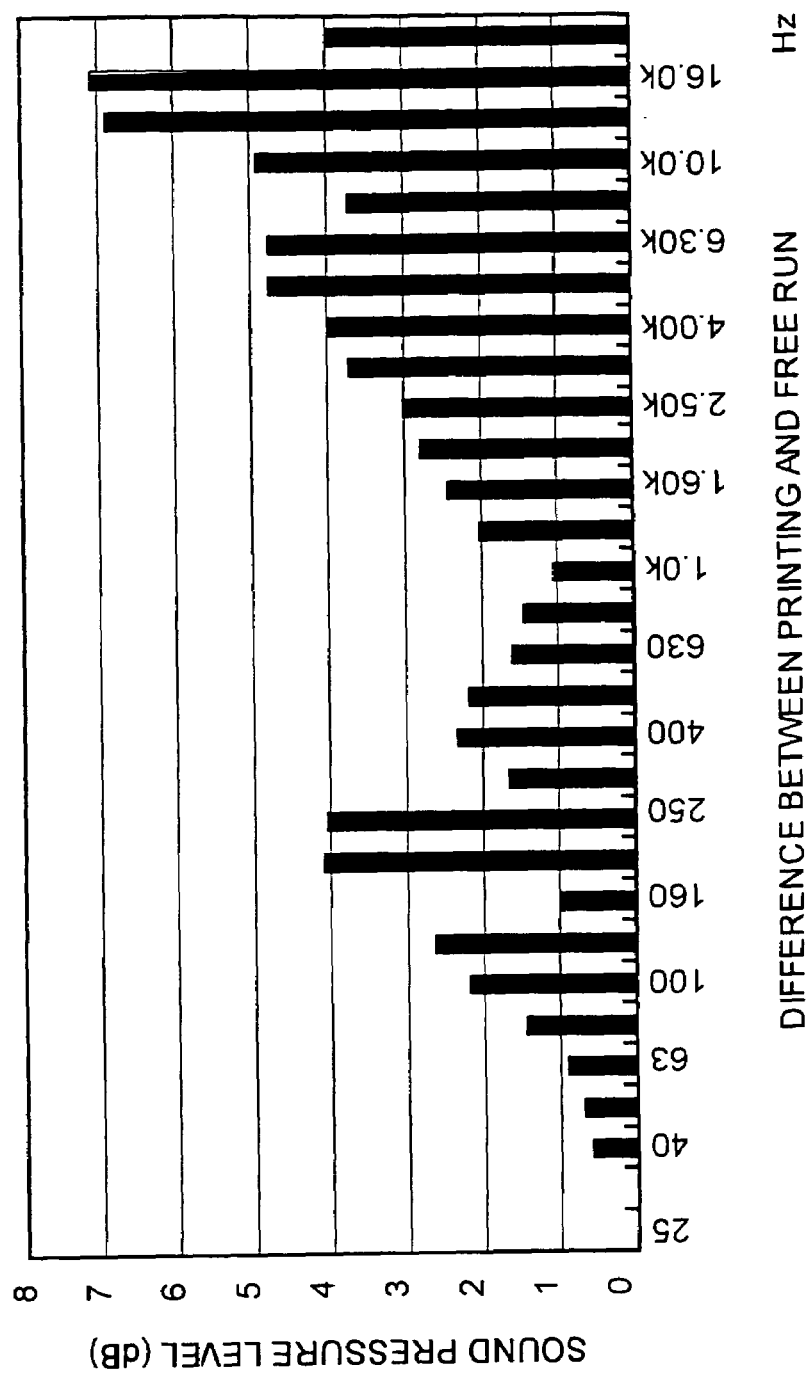
FIG. 43 is a histogram of a difference between the sound pressure level for each frequency band of sound generated from the image forming apparatus during the image forming operation with feeding paper and without feeding paper.

FIG. 42 is a histogram of a result of analyzing a frequency (i.e., a ⅓ octave band analysis) after analyzing the noise generated from the image forming apparatus, during the normal printing of forming an image by feeding the paper accommodated in the first tray 9 or the second tray 10 and during the free run of printing without feeding the paper. FIG. 43 is a histogram of a difference between a sound pressure level for each frequency band of sound that is obtained from the noise during the normal printing and during the free run that is shown in the analysis result.

In other words, the sound pressure level for each frequency band shown in FIG. 43 indicates a difference between the noise generated from the image forming apparatus when the paper is fed from the first tray 9 or the second tray 10 and is fed and the noise generated from the apparatus when the paper is not fed or fed. The sound pressure level increases in each frequency band.

From the graph shown in FIG. 43, it is known that a difference of 3 decibels or above is present between the normal printing time and the free run time, in two bands of a band from around 200 to 250 hertz, and a band of 3.15 hertz or above. The difference of 3 decibels or above indicates that the difference of acoustic energy is two times or more.

As a result of investigating the above result of the analysis, it is clear that the component of the band around 200 to 250 hertz is attributable to the sound generated when the paper collides against the resist roller 7. On the other hand, it is clear that the component of the frequency band of 3.15 kilohertz or above is attributable to the sound generated when the paper collides against the members during the feed of the paper. A difference of 7 decibels or above is present in the band from 12.5 kilohertz to 16 kilohertz. This band gives a large influence to sharpness. From this, it is clear that to decrease the paper sliding noise is effective to decrease noise.

Figure 44:
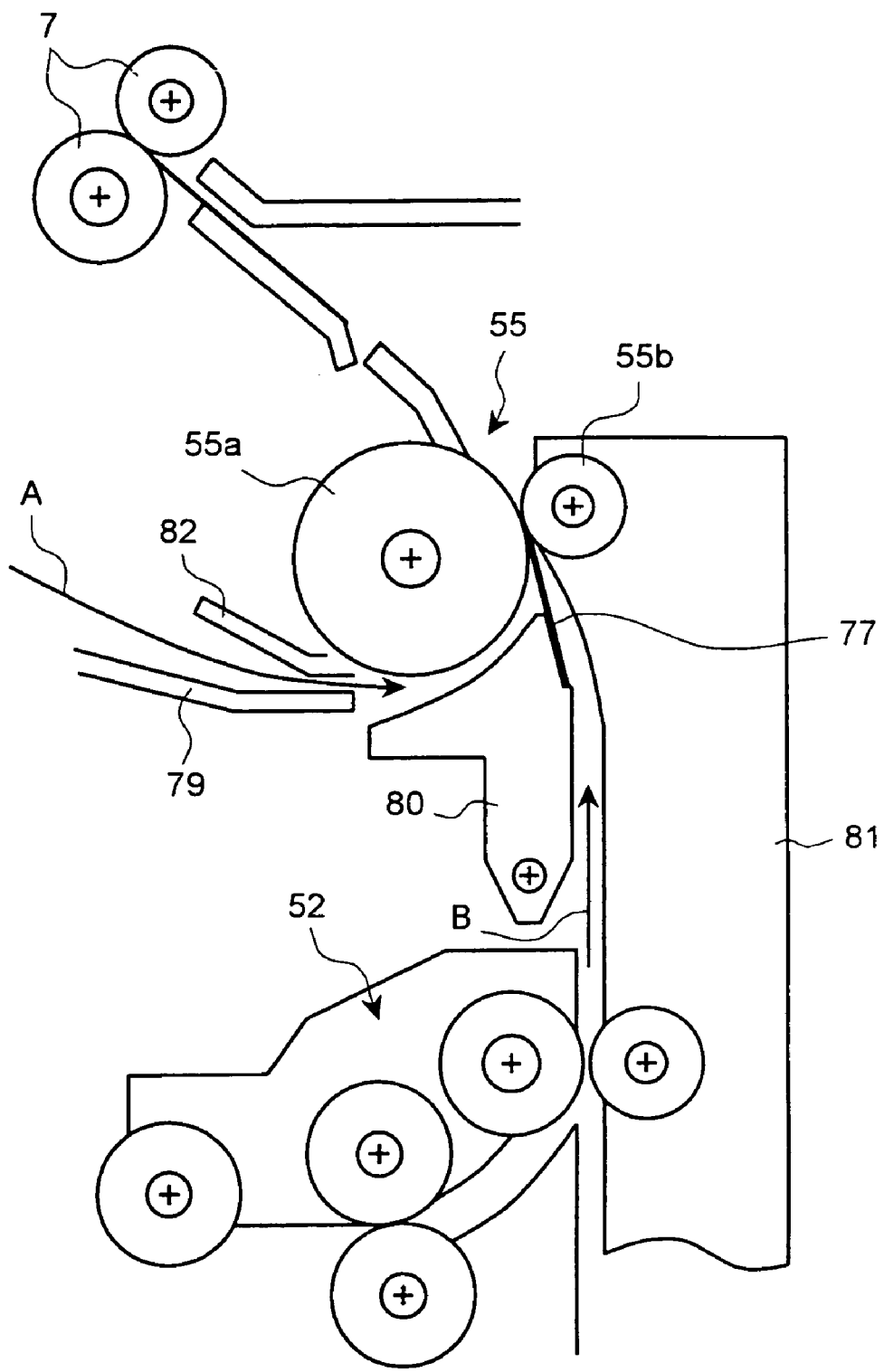
FIG. 44 is a schematic diagram of the paper feeder of the image forming apparatus.

A measure to decrease the paper sliding noise of the paper fed by the paper feeding unit, the relay roller 53, and the feeding roller 55 will be explained with reference to FIG. 44. The feeding roller 55 includes a shaft, and a plurality of rollers that are provided around the shaft, and has a roller 55a and a roller 55b that are oppositely disposed to sandwich a paper feeding route. The paper that is fed along a feeding route A (i.e., paper that is fed from the first tray 9) or the paper that is fed along a feeding route B (i.e., paper that is fed from the second tray 10) is guided to between the rollers 55a and 55b. The rollers 55a and 55b feed the paper toward the resist roller 7.

Guide members 80, 81, and 82 to feed the paper along a predetermined route are disposed near the feeding roller 55.

The guide member 80 forms a room to guide the paper fed along the feeding route A with the roller 55a to between the rollers 55a and 55b. The guide member 80 also forms a room to guide the paper fed along the feeding route B with the guide member 81 to between the rollers 55a and 55b.

A guide member 77 including a flexible sheet (for example, a mylar sheet) that extends to the paper feeding direction (i.e., a vertical direction in FIG. 44) is provided at a downstream portion (i.e., an upper side) of the guide member 80. This guide member 77 guides the paper fed from the feeding routes A and B to between the rollers 55a and 55b.

Figure 45:
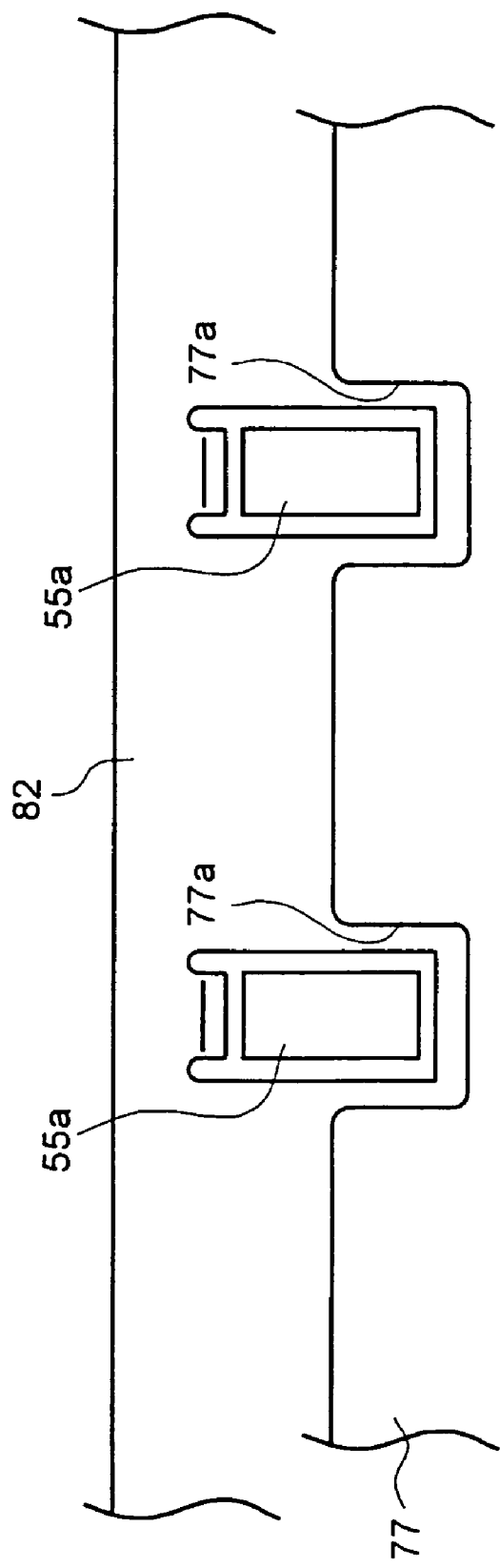
FIG. 45 is a schematic diagram for illustrating a positional relationship between a paper feeding roller as a constituent element of the paper feeder and a guiding member including a flexible sheet that guides the paper.

As shown in FIG. 45, a helical groove 77a is formed by cutting or the like at the front end of the guide member 77 where the roller 55a is disposed to avoid a crossing of the guide member 77 with the roller 55a. With this arrangement, the paper is brought into contact with the front end to securely guide the paper to between the rollers 55a and 55b.

Figure 46:
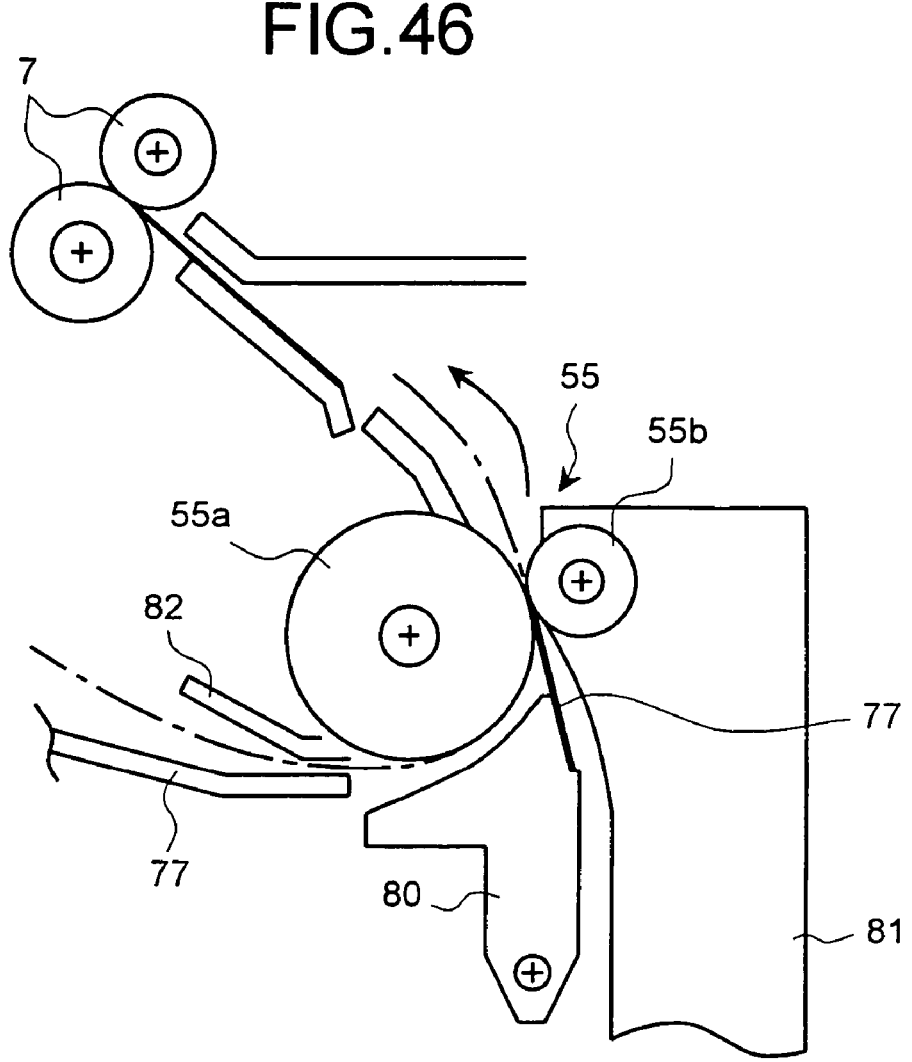
FIG. 46 is an enlarged diagram of a portion near the guiding member of the paper feeder.

As shown in FIG. 46, the paper from the feeding route A is fed while sliding with the front end of the guide member 77. A conventional ordinary guide member 77 is manufactured by cutting a flexible sheet in a predetermined shape. The front end (i.e., the cut portion) usually has burr. It is very hard to remove each burr, and this takes cost and time. Therefore, usually this work is not carried out, and the paper slides against the front end having this burr. This generates abrasive noise.

Figure 47:
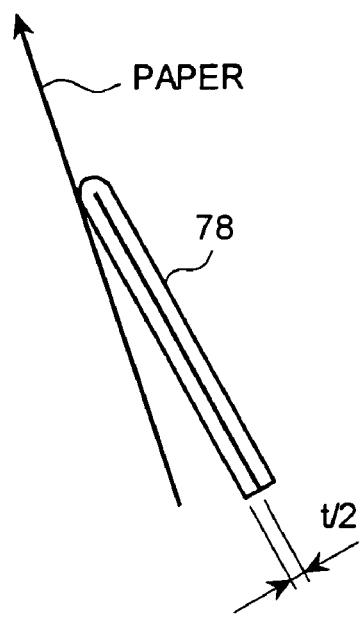
FIG. 47 is a schematic diagram of the guiding member with a noise countermeasure.

In the present modifying method, the guide member 77 having a configuration as shown in FIG. 47 is employed, thereby decreasing noise abrasive noise that is generated due to the sliding of the front end of the guide member 77 with the paper.

Figure 48:
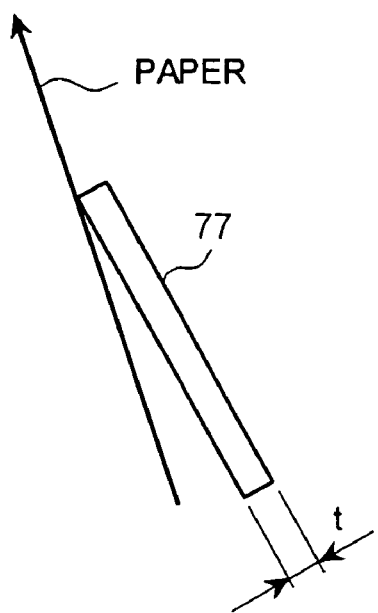
FIG. 48 is a schematic diagram of the guiding member without the noise countermeasure.

As shown in FIG. 48, the conventional guide member 77 including a flexible sheet that is cut to have a thickness t in a predetermined shape is used straight as the guide member. The front end on which the paper slides is a cut portion. On the other hand, in the configuration shown in FIG. 47, a flexible sheet having a thickness of t/2 is folded into two sheets, and the folded corner portion becomes the front end of a guide member 78. When the guide member 78 having this configuration is used, the paper fed as described above slides on the folded corner portion as the front end. This corner is the cut portion and has a smooth R shape. Therefore, the abrasive noise attributable to the burr that is generated from the conventional cut portion can be decreased. The thickness obtained by folding the sheet into two is the same as the thickness of the conventional guide member 77. Therefore, required elasticity can be exhibited, and no trouble occurs in the function of the guide member.

The above explains about a detailed example of the measure to decrease sharpness. A measure to decrease impulsiveness (i.e., impulse component) will be explained next, based on a detailed example.

In the image forming apparatus having the above configuration, the generation of impulsiveness is attributable to the fixing oil applying noise in almost all cases (see FIG. 10 to FIG. 12). In the image forming apparatus having the above configuration, in order to suppress the increase in the oil consumption quantity, the oil applying unit 47 is driven and is brought into contact with the fixing belt 13 each time when the paper is fed (see FIG. 6). The contact and separation noise is generated percussively each time when the paper is fed, therefore, this noise gives discomfort.

This noise generated due to the fixing oil applying can be solved when an oilless toner is used to form an image. In other words, this oilless toner contains wax, and therefore, has easy separation between the fixing belt and the paper without applying oil. Accordingly, the utilization of the oil applying unit 47 is not necessary, and the generation of percussive noises attributable to the contact and separation between the oil applying unit 47 and the fixing belt 13 can be prevented. In using the oilless toner, the process of image forming by the photosensitive units 3 needs to be corrected to match the oilless toner.

The above explains about the detailed example of the measure to decrease impulsiveness. When the index S does not satisfy the condition, all the measures described above may be taken. Alternatively, only a measure that is effective for a specific parameter to be decreased may be taken after determining this measure based on a measurement result from among the psycho-acoustic parameters including loudness, sharpness, tonality, and impulsiveness.

The above explains about the detailed example of decreasing the discomfort index S. The present inventor measures the sound generated from the image forming apparatus in which the above measure is taken, in a condition similar to that in which the sound generated from the image forming apparatus before taking the countermeasures is measured. Effect of the measurement is investigated based on the measurement result. The measurement results compared below are obtained by collecting sound at the front surface side of the image forming apparatus when the apparatus is operated in the color mode (1).

Figure 49:
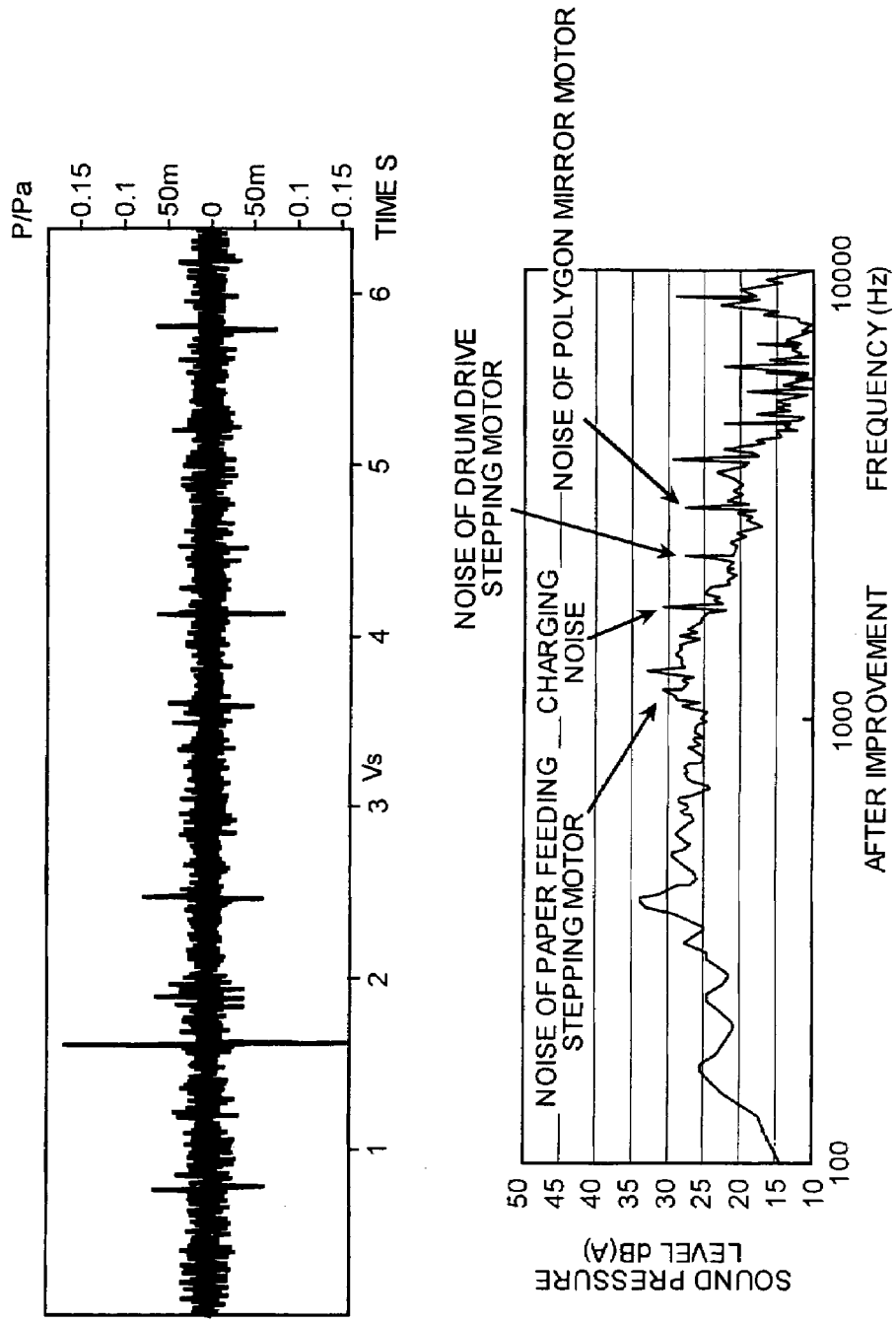
FIG. 49 is a graph of a result of analyzing sound generated from the image forming apparatus with a countermeasure following the modifying method according to the present invention.

FIG. 49 is a graph of a result of analyzing the noise after taking countermeasures. In comparing the noise analysis result after taking the countermeasures with the analysis result before taking the countermeasures (see to FIG. 10), the following result is obtained. The noise of the paper feeding stepping motor is decreased by about 10 decibels, the charging noise is decreased by about 5 decibels, the noise of the drum driving motor is decreased by about 8 decibels, and the noise of the polygon mirror motor is also decreased by about 10 decibels. The fixing oil applying noise is not generated. From the above, it is clear that the sound generated from each source sound source can be decreased by taking the above countermeasures.

Table 17 expresses a result of the comparison between the psycho-acoustic parameter values obtained from the measurement results of before and after taking the countermeasures and the sound quality evaluation values derived from the sound quality evaluation expression (A).

The image forming apparatus is manufactured according to the design contents that are provided such that the discomfort index S obtained from the sound generated from the image forming apparatus satisfies the above condition (step S2: manufacturing process). Through the above manufacturing process, the image forming apparatus that makes the index S satisfy the above condition, that is, the image forming apparatus that generates little unpleasant noise can be manufactured. This image forming apparatus can be provided to users.

Further, as described above, the present invention can be applied as a countermeasure against noise generated from the image forming apparatus that is once sold in the market. In other words, noise generated from the image forming apparatus that is already sold is measured in the manner as described above. The above sound quality evaluation expression is used to derive the discomfort index S from the result of the measurement. The derived discomfort index S is investigated whether it satisfies a predetermined condition. When the discomfort index S satisfies the predetermined condition, it is considered that the apparatus generates little discomfort. Therefore, it is determined that modifying is not necessary. On the other hand, when the derived discomfort index S does not satisfy the predetermined condition, various kinds of modifying are provided to each unit of the image forming apparatus such that the discomfort index S satisfies the predetermined condition. With this arrangement, the image forming apparatus that generates little noise can be provided.

As described above, the present invention provides the method of evaluating noise that the image forming apparatus generates, and taking measures to decrease discomfort that

TABLE 17

| | Sound pressure level | Loudness | Sharpness | Tonality | Impulsiveness | Sound quality evaluation value according to expression (A) |
|---|---|---|---|---|---|---|
| Before countermeasures | 52.5 | 7.51 | 2.34 | 0.13 | 0.57 | 0.097 |
| After countermeasures | 49.0 | 6.53 | 2.48 | 0.09 | 0.46 | −0.339 |

As is clear from Table 17, the sound quality evaluation value after taking the countermeasures is "−0.339", which is smaller than a tolerance "−0.307" in the color mode (1) shown in Table 14. Therefore, taking the above countermeasures is considered to remodel the image forming apparatus with little discomfort.

Figure 50:
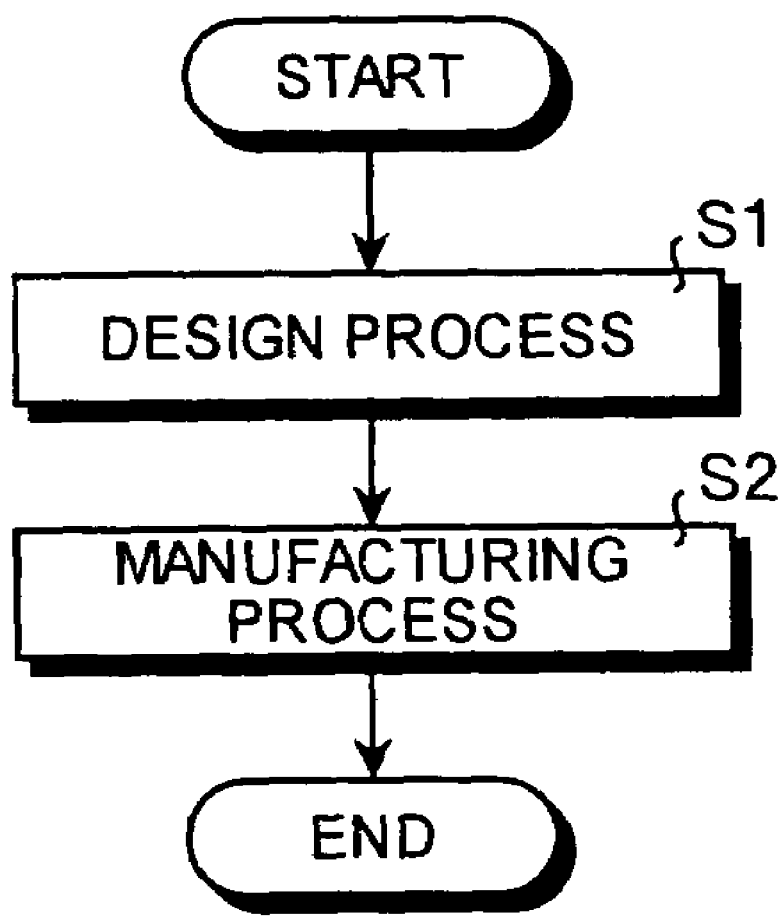
FIG. 50 is a flowchart of manufacturing the image forming apparatus according to the present invention.

The present invention provides an image forming apparatus that evaluates the sound quality of the image forming apparatus using the sound quality evaluation expression as derived above, and that makes the evaluation result (i.e., discomfort index S) satisfy a predetermined condition. Therefore, the present invention can be applied to develop and manufacture a new product as shown in a flowchart in FIG. 50, not only to remodel the apparatus based on the result of the sound quality evaluation.

Specifically, a configuration of each unit of the image forming apparatus is designed (at step S1: design process) such that the sound quality evaluation (i.e., discomfort index S) according to the above sound quality evaluation expression satisfies the above condition. For example, in designing the new product, various noise countermeasures as described above are employed.

the noise gives to a person based on the evaluation. The sound quality evaluation method is not limited to the method of deriving the index S. The following method using discomfort probabilities may also be used to evaluate sound quality. The image forming apparatus may be manufactured and modified using a result of the evaluation.

In order to evaluate sound quality, a method of deriving a sound quality evaluation expression capable of estimating sound quality from a result of the experiment obtained from the Scheffe's pair comparison method may be used. A difference between scores (i.e., a difference between scores of a pair of sounds obtained from the pair comparison method) is set as a target variable. A difference between a plurality of physical characteristics (i.e., psycho-acoustic parameters) is set as an explanatory variable. Then, a multiple linear regression analysis is carried out to obtain a model that estimates a difference between scores.

The present inventor applies the following multiple logistic regression model is applied as an estimation model of sound quality evaluation, separate from the estimation model of a difference between scores.

$$\hat{P}_{ij} = 1 \bigg/ \left\{ 1 + \exp\left[-\left(\sum_{l=1}^{L} b_l(x_{li} - x_{lj})\right)\right] \right\} \quad \text{(k)}$$

An expression (k) is not used to estimate a difference of relative merits between sound Ai and sound Aj, but is used to estimate win or loss of the sound Ai and the sound Aj as a probability Pij, (1−Pij).

$$P_{ij} = \frac{\pi_i}{\pi_i + \pi_j}, \quad 1 - P_{ij} = \frac{\pi_i}{\pi_i + \pi_j}$$

Pij is a probability that a person feels that Ai is unpleasant when the person compares between the pair of sample sounds (Ai, Aj). (1−Pij) is a probability that a person feels that the sound Aj is unpleasant. These probabilities can be obtained easily when a frequency that a person feels that the sample sound Ai is unpleasant is set as πi, and a frequency that a person feels that the sample sound Aj is unpleasant is πj. The probability Pij is statistically known to follow a binomial distribution. Therefore, when an assumption is established that an expectation value receives an influence in the psycho-acoustic characteristic, it is rational to use a multiplication model of the expression (k). As the multiple logistic regression model is used to estimate a population probability Pij, the estimated Pij becomes a value within a range from 0 to 1, and this value is rational as a reference mark.

Therefore, the present inventor sets the multiple logistic regression model as the sound quality evaluation model. Prior to the explanation about the derivation process of the sound quality evaluation model according to the present invention, the multiple logistic regression model will be briefly explained.

Loudness is one of causes of discomfort of sound generated from the image forming apparatus. To simplify the explanation, it is assumed that loudness is the cause of discomfort. In this case, n persons compare two sample sounds (A1, A2) to test which one of the sounds is unpleasant. When there is no difference in loudness between the two sounds, the probability that each one of A1 and A2 is unpleasant is 50 percent.

When loudness of the sound A2 is smaller than that of the sound A1 by 1 (sone), the probability that the sound A2 is felt unpleasant is assumed to become 25 percent. Further, when loudness of the sound A2 is smaller than that of the sound A1 by 2 (sone), the probability that the sound A2 is felt unpleasant becomes smaller by another 25 percent. The probability that the sound A2 is felt unpleasant cannot be considered to become zero percent. In other words, it is natural to consider as follows. The probability that the sound is felt unpleasant becomes 25 percent is not because loudness becomes smaller by 1 (sone). Instead, the probability that the sound is felt unpleasant changes from 50 percent to 25 percent, that is, the probability is halved, because loudness is decreased by 1 (sone). Therefore, it is natural to consider that the probability that the sound is felt unpleasant becomes 25×(½)=12.5 percent when loudness becomes smaller by 2 (sone).

As explained above, addition does not work but multiplication works in the sound quality improvement effect. When multiplication works, the employment of logarithm ln(p) makes addition work. In order to challenge the limit of 100 percent like a yield, −ln(1−p) may be used. A combination of two logarithms of $$z = \ln(p) - \ln(1-p) = \ln(p/1-p) \quad (\alpha)$$

is called a logit transformation. An inverse transformation is $$p = \exp(z)/(1+\exp(z)) = 1/(1+\exp(-z))$$

This means that when an S curve (i.e., a sigmoid function) is applied to the probability p from 0 to 1, this curve is approximated by a cumulative distribution function of a logistic distribution.

Figure 51:
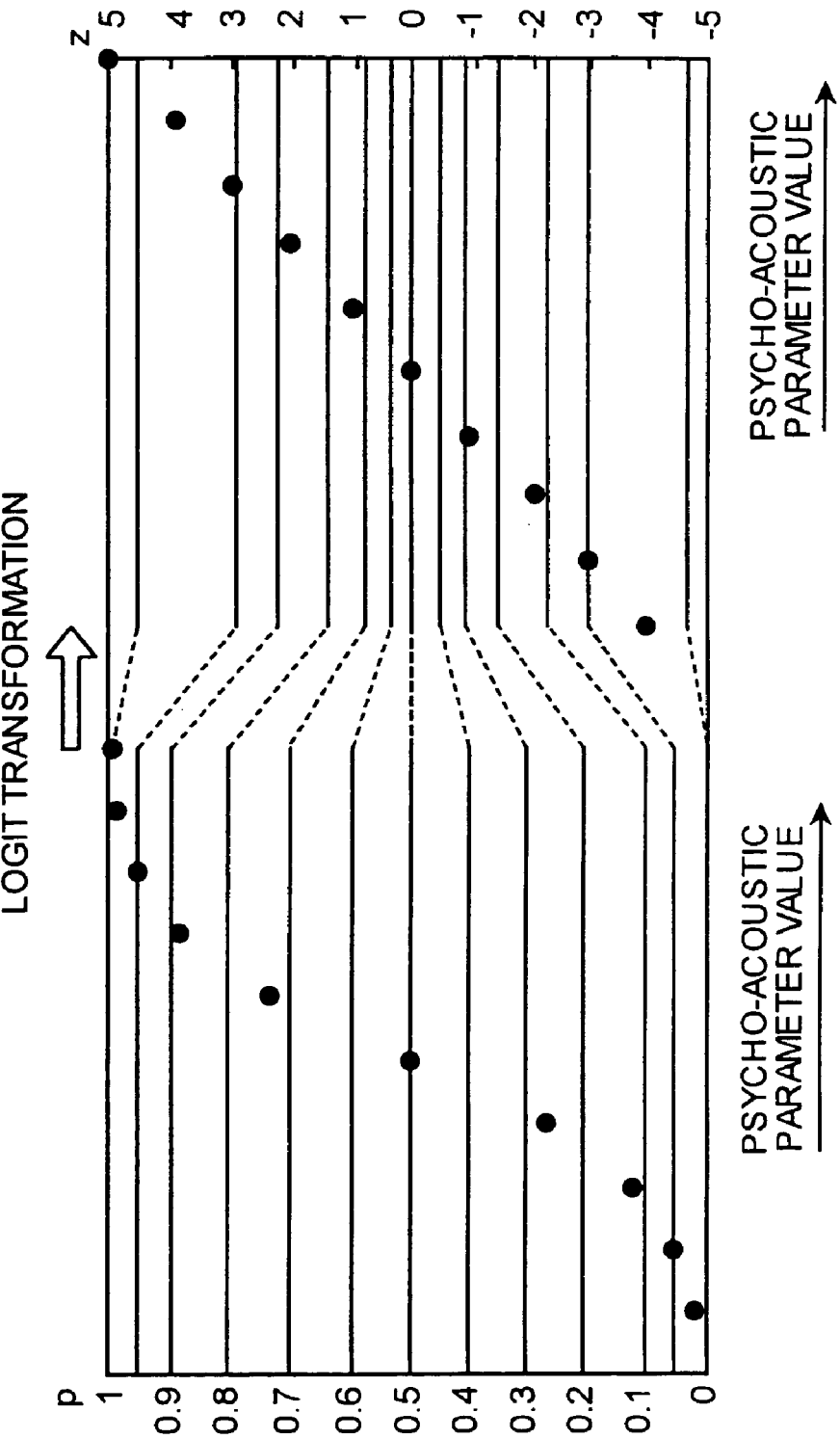
FIG. 51 is a graph for illustrating a logit transformation.

A graph shown in FIG. 51 expresses an effect of the logit transformation. As shown in FIG. 51, it is clear that the probability p is linear after the logit transformation. Therefore, z is used as a target variable, and a general regression analysis is carried out to estimate z. An estimate value of p can be obtained from the inverse transformation of the expression (a). In the estimation where p that expresses a defective fraction or a proportion is a target variable, p=r/n is logit transformed, and a regression analysis is carried out using this logit transformation as a target variable. This analysis is called a logistic regression analysis. r presents a number of defects, and n represents a number of inspection. When r is 0 or n, it is not possible to obtain z. Therefore, z is set as follows.

$$z = \ln((r+\tfrac{1}{2})/n(n-r+\tfrac{1}{2}))$$

This transformation is called an empirical logit.

In this transformation, both when n is a large value and when n is a small value, the processing is handled as equivalent. Therefore, weighting is necessary according to the size of z. Particularly, when the value of p is near 0 or 1, a variance of the logit z becomes large, which is inconvenient. The logistic regression analysis takes these points into consideration.

The above explains about the logistic regression analysis. The present inventor derives the sound quality evaluation expression using the logistic regression analysis, and carries out the sound quality evaluation using this evaluation expression. A process of the evaluation will be explained in detail based on an experiment actually carried out.

A flow of the sound quality evaluation experiment of the image forming apparatus and a derivation of a sound quality evaluation expression is as follows.

(2-1) Collection of operation noise of the image forming apparatus (2-2) Analysis of the operation noise (2-3) Creation of sample sound from the collected operation noise (2-4) Measurement of psycho-acoustic parameters of the sample sound (2-5) Pair comparison method experiment using the sample sound (2-6) Identification of a source of unpleasant noise (2-7) Preparation of analysis data of a differential model (2-8) Calculation of an expression to estimate a difference between scores (2-9) Deriving of a model expression (i.e., a sound quality evaluation expression) to estimate scores (2-10) Verification of a derived sound quality evaluation expression Details of the above process will be explained. The process of (2-1) Collection of operation noise of the image forming apparatus, the process of (2-2) Analysis of the operation noise, the process of (2-3) Creation of sample sound from the collected operation noise, the process of (2-4) Measurement of psycho-acoustic parameters of the sample sound, the process of (2-5) Pair comparison method experiment using the sample sound, and the process of (2-6) Identification of a source of unpleasant noise are similar to the processes of (1-1) to (1-6) respectively of the sound quality evaluation experiment described above. Therefore, the explanation of these processes will be omitted. The work of the process (2-7) and the subsequent processes are carried out using the experiment results similar to those obtained from the above experiment.

In the process of (2-5), it is preferable to carry out a comparative experiment including a different comparison order for all the pairs of combinations of the nine sample sounds. However, in order to decrease the number of times of experiment, the comparative experiment may be carried out for only pairs of sample sounds that are extracted.

In the pair comparison experiment, one of a pair of sample sounds is selected as unpleasant for the evaluation, and it is a condition that discomfort levels of the pair of sample sounds are not evaluated as about the same. The sound quality evaluation expression described later is obtained using the experiment data. A cumulative logistic regression model is used for the Scheffe's pair comparison method and its improved method (i.e., Haga's modified method, Ura's modified method, and Nakaya's modified method). The sound quality evaluation expression described below can be used for the Bradley-Terry model, and can be applied to any experiment data of the pair comparison method.

The process of (2-7) preparation of analysis data of a differential model will be explained next. The experiment result obtained from the pair comparison experiment in the process of (2-5), that is the same as the experiment in the process of (1-5), is used to obtain probabilities that each of the two sounds is felt unpleasant. More specifically, sound A (i.e., the sound presented earlier) is compared with sound B (i.e., the sound present later). The number of persons who feel that one of the sounds is unpleasant is divided by the total number of testers. Assume that the number of testers is forty. As a result of comparing the sound A (i.e., the sound presented earlier) with the sound B (i.e., the sound present later), 30 persons judge that the sound A is unpleasant, and 10 persons judge that the sound B is unpleasant. In this case, probabilities that the sound A is felt unpleasant and the sound B is felt unpleasant are obtained as follows.

The probability that the sound A is unpleasant=30/40, and the probability that the sound B is unpleasant=10/40.

The probabilities obtained like this are used to prepare a model of estimating a difference of probabilities between the two sounds that is used in the next process of (2-8) based on the difference of physical quantities (i.e., psycho-acoustic parameters) between two sounds. A difference of physical quantities (i.e., psycho-acoustic parameters) that is used to prepare the estimation model, that is, a difference of psycho-acoustic parameters (refer to Table 6) between the compared two sample sounds is calculated for all the combinations of sample sounds (i.e., 72 combinations for one mode, and 288 combinations for all the four modes).

Table 18 expresses a part of a result of a difference between calculated scores and a difference between psycho-acoustic parameters (i.e., analysis data of a differential model). Table 18 expresses a part of a result of the sample sounds (i.e., a result of the comparison between the sample sound (1) and the sample sound (2)) in the color mode (1).

TABLE 18

| Order of presentation I J | Difference of sound pressure level | Difference of loudness | Difference of sharpness | Difference of tonality | Difference of impulsiveness | Frequency that I (1) is unpleasant | Frequency that J (−1) is unpleasant | Difference between scores | Difference between subjective evaluation values | Probability that I is unpleasant | Probability that J is unpleasant | Number of testers |
|---|---|---|---|---|---|---|---|---|---|---|---|---|
| (1)–(2) | −5.70 | −1.95 | −0.42 | −0.01 | 0.05 | 2 | 33 | −31 | −0.886 | 0.06 | 0.94 | 35 |
| (2)–(1) | 5.70 | 1.95 | 0.42 | 0.01 | −0.05 | 27 | 8 | 19 | 0.543 | 0.77 | 0.23 | 35 |
| (1)–(3) | −1.80 | −1.37 | −0.76 | 0.08 | −0.04 | 8 | 27 | −19 | −0.543 | 0.23 | 0.77 | 35 |
| (3)–(1) | 1.80 | 1.37 | 0.76 | −0.08 | 0.04 | 23 | 12 | 11 | 0.314 | 0.66 | 0.34 | 35 |
| (1)–(4) | −2.85 | −0.90 | 0.21 | −0.01 | 0.04 | 10 | 25 | −15 | −0.429 | 0.29 | 0.71 | 35 |
| (4)–(1) | 2.85 | 0.90 | −0.21 | 0.01 | −0.04 | 25 | 10 | 15 | 0.429 | 0.71 | 0.29 | 35 |
| (1)–(5) | −3.50 | −1.04 | 0.14 | 0.04 | −0.21 | 8 | 27 | −19 | −0.543 | 0.23 | 0.77 | 35 |
| (5)–(1) | 3.50 | 1.04 | −0.14 | −0.04 | 0.21 | 24 | 11 | 13 | 0.371 | 0.69 | 0.31 | 35 |
| (1)–(6) | −3.55 | −0.38 | 0.01 | 0.07 | −0.37 | 8 | 27 | −19 | −0.543 | 0.23 | 0.77 | 35 |
| (6)–(1) | 3.55 | 0.38 | −0.01 | −0.07 | 0.37 | 24 | 11 | 13 | 0.371 | 0.69 | 0.31 | 35 |
| (1)–(7) | −3.45 | −0.26 | 0.17 | 0.05 | −0.02 | 26 | 9 | 17 | 0.486 | 0.74 | 0.26 | 35 |
| (7)–(1) | 3.45 | 0.26 | −0.17 | −0.05 | 0.02 | 11 | 24 | −13 | −0.371 | 0.31 | 0.69 | 35 |
| (1)–(8) | −8.70 | −2.85 | −0.93 | 0.01 | −0.24 | 2 | 33 | −31 | −0.886 | 0.06 | 0.94 | 35 |
| (8)–(1) | 8.70 | 2.85 | 0.93 | −0.01 | 0.24 | 32 | 3 | 29 | 0.829 | 0.91 | 0.09 | 35 |
| (1)–(9) | −4.85 | −2.13 | −0.45 | 0.02 | −0.14 | 3 | 32 | −29 | −0.829 | 0.09 | 0.91 | 35 |
| (9)–(1) | 4.85 | 2.13 | 0.45 | −0.02 | 0.14 | 33 | 2 | 31 | 0.886 | 0.94 | 0.06 | 35 |

The process of (2-8) calculation of an expression to estimate probabilities of two scores will be explained next. In this process, the probabilities of two sounds obtained in the process of (2-7) and the difference between physical quantities (i.e., psycho-acoustic parameters) are used to carry out a multiple logistic regression analysis.

The multiple logistic regression analysis can be carried out using statistical analysis software "JMP (a registered trademark of SAS Institute Inc.)", or "SPSS (a registered trademark of SPSS Inc.)". The data (i.e., discomfort probabilities and a difference between psycho-acoustic parameters) in Table 18 is input to JMP, and the analysis is carried out while selecting an explanatory variable (i.e., a difference between psycho-acoustic parameters). As a result, a statistical result of P values of the logistic regression coefficients and selected explanatory variables and contribution rates of the expression are output. The P value is a probability of a test of a significant difference. When the probability is 5 percent or less, the result is determined as significant. When the probability is above 5 percent, the result is determined as insignificant (i.e., irrelevant).

As the model used this time is for a difference between scores, the intercept is fixed to zero, and significant psychoacoustic parameters are selected according to statistical analysis software "JMP version 4J". As a result of the selection of variables, loudness, sharpness, tonality and impulsiveness are selected. Table 19 expresses partial regression coefficients (i.e., regression coefficients in the multiple linear regression analysis) of the four psycho-acoustic parameter that are selected as variables.

TABLE 19

| Item | Estimate value | Standard error | Chi-square | p value (Prob > ChiSq) | Lower side 95 percent | Higher side 95 percent |
|---|---|---|---|---|---|---|
| Loudness | 0.80742768 | 0.0214161 | 1421.4 | <.0001 | 0.76545285 | 0.84940259 |
| Sharpness | 1.38073296 | 0.0530017 | 678.64 | <.0001 | 1.27685159 | 1.48461447 |
| Tonality | 9.04860954 | 0.4772413 | 359.49 | <.0001 | 8.11323413 | 9.98398583 |
| Impulsiveness | 5.59160971 | 0.146311 | 1460.6 | <.0001 | 5.30484579 | 5.87837423 |

As shown in Table 19, the result of the regression analysis includes an upper limit value and a lower limit value of a partial regression coefficient having the reliability of 95 percent or above (i.e., a range of a partial regression coefficient having the reliability of 95 percent or above), in addition to the partial regression coefficients of the selected four parameters. The upper limit value and the lower limit value are obtained by adding or subtracting about two times of a corresponding standard deviation (i.e., $2\sigma$) to the estimate value of the partial regression coefficient. The partial regression coefficients take positive values. Therefore, it is known that when a difference between the parameters is larger in the positive direction, a difference between discomfort levels becomes larger.

A model expression that gives the following $-z$ within exp in the expression (k) is prepared using the result of the multiple logistic regression analysis.

$$z = \sum_{l=1}^{L} b_l(x_{li} - x_{lj}) \quad (1)$$

$z = +0.80742768 \times (x \text{ loudness } i - x \text{ loudness } j) +$ $1.3807 \times (x \text{ sharpness } i - x \text{ sharpness } j) +$ $9.0486 \times (x \text{ tonality } l - x \text{ tonality } j) +$ $5.5916 \times (x \text{ impulsiveness } i - x \text{ impulsiveness } j)$ By substituting the psycho-acoustic parameter values of two sounds as explained above, a nonlinear expression capable of calculating discomfort probabilities when the two sounds are compared is derived.

Figure 52:
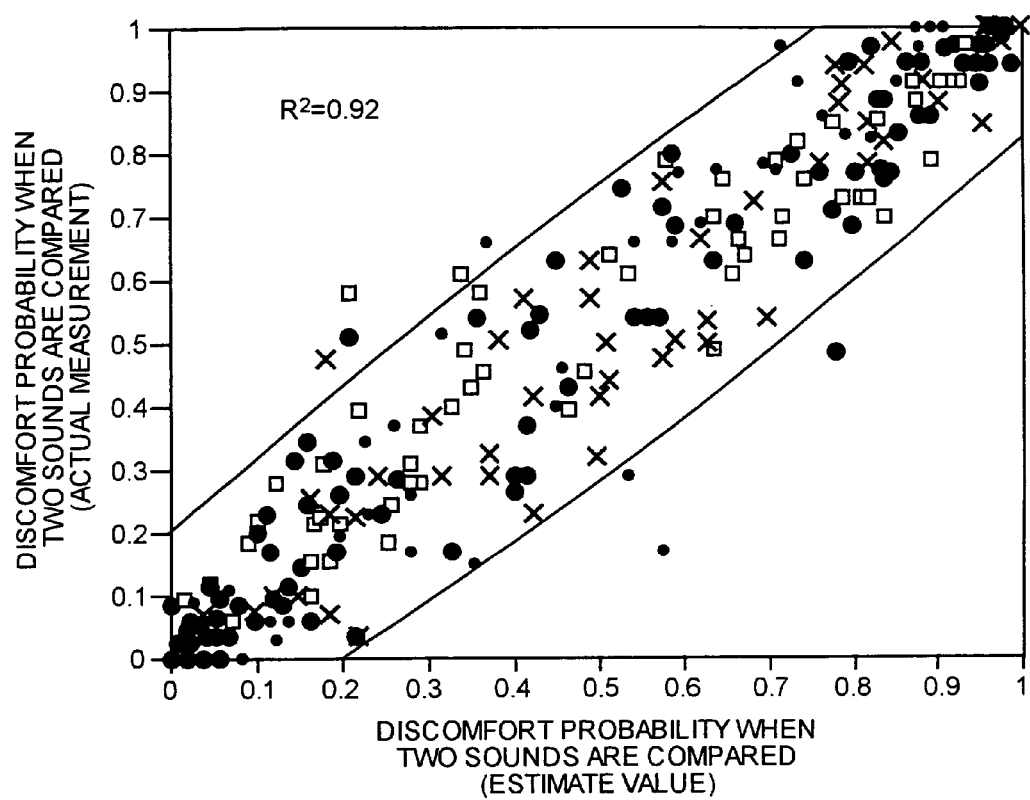
FIG. 52 is a plot of an estimate value derived from a model expression capable of calculating a difference between discomfort probabilities of obtained sound and an actual measurement in one process of the present invention.

FIG. 52 is a plot of an actual measurement of discomfort probabilities and an estimate value derived from the model expression when the two sounds are compared. It is clear that the discomfort contribution probability is as high as 92 percent, and the reliability of the model expression is high.

The process of (2-9) deriving of a sound quality evaluation expression to estimate discomfort probabilities will be explained next. While discomfort probabilities when two sounds are compared can be estimated, what is finally necessary in the sound quality evaluation is a discomfort probability of a single sound. A sound quality evaluation expression capable of estimating a relative discomfort probability from a population of one sound extracted is derived as follows.

First, an average of each sample sound that is used as each psycho-acoustic parameter in the experiment is substituted into the expression (1) of the expression (k). A discomfort probability when $p=0.5$, that is, a discomfort probability when the sound of each parameter value as an average is compared with other sound in the population is defined as "50 percent".

An average of each psycho-acoustic parameter is substituted to obtain the following result.

x loudness 0=7.067804
x sharpness 0=2.27953527947254
x tonality 0=0.115442108655561
x impulsiveness 0=0.606150659026989
Therefore, the following result is obtained.

$0.5 = 1/\{1 + \exp(-[+0.80742768(\text{loudness value } i - 7.067804) +$ $1.38073296 (\text{sharpness value } i - 2.27953527947254) +$ $9.04860954 (\text{tonality value } i - 0.115442108655561) +$ $5.59160971 (\text{impulsiveness value } i - 0.606150659026989)]\}$ When the contents of exp is z, $0.5 = 1/1 + \exp(-z)$ $0.5 \times \{1 + \exp(-z)\} = 1$ $0.5 \times \exp(-z) = 0.5$ $\exp(-z) = 1$ When both sides are expressed in logarithm, $\ln\{\exp(-z)\} = \ln 1 = 0$ $-z = 0$ $z = 0$ Therefore, $Z = 0 = [+0.80742768 (\text{loudness value } i - 7.067804) +$ $1.38073296 (\text{sharpness value } i - 2.27953527947254) +$ $9.04860954 (\text{tonality value } i - 0.115442108655561) +$ $5.59160971 (\text{impulsiveness value } i - 0.606150659026989)]\}$ Therefore $z = +0.80742768 \times \text{loudness value } i +$ $1.38073296 \times \text{sharpness value } i +$ $9.04860954 \times \text{tonality value } i +$ $5.59160971 \times \text{impulsiveness value } i - 13.28811895$ Accordingly, the expression is transformed into a model expression (i) capable of estimating a probability that discomfort of a single sample sound is felt.

The discomfort probability $P=1/(1+\exp(-z))$ $$z = +0.80742768 \times (\text{loudness}) + \qquad (i)$$
$$1.38073296 \times (\text{sharpness}) +$$
$$9.04860954 \times (\text{tonality}) +$$
$$5.59160971 \times (\text{impulsiveness}) - 13.28811895$$

The expression (i) derived in this way can be used as the sound quality evaluation expression to estimate the discomfort probability P.

While the average of all the data is used as a reference value, the reference value can be changed depending on an environmental change. A discomfort probability of the sound generated from the image forming apparatus after the improvement can also be calculated using a psycho-acoustic parameter value obtained from the sound generated from the image forming apparatus before the improvement.

The expression (i) derived above is used to estimate a change in the probability of relative merits due to a deviation from the average. A probability when the average of the physical quantity of sound is input is calculated as 0.5.

When this probability becomes larger, discomfort increases. A condition of a psycho-acoustic parameter when the probability P becomes equal to or smaller than a predetermined probability can be obtained from this sound quality expression.

From the above expression (i), it is clear that discomfort can be decreased when the sound element corresponding to each psycho-acoustic parameter is decreased, that is, when (1) the loudness is made smaller, (2) the higher-frequency component (sharpness) is decreased, (3) the pure tone component (tonality) is decreased, and (4) the impulse noise (impulsiveness) is decreased.

As explained in the process of (2-8), the partial regression coefficients have reliability of 95 percent or above that is obtained as a result of the regression analysis shown in Table 19. Therefore, a range of the intercept is also obtained by substituting the upper limit value and the lower limit value of each partial regression coefficient (i.e., the intercept when the lower limit value is substituted is −12.47284396, and the intercept when the upper limit value is substituted is −14.10339529).

When the above expression (i) is modified to take coefficients and an intercept within the above range, the following expression (f) is obtained.

The discomfort probability $P=1/(-1+\exp(-z))$ $$z = A \times (\text{loudness value}) + B \times (\text{sharpness value}) +$$
$$C \times (\text{tonality value}) + D \times (\text{impulsiveness value}) + E$$

$$0.76545285 \leq A \leq 0.84940259$$
$$1.27685159 \leq B \leq 1.48461447$$
$$8.11323413 \leq C \leq 9.98398583$$
$$5.30484579 \leq D \leq 5.87837423$$
$$-14.10339529 \leq E \leq -12.47284396 \qquad (f)$$

The above expression (f) can be used as the sound quality evaluation expression to estimate the probability R While the above expression (f) has a range of values that the regression coefficient can take based on the result shown in Table 19, $z \pm 2\sigma$ is a range of the reliability of 95 percent, when the estimate value of the regression coefficient shown in Table 19 is fixed (i.e., when the coefficient to be multiplied to each psycho-acoustic parameter is fixed). $\sigma$ is a standard deviation of error.

The standard deviation z is obtained as follows. First, z is derived from the expression ($\alpha$), and the statistical analysis software "JMP (a registered trademark of SAS Institute Inc.) or the like is used to estimate an estimate value of z. A relationship between z obtained from the actual measurement and the estimate value z is plotted in a scatter diagram. The above statistical analysis software is used to obtain the standard deviation of this difference (i.e., error).

As a result of carrying out the above work, the error standard deviation $\sigma=0.721307$ is obtained.

Therefore, the following expression (h) that includes this error range is obtained.

The discomfort probability $P=1/(1+\exp(-z\pm 2\sigma))$ $$z = +0.80742768 \times (\text{loudness}) + \qquad (h)$$
$$1.38073296 \times (\text{sharpness}) +$$
$$9.04860954 \times (\text{tonality}) +$$
$$5.59160971 \times (\text{impulsiveness}) - 13.28811895$$
$$\sigma = 0.721307$$

The above expression (h) can be used as the sound quality evaluation expression to estimate the discomfort probability P.

The discomfort probability can also be obtained from the following expression using the error standard deviation $\sigma$.

The discomfort probability $P=1/(1+\exp(-z))\pm 2\sigma$

When the discomfort probability is derived from this expression, the range of the derived discomfort probability P may exceed the range of 1 to 1, which is not proper as the expression to estimate the discomfort probability.

The process of (2-10) verification of a derived sound quality evaluation expression will be explained next. In this process, the estimation precision of the estimation expression (i.e., sound quality expression) of the derived discomfort probability P is tested.

The test is carried out by comparing the actual measurement of the discomfort probability P with the estimate value derived from the sound quality evaluation expression (i). Experiment must be actually carried out to obtain the actual measurement of the discomfort probability P for each operation mode. Therefore, experiment is carried out for each of the four modes of the color mode (1), the color mode (2), the monochrome mode, and the mixed mode, thereby obtaining the actual measurement of a discomfort probability. At the same time, the estimate values corresponding to these actual measurements are derived using the sound quality evaluation expression.

For the actual measurement of the discomfort probability, a value obtained by dividing the sum of the discomfort indices of each sample sound by the total number of evaluations is used. Specifically, in the experiment concerning the sample sound in the color mode (1), a denominator of the discomfort probability becomes as follows. When 35 persons carry out the experiment, each of nine sounds is compared with the other eight sounds for each sample sound. Therefore, the denominator becomes as follows:

Eight sounds×two (i.e., permutation of the order of comparison)×35 persons=560 persons On the other hand, the numerator becomes as follows. The sample sound (1) in the color mode (1) is taken as an example. When the numbers of persons who judge that the sample sound (1) is unpleasant as a result of comparing the sound (1) with the other sample sounds (2) to (9) (including an opposite order) are 10, 20, 20,19, 19, 50, 5, and 5, the sum 148 becomes the numerator.

Therefore, the actual measurement of the discomfort probability of the sample sound (1) in the color mode (1) is 48/560=0.26.

The actual measurement of the discomfort probability is obtained for each sample sound in each of the four modes in the above order. At the same time, the sound physical quantity (i.e., psycho-acoustic parameter) is substituted into the above sound quality evaluation expression (i), thereby obtaining an estimate value. The actual measured discomfort probability and the estimated probability of each sample sound in each mode can be obtained. Table 20 expresses the result of obtaining the probabilities.

Figure 53:
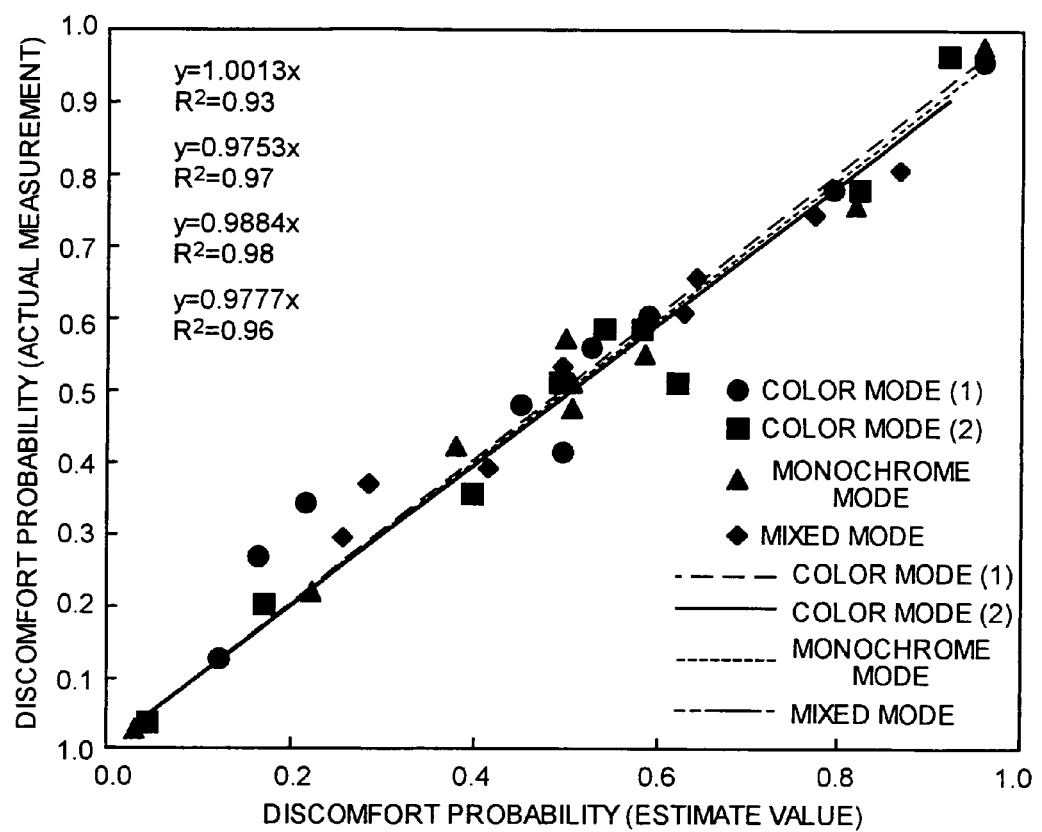
FIG. 53 is a plot of a comparison between an estimated discomfort probability derived from the sound quality evaluation expression according to the present invention and an actual measurement for each operation mode of the image forming apparatus.

FIG. 53 is a graph in which the above result is plotted. The inclination of the graph is approximately 1, and the contribution rate is high. Therefore, the precision of the estimate values of scores derived from the experiment expression (i) is considered to be high in any one of the four experiments, that is, in any one of the four modes.

In deriving the estimate value to carry out the test, an intercept (=E) is obtained from the average of the psycho-acoustic parameters for each experiment (i.e., for each mode). An expression obtained by modifying the expression (i) using this intercept is derived for each mode. The estimate value is obtained using this derived expression. This modification is carried out as it is necessary to test the precision of the estimate value by comparing the actual measurement according to each experiment with the estimate value. When the test is not carried out, this modification is not necessary, and the expression (i) can be used as the sound quality evaluation expression. Table 10 expresses the modified values for reference. When the value of the "difference from the total average" is added to the value of the intercept obtained by substituting the average in each mode, an expression similar to the expression (i) is obtained.

TABLE 20

| Sample sound | Loudness | Sharpness | Tonality | Impulsiveness | Logit (z) | Estimate probability | Actual probability | Reaction | Total frequency |
|---|---|---|---|---|---|---|---|---|---|
| Color_28 ppm_(1) | 5.38 | 1.89 | 0.14 | 0.42 | −1.6156 | 0.17 | 0.26 | 148 | 560 |
| Color_28 ppm_(2) | 7.33 | 2.32 | 0.15 | 0.38 | 0.376705 | 0.59 | 0.60 | 336 | 560 |
| Color_28 ppm_(3) | 6.75 | 2.66 | 0.06 | 0.46 | −0.00345 | 0.50 | 0.41 | 229 | 560 |
| Color_28 ppm_(4) | 6.29 | 1.68 | 0.16 | 0.38 | −1.29379 | 0.22 | 0.34 | 190 | 560 |
| Color_28 ppm_(5) | 6.42 | 1.75 | 0.10 | 0.63 | −0.19765 | 0.45 | 0.47 | 265 | 560 |
| Color_28 ppm_(6) | 5.77 | 1.88 | 0.07 | 0.79 | 0.113567 | 0.53 | 0.56 | 311 | 560 |
| Color_28 ppm_(7) | 5.64 | 1.72 | 0.09 | 0.45 | −1.99555 | 0.12 | 0.13 | 71 | 560 |
| Color_28 ppm_(8) | 8.23 | 2.82 | 0.13 | 0.67 | 3.241184 | 0.96 | 0.96 | 535 | 560 |
| Color_28 ppm_(9) | 7.51 | 2.34 | 0.13 | 0.57 | 1.374586 | 0.80 | 0.78 | 435 | 560 |
| Color_14 ppm_(1) | 5.91 | 2.28 | 0.18 | 0.60 | 0.183307 | 0.55 | 0.58 | 324 | 560 |
| Color_14 ppm_(2) | 6.19 | 1.96 | 0.25 | 0.59 | 0.505833 | 0.62 | 0.51 | 284 | 560 |
| Color_14 ppm_(3) | 5.08 | 2.74 | 0.05 | 0.77 | −0.01453 | 0.50 | 0.51 | 284 | 560 |
| Color_14 ppm_(4) | 7.19 | 2.60 | 0.19 | 0.73 | 2.50254 | 0.92 | 0.96 | 538 | 560 |
| Color_14 ppm_(5) | 6.02 | 2.50 | 0.16 | 0.80 | 1.558612 | 0.83 | 0.78 | 434 | 560 |
| Color_14 ppm_(6) | 4.76 | 1.60 | 0.13 | 0.90 | −0.40552 | 0.40 | 0.35 | 197 | 560 |
| Color_14 ppm_(7) | 4.10 | 1.79 | 0.11 | 0.50 | −3.08532 | 0.04 | 0.04 | 22 | 560 |
| Color_14 ppm_(8) | 6.63 | 2.66 | 0.21 | 0.38 | 0.346798 | 0.59 | 0.58 | 327 | 560 |
| Color_14 ppm_(9) | 5.39 | 2.08 | 0.15 | 0.45 | −1.59172 | 0.17 | 0.20 | 110 | 560 |
| Monochromatic_38 ppm_(1) | 8.52 | 2.47 | 0.06 | 0.65 | 0.040958 | 0.51 | 0.51 | 259 | 512 |
| Monochromatic_38 ppm_(2) | 8.92 | 2.00 | 0.09 | 0.65 | 0.039952 | 0.51 | 0.47 | 241 | 512 |
| Monochromatic_38 ppm_(3) | 7.98 | 2.96 | 0.05 | 0.67 | 0.358858 | 0.59 | 0.55 | 281 | 512 |
| Monochromatic_38 ppm_(4) | 10.73 | 2.79 | 0.07 | 0.80 | 3.239516 | 0.96 | 0.98 | 500 | 512 |
| Monochromatic_38 ppm_(5) | 8.76 | 2.69 | 0.07 | 0.80 | 1.519569 | 0.82 | 0.76 | 388 | 512 |
| Monochromatic_38 ppm_(6) | 7.47 | 1.86 | 0.05 | 0.86 | −0.47829 | 0.38 | 0.42 | 215 | 512 |
| Monochromatic_38 ppm_(7) | 6.16 | 2.00 | 0.07 | 0.45 | −3.46424 | 0.03 | 0.03 | 15 | 512 |
| Monochromatic_38 ppm_(8) | 9.13 | 2.83 | 0.08 | 0.43 | −2.1E−05 | 0.50 | 0.57 | 293 | 512 |
| Monochromatic_38 ppm_(9) | 8.48 | 2.22 | 0.08 | 0.45 | −1.25629 | 0.22 | 0.22 | 112 | 512 |
| Mixed (1) | 8.06 | 2.71 | 0.12 | 0.78 | 1.912288 | 0.87 | 0.80 | 425 | 425 |
| Mixed (2) | 8.99 | 1.85 | 0.18 | 0.66 | 1.241825 | 0.78 | 0.74 | 391 | 528 |
| Mixed (3) | 10.11 | 2.39 | 0.06 | 0.44 | 0.600783 | 0.65 | 0.65 | 345 | 528 |
| Mixed (4) | 8.49 | 2.36 | 0.12 | 0.56 | 0.534898 | 0.63 | 0.60 | 318 | 528 |
| Mixed (5) | 7.46 | 2.81 | 0.18 | 0.35 | −0.34275 | 0.42 | 0.39 | 205 | 528 |
| Mixed (6) | 6.53 | 1.80 | 0.06 | 0.84 | −0.90781 | 0.29 | 0.37 | 193 | 528 |
| Mixed (7) | 7.01 | 1.93 | 0.13 | 0.42 | −1.96995 | 0.12 | 0.12 | 65 | 528 |
| Mixed (8) | 6.00 | 2.29 | 0.17 | 0.76 | −0.0121 | 0.50 | 0.53 | 280 | 528 |
| Mixed (9) | 5.05 | 2.82 | 0.06 | 0.77 | −1.05718 | 0.26 | 0.29 | 154 | 528 |

TABLE 21

| | Loudness | Sharpness | Tonality | Impulsiveness | PPM | Intercept | Difference from total average (Adjusted value of logit z) |
|---|---|---|---|---|---|---|---|
| Total average | 7.07 | 2.28 | 0.12 | 0.61 | 26.7 | −13.2881 | 0.0000 |
| Color 28 ppm average | 6.59 | 2.12 | 0.11 | 0.53 | 28.0 | −12.2285 | −1.0597 |
| Color 14 ppm average | 5.70 | 2.25 | 0.16 | 0.64 | 14.0 | −12.6932 | −0.5949 |
| Monochrome 38 ppm average | 8.46 | 2.42 | 0.07 | 0.61 | 38.0 | −14.3867 | 1.0986 |
| Three-mode mixed average | 7.52 | 2.33 | 0.12 | 0.62 | 26.7 | −13.8442 | 0.5560 |

As is made clear in the above test, the precision of the estimate probability obtained from the sound quality expression (i) is considered high. It is necessary to confirm at what level of the discomfort probability P a person feels the sound unpleasant. The following experiment is carried out to confirm this. After each tester hears all the sample sounds (1) to (9), the tester hears each sound again and evaluates discomfort of each sample sound at three stages. Table 22, Table 23, and Table 24 express results obtained from this experiment. Table 22 expresses the result of the experiment carried out for the sample sound in the color mode (1). Table 23 expresses the result of the experiment carried out for the sample sound in the color mode (2). Table 24 expresses the result of the experiment carried out for the sample sound in the monochrome mode.

TABLE 22

| Sample sound | Actual measurement discomfort probability | Estimate discomfort probability in Table 20 | Estimate discomfort probability according to expression (i) | Score |
|---|---|---|---|---|
| Color 28 ppm (8) | 0.96 | 0.96 | 0.90 | C |
| Color 28 ppm (9) | 0.78 | 0.80 | 0.58 | C |
| Color 28 ppm (2) | 0.60 | 0.59 | 0.34 | C |
| Color 28 ppm (6) | 0.56 | 0.53 | 0.28 | B |
| Color 28 ppm (5) | 0.47 | 0.45 | 0.22 | B |
| Color 28 ppm (3) | 0.41 | 0.50 | 0.26 | A |
| Color 28 ppm (4) | 0.34 | 0.22 | 0.09 | A |
| Color 28 ppm (1) | 0.26 | 0.17 | 0.06 | A |
| Color 28 ppm (7) | 0.13 | 0.12 | 0.04 | A |

TABLE 23

| Sample sound | Actual measurement discomfort probability | Estimate discomfort probability in Table 20 | Estimate discomfort probability according to expression (i) | Score |
|---|---|---|---|---|
| Color 14 ppm (4) | 0.96 | 0.92 | 0.87 | C |
| Color 14 ppm (5) | 0.78 | 0.83 | 0.72 | C |
| Color 14 ppm (1) | 0.58 | 0.55 | 0.40 | C |
| Color 14 ppm (8) | 0.58 | 0.59 | 0.44 | C |
| Color 14 ppm (2) | 0.51 | 0.62 | 0.48 | C |
| Color 14 ppm (3) | 0.51 | 0.50 | 0.35 | B |
| Color 14 ppm (6) | 0.35 | 0.40 | 0.27 | B |
| Color 14 ppm (9) | 0.20 | 0.17 | 0.10 | A |
| Color 14 ppm (7) | 0.04 | 0.04 | 0.02 | A |

TABLE 24

| Sample sound | Actual measurement discomfort probability | Estimate discomfort probability in Table 20 | Estimate discomfort probability according to expression (i) | Score |
|---|---|---|---|---|
| Color 38 ppm (4) | 0.98 | 0.96 | 0.99 | C |
| Color 38 ppm (5) | 0.76 | 0.82 | 0.93 | C |
| Color 38 ppm (8) | 0.57 | 0.50 | 0.75 | C |
| Color 38 ppm (3) | 0.55 | 0.59 | 0.81 | C |
| Color 38 ppm (1) | 0.51 | 0.51 | 0.76 | B |
| Color 38 ppm (2) | 0.47 | 0.51 | 0.76 | B |
| Color 38 ppm (6) | 0.42 | 0.38 | 0.65 | B |
| Color 38 ppm (9) | 0.22 | 0.22 | 0.46 | A |
| Color 38 ppm (7) | 0.03 | 0.03 | 0.09 | A |

In the tables, "A" represents an evaluation that the sound is permissible. "C" represents an evaluation that the sound is not permissible. "B" represents an evaluation that the sound is between permissible and not permissible. When a largest value among the sound quality evaluation values that are evaluated as "A" (i.e., values calculated by the expression (i)) is a tolerance, a tolerance for each ppm and for each image forming speed (mm/s) in each mode is obtained as shown in Table 25.

TABLE 25

| ppm | Image forming speed (mm/s) | Tolerance |
|---|---|---|
| Color 14 ppm | 62.5 | 0.10 |
| Color 28 ppm | 125.0 | 0.26 |
| Monochrome 38 ppm | 185.0 | 0.46 |

Figure 54:
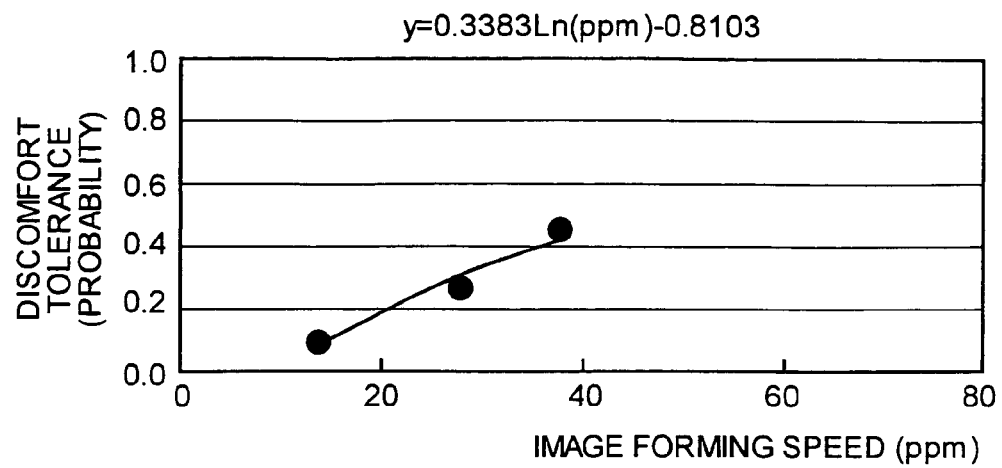
FIG. 54 is a graph of a relationship between an image forming speed in ppm value obtained from a result of an experiment and a tolerance of an index derived from the sound quality evaluation expression.

FIG. 54 is a graph of an approximate relationship between a ppm value and a tolerance based on the result shown in Table 25.

This approximate expression is as follows.

$$P \leq 0.3383 \, Ln(ppm) - 0.8103 \tag{g}$$

Figure 55:
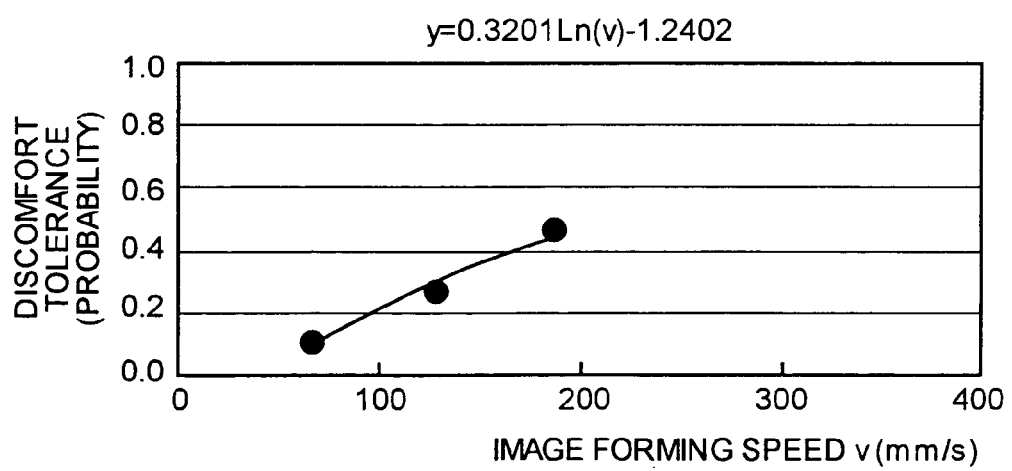
FIG. 55 is a graph of a relationship between an image forming speed in mm/s obtained from a result of an experiment and the tolerance of an index derived from the sound quality evaluation expression.

FIG. 55 is a graph of an approximate relationship between an image forming speed (mm/s) and a tolerance based on the results shown in Table 25. The approximate expression is as follows.

$$P \leq 0.3201 \, Ln(mm/s) - 1.2402 \tag{j}$$

As explained above, when the expression (i), (h), or (f) is used, the discomfort probability P can be obtained as the evaluation of discomfort by only obtaining psycho-acoustic parameter values that can be derived from the physical quantity of sound, without actually carrying out a subjective evaluation experiment. From the expression (g) or (j), the discomfort probability P in which discomfort is not felt can be determined in each mode, even if the apparatus has a plurality of operation modes having different image forming speeds (mm/s or ppm).

The above explains about the method of evaluating the quality of sound generated from the image forming apparatus by using the discomfort probability P and the method of deriving the sound quality evaluation expression that is used to evaluate the sound quality.

As explained above, the image forming apparatus may be modified by evaluating the sound quality after obtaining the discomfort probability P, evaluating noise that the image forming apparatus generates, and decreasing discomfort that the noise gives to a person based on a result of the evaluation.

First, sound generated from the image forming apparatus is collected according to a method similar to that used in the process (4), in order to evaluate the sound generated from the image forming apparatus. Sound is collected at a position where a person is present nearby (see FIG. 11) as prescribed in the ISO7779. This position is at a distance of 1.00±0.03 meters from a projection of a horizontal plane of a reference box, at a height of 1.2±0.03 meters or 1.50±0.03 meters from the top of the desk.

Further, as shown in FIG. 9, sounds may be collected from all the four sides of the front surface, the left and right surfaces, and the back surface of the operation unit. Psycho-acoustic parameters are obtained from each result of collection, and the discomfort probability P is obtained from the sound quality evaluation expression. Then, it is determined whether the discomfort probability P on each surface is within a tolerance. Alternatively, the discomfort probability P may be obtained from a result of the collection of sound from only the front surface or any one surface, and a decision is made. Alternatively, an average of psycho-acoustic parameter values obtained from the sounds collected from the four sides may be derived. Then, it is determined whether the discomfort probability P obtained from this average is within a tolerance.

In order to enable all persons at the four surface sides to feel no discomfort, it is preferable to collect sounds at all positions of the four surface sides. Sufficient evaluation can also be carried out when noise is collected at only the front surface side where there is a highest probability that a person is present.

When the discomfort probability P obtained in the above method exceeds the tolerance, there is a high risk that a person feels unpleasant. Therefore, in this case, various kinds of modifying are provided to units of the apparatus so as to make the discomfort probability P equal to or smaller than the tolerance. On the other hand, when the discomfort probability P is equal to or smaller than the tolerance, there is a small risk that a person feels unpleasant. Therefore, in this case, it can be determined that a noise countermeasure is not particularly necessary.

As described above, the discomfort probability P can be made smaller by making loudness smaller, decreasing the high-frequency component (sharpness), decreasing the pure tone component (tonality), and decreasing impulse noise (impulsiveness). When the discomfort probability P is made smaller, discomfort that is given to a person can be decreased.

In order to decrease the above psycho-acoustic parameters, a countermeasure similar to the one taken to remodel the apparatus based on the sound quality evaluation using the index S can be employed (see FIG. 32 to FIG. 48).

The present inventor measures the sound generated from the image forming apparatus that is provided with the above countermeasure in a condition similar to that used to measure the sound generated from the image forming apparatus before the countermeasure is provided. The inventor investigates the effect of the countermeasure based on a result of the measurement. The results of the measurement to be compared are obtained when the sound is collected from the front surface side of the image forming apparatus when each image forming apparatus is operated in the color mode (1).

Figure 56:
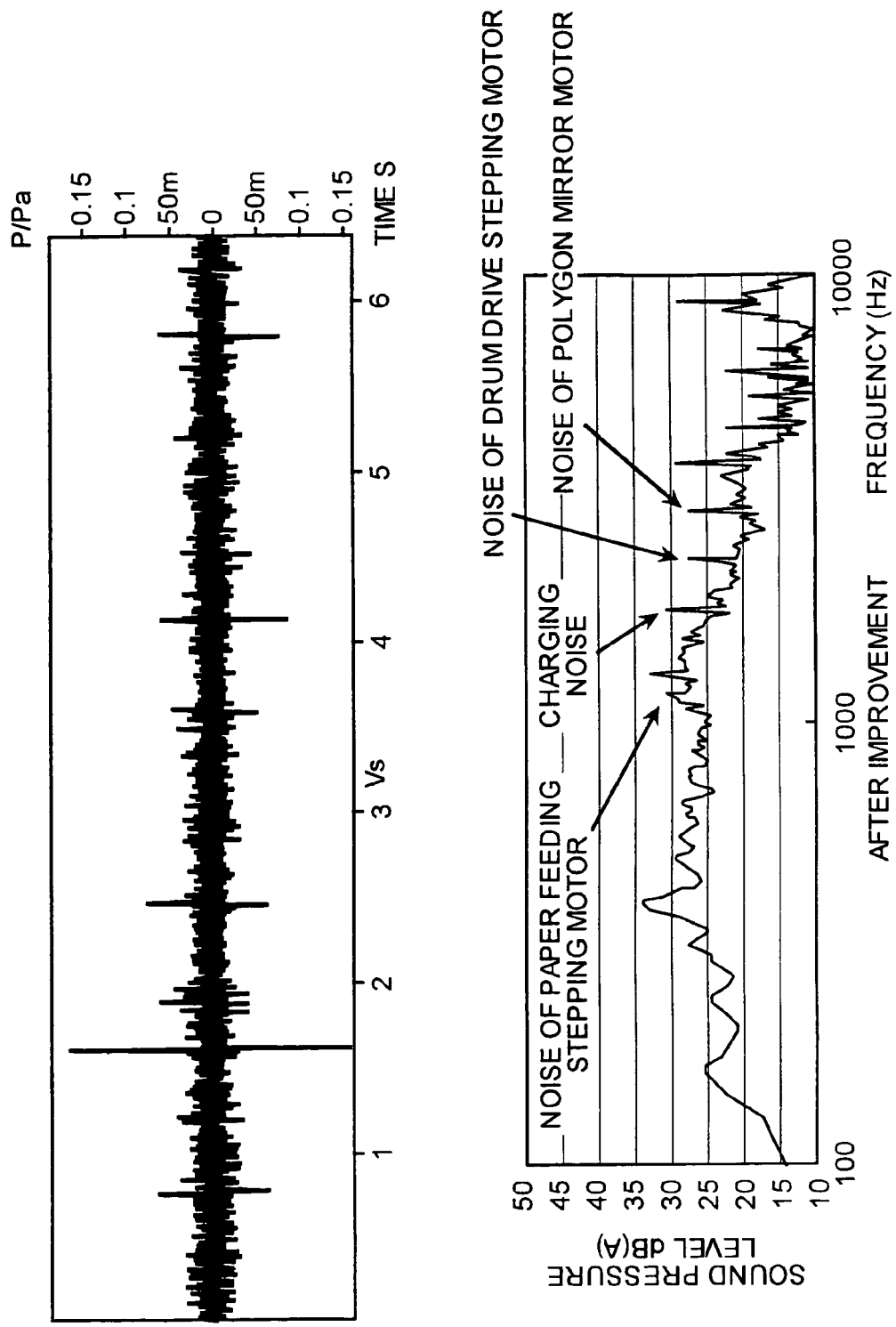
FIG. 56 is a graph of a result of analyzing sound generated from the image forming apparatus with a countermeasure following the modifying method according to the present invention.

FIG. 56 is a graph of a result of analyzing the noise after taking countermeasures. In comparing the noise analysis result after taking the countermeasures with the analysis result before taking the countermeasures (see FIG. 11), the following result is obtained. The noise of the paper feeding stepping motor is decreased by about 10 decibels, the charging noise is decreased by about 5 decibels, the noise of the drum driving motor is decreased by about 8 decibels, and the noise of the polygon mirror motor is also decreased by about 10 decibels. The fixing oil applying noise is not generated. From the above, it is clear that the sound generated from each source sound source can be decreased by taking the above countermeasures.

Table 26 expresses a result of the comparison between the psycho-acoustic parameter values obtained from the measurement results of before and after taking the countermeasures and the sound quality evaluation values derived from the sound quality evaluation expression (i).

TABLE 26

|  | Sound pressure level | Loudness | Sharpness | Tonality | Impulsiveness | Sound quality evaluation value according to expression (i) |
| --- | --- | --- | --- | --- | --- | --- |
| Before countermeasures | 52.2 | 7.51 | 2.34 | 0.13 | 0.57 | 0.59 |
| After countermeasures | 49.0 | 6.53 | 2.48 | 0.09 | 0.46 | 0.23 |

As is clear from Table 26, the sound quality evaluation value after taking the countermeasures, that is, discomfort probability is "−0.23", which is smaller than a tolerance "−0.26" in the color mode (1) shown in Table 14. Therefore, taking the above countermeasures is considered to remodel the image forming apparatus with little discomfort.

The present invention provides an image forming apparatus that evaluates the sound quality of the image forming apparatus using the sound quality evaluation expression as derived above, and that makes the evaluation result (i.e., discomfort probability P) satisfy a predetermined condition. Therefore, the present invention can be applied to develop and manufacture a new product as shown in a flowchart shown in FIG. 57.

Specifically, a configuration of each unit of the image forming apparatus is designed (at step S11: design process) such that the sound quality evaluation (i.e., discomfort probability P) according to the above sound quality evaluation expression satisfies the above condition. Then, the image forming apparatus is manufactured according to the design contents that are provided such that the discomfort probability P obtained from the sound generated from the image forming apparatus satisfies the above condition (step S12: manufacturing process). Through the above manufacturing process, the image forming apparatus that generates little unpleasant noise can be manufactured. This image forming apparatus can be provided to users.

As explained above, the index S that is derived from the sound quality evaluation expression (a) using the psycho-acoustic parameter values obtained from the sound generated from the image forming apparatus is structured to coincide with the condition (b) corresponding to the output numerical value of sheets on which an image is formed per minute. With this arrangement, the discomfort that the sound generated from the image forming apparatus gives to a person can be decreased. The condition (b) changes depending on the output value of sheets on which the image is formed. Therefore, when the image forming apparatus has the output value, that is, a plurality of operation modes, and when the image forming speed of the apparatus changes depending on the mode, the index S of the parameter values obtained from the operation noise can be obtained using the sound quality evaluation expression (a). As the index S satisfies a condition that the index S changes corresponding to the speed, there is an effect that the discomfort that the operation noise gives to the user can be decreased even when the apparatus operates in any mode.

Further, the index S that is derived from the sound quality evaluation expression (a) using the psycho-acoustic parameter values obtained from the sound generated from the image forming apparatus is structured to coincide with the condition (d) corresponding to the image forming speed. With this arrangement, the discomfort that the sound generated from the image forming apparatus gives to a person can be decreased. The condition (d) changes depending on the image forming speed. Therefore, when the image forming apparatus has a plurality of operation modes, and when the image forming speed of the apparatus changes depending on the mode, the index S of the parameter values obtained from the operation noise can be obtained using the sound quality evaluation expression (a). As the index S also satisfies a condition that the index S changes corresponding to the speed, there is an effect that the discomfort that the operation noise gives to the user can be decreased even when the apparatus operates in any mode.

Further, according to the present invention, the expression concerning a relationship between the difference between scores of the sound and a difference between psycho-acoustic parameter values is obtained first. The sound quality evaluation expression to estimate the sound evaluation itself is derived from this expression. Therefore, the sound quality evaluation expression in high precision can be derived without carrying out a relatively large number of experiments. As a result, there is an effect that the work concerning the sound quality evaluation is simplified.

Further, according to the present invention, the expression concerning a relationship between the probabilities of two sounds and a difference between the psycho-acoustic parameter values is obtained first. The sound quality evaluation expression to estimate the sound evaluation itself is derived from this expression. Therefore, the sound quality evaluation expression in high precision can be derived without carrying out a relatively large number of experiments. As a result, there is an effect that the work concerning the sound quality evaluation is simplified.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An image forming apparatus that forms an image onto a recording medium, wherein
a discomfort index S calculated from an equation $$S = A \times (\text{loudness value}) + B \times (\text{sharpness value}) + C \times (\text{tonality value}) + D \times (\text{impulsiveness value}) + E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln(ppm)} - 2.1364$$

where $14 \leq \text{ppm} \leq 38$ Ln indicates natural log, and ppm is an output number of the recording medium per minute with A4 size in horizontal direction, wherein the sound is collected at a listening position approximately one meter from an edge of the image forming apparatus.

2. The image forming apparatus according to claim 1, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the index S satisfies the inequality in any one of the operation modes.

3. The image forming apparatus according to claim 1, wherein
the listening position is based on the International Organization for Standardization 7779, and
the index S obtained from a sound collected from at least front direction of the image forming apparatus satisfies the inequality.

4. The image forming apparatus according to claim 1, wherein
the listening position is based on the International Organization for Standardization 7779, and
an average of the index S's obtained from sounds collected from front, rear, left, and right directions of the apparatus satisfies the condition.

5. The image forming apparatus according to claim 1, wherein
the listening position is based on the International Organization for Standardization 7779, and
the index S obtained from a sound collected from at least one direction among front, rear, left, and right directions of the image forming apparatus satisfies the inequality.

6. The image forming apparatus according to claim 1, wherein
the listening position is based on the International Organization for Standardization 7779, and
the index S obtained from a sound collected from each of front, rear, left, and right directions of the image forming apparatus satisfies the inequality.

7. The image forming apparatus according to claim 1, comprising:
a decreasing unit that decreases the sound generated from the image forming apparatus when forming an image onto the recording medium.

8. The image forming apparatus according to claim 7, further comprising:
a stepping motor that drives predetermined parts of the image forming apparatus when forming an image onto the recording medium; and
a bracket member that holds the stepping motor, wherein
the decreasing unit includes an elastic material disposed between the stepping motor and the bracket member.

9. The image forming apparatus according to claim 7, further comprising:
a stepping motor that drives predetermined parts of the image forming apparatus when forming an image onto the recording medium, wherein
the decreasing unit includes a drive control unit that drives the stepping motor in micro-step.

10. The image forming apparatus according to claim 7, further comprising:
a motor that drives predetermined parts of the image forming apparatus when forming an image onto the recording medium, wherein
the decreasing unit includes a Helmholtz resonator that is disposed near the motor.

11. The image forming apparatus according to claim 7, further comprising:
an image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

12. The image forming apparatus according to claim 1, comprising:
a guide member including a flexible sheet that guides the recording medium along a predetermined feeding path, wherein an edge of the guide member is a bent portion of the flexible sheet, wherein the edge is in contact with the recording medium fed.

13. The image forming apparatus according to claim 1, wherein a toner used to form an image onto the recording medium contains wax.

14. An image forming apparatus that forms an image onto a recording medium, wherein
a discomfort index S calculated from an equation $$S=A\times(\text{loudness value})+B\times(\text{sharpness value})+C\times(\text{tonality value})+D\times(\text{impulsiveness value})+E$$

where A=0.2347697, B=0.3847411, C=2.6283418, D=1.5681529, and E=−3.790295483, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln}(\text{ppm}) - 2.1364$$

where $14 \leq \text{ppm} \leq 38$ Ln indicates natural log, and ppm is an output number of the recording medium per minute with A4 size in horizontal direction, wherein the sound is collected at a listening position approximately one meter from an edge of the image forming apparatus.

15. The image forming apparatus according to claim 14, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the index S satisfies the inequality in any one of the operation modes.

16. The image forming apparatus according to claim 14, wherein the listening position is based on the International Organization for Standardization 7779, and
the index S obtained from a sound collected from at least front direction of the image forming apparatus satisfies the inequality.

17. The image forming apparatus according to claim 14, wherein
the listening position is based on the International Organization for Standardization 7779, and
an average of the index S's obtained from sounds collected from front, rear, left, and right directions of the apparatus satisfies the condition.

18. The image forming apparatus according to claim 14, wherein
the listening position is based on the International Organization for Standardization 7779, and
the index S obtained from a sound collected from at least one direction among front, rear, left, and right directions of the image forming apparatus satisfies the inequality.

19. The image forming apparatus according to claim 14, wherein
the listening position is based on the International Organization for Standardization 7779, and
the index S obtained from a sound collected from each of front, rear, left, and right directions of the image forming apparatus satisfies the inequality.

20. The image forming apparatus according to claim 14, comprising:
a decreasing unit that decreases the sound generated from the image forming apparatus when forming an image onto the recording medium.

21. The image forming apparatus according to claim 20, further comprising:
a stepping motor that drives predetermined parts of the image forming apparatus when forming an image onto the recording medium; and
a bracket member that holds the stepping motor, wherein
the decreasing unit includes an elastic material disposed between the stepping motor and the bracket member.

22. The image forming apparatus according to claim 20, further comprising:
a stepping motor that drives predetermined parts of the image forming apparatus when forming an image onto the recording medium, wherein
the decreasing unit includes a drive control unit that drives the stepping motor in micro-step.

23. The image forming apparatus according to claim 20, further comprising:
a motor that drives predetermined parts of the image forming apparatus when forming an image onto the recording medium, wherein
the decreasing unit includes a Helmholtz resonator that is disposed near the motor.

24. The image forming apparatus according to claim 20, further comprising:
an image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

25. The image forming apparatus according to claim 14, comprising:
a guide member including a flexible sheet that guides the recording medium along a predetermined feeding path, wherein
an edge of the guide member is a bent portion of the flexible sheet, wherein the edge is in contact with the recording medium fed.

26. The image forming apparatus according to claim 14, wherein a toner used to form an image onto the recording medium contains wax.

27. An image forming apparatus that forms an image onto a recording medium, wherein
a discomfort index S calculated from an equation $$S = A \times (\text{loudness value}) + B \times (\text{sharpness value}) C \times (\text{tonality value}) D \times (\text{impulsiveness value}) E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.532 \ln(v) - 2.8381$$

where $62.5 \leq v \leq 185$, ln indicates natural log, and v is a speed of forming an image onto the recording medium in millimeters per second, wherein the sound is collected at a listening position approximately one meter from an edge of the image forming apparatus.

28. The image forming apparatus according to claim 27, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the index S satisfies the inequality in any one of the operation modes.

29. The image forming apparatus according to claim 27, wherein the listening position is based on the International Organization for Standardization 7779, and
the index S obtained from a sound collected from at least front direction of the image forming apparatus satisfies the inequality.

30. The image forming apparatus according to claim 27, wherein the listening position is based on the International Organization for Standardization 7779, and
an average of the index S's obtained from sounds collected from front, rear, left, and right directions of the apparatus satisfies the condition.

31. The image forming apparatus according to claim 27, wherein
the listening position is based on the International Organization for Standardization 7779, and
the index S obtained from a sound collected from at least one direction among front, rear, left, and right directions of the image forming apparatus satisfies the inequality.

32. The image forming apparatus according to claim 27, wherein the listening position is based on the International Organization for Standardization 7779, and
the index S obtained from a sound collected from each of front, rear, left, and right directions of the image forming apparatus satisfies the inequality.

33. The image forming apparatus according to claim 27, comprising:
a decreasing unit that decreases the sound generated from the image forming apparatus when forming an image onto the recording medium.

34. The image forming apparatus according to claim 33, further comprising:
a stepping motor that drives predetermined parts of the image forming apparatus when forming an image onto the recording medium; and
a bracket member that holds the stepping motor, wherein
the decreasing unit includes an elastic material disposed between the stepping motor and the bracket member.

35. The image forming apparatus according to claim 33, further comprising:
a stepping motor that drives predetermined parts of the image forming apparatus when forming an image onto the recording medium, wherein the decreasing unit includes a drive control unit that drives the stepping motor in micro-step.

36. The image forming apparatus according to claim 33, further comprising:
a motor that drives predetermined parts of the image forming apparatus when forming an image onto the recording medium, wherein
the decreasing unit includes a Helmholtz resonator that is disposed near the motor.

37. The image forming apparatus according to claim 33, further comprising:
an image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

38. The image forming apparatus according to claim 27, comprising:
a guide member including a flexible sheet that guides the recording medium along a predetermined feeding path, wherein an edge of the guide member is a bent portion of the flexible sheet, wherein the edge is in contact with the recording medium fed.

39. The image forming apparatus according to claim 27, wherein a toner used to form an image onto the recording medium contains wax.

40. An image forming apparatus that forms an image onto a recording medium, wherein p1 a discomfort index S calculated from an equation $$S=A\times(\text{loudness value})+B\times(\text{sharpness value})+C\times(\text{tonality value})+D\times(\text{impulsiveness value})+E$$

where A=0.2347697, B=0.3847411, C=2.6283418, D1.5681529, and E=−3.790295483, using loudness, sharpness, tonality, and impulsiveness of a psycho-acoustic parameter obtained from a sound generated from the image forming apparatus when forming an image onto the recording medium satisfies an inequality $$S \leq 0.532 \ln(v) - 2.8381$$

where $62.5 \leq v \leq 185$, ln indicates natural log, and v is a speed of forming an image onto the recording medium in millimeters per second, wherein the sound is collected at a listening position approximately one meter from an edge of the image forming apparatus.

41. The image forming apparatus according to any one of claims 1 to 4, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the index S satisfies the inequality in any one of the operation modes.

42. The image forming apparatus according to any one of claims 1 to 4, wherein
the listening position is based on the International Organization for Standardization 7779, and
the index S obtained from a sound collected from at least front direction of the image forming apparatus satisfies the inequality.

43. The image forming apparatus according to any one of claims 1 to 4, wherein the listening position is based on the International Organization for Standardization 7779, and
an average of the index S's obtained from sounds collected from front, rear, left, and right directions of the apparatus satisfies the condition.

44. The image forming apparatus according to any one of claims 1 to 4, wherein
the listening position is based on the International Organization for Standardization 7779, and
the index S obtained from a sound collected from at least one direction among front, rear, left, and right directions of the image forming apparatus satisfies the inequality.

45. The image forming apparatus according to any one of claims 1 to 4, wherein
the listening position is based on the International Organization for Standardization 7779, and
the index S obtained from a sound collected from each of front, rear, left, and right directions of the image forming apparatus satisfies the inequality.

46. The image forming apparatus according to any one of claims 1 to 4, comprising:
a decreasing unit that decreases the sound generated from the image forming apparatus when forming an image onto the recording medium.

47. The image forming apparatus according to claim 10, further comprising:
a stepping motor that drives predetermined parts of the image forming apparatus when forming an image onto the recording medium; and
a bracket member that holds the stepping motor, wherein the decreasing unit includes an elastic material disposed between the stepping motor and the bracket member.

48. The image forming apparatus according to claim 10, further comprising:
a stepping motor that drives predetermined parts of the image forming apparatus when forming an image onto the recording medium, wherein the decreasing unit includes a drive control unit that drives the stepping motor in micro-step.

49. The image forming apparatus according to claim 10, further comprising:
a motor that drives predetermined parts of the image forming apparatus when forming an image onto the recording medium, wherein
the decreasing unit includes a Helmholtz resonator that is disposed near the motor.

50. The image forming apparatus according to claim 10, further comprising:
an image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

51. The image forming apparatus according to any one of claims 1 to 4, comprising:
a guide member including a flexible sheet that guides the recording medium along a predetermined feeding path, wherein
an edge of the guide member is a bent portion of the flexible sheet, wherein the edge is in contact with the recording medium fed.

52. The image forming apparatus according to any one of claims 1 to 4, wherein a toner used to form an image onto the recording medium contains wax.

53. A method of manufacturing an image forming apparatus that forms an image onto a recording medium, the method comprising:
designing the image forming apparatus so that a discomfort index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln(ppm)} - 2.1364$$

where $14 \leq \text{ppm} \leq 38$, Ln indicates natural log, and ppm is an output number of the recording medium per minute with A4 size in horizontal direction, wherein the sound is collected at a listening position approximately one meter from an edge of the image forming apparatus to be fabricated; and manufacturing the image forming apparatus based on a result of the designing.

54. A method of manufacturing an image forming apparatus that forms an image onto a recording medium, the method comprising:

designing the image forming apparatus so that an a discomfort index S calculated from an equation $$S=A\times(\text{loudness value})+B\times(\text{sharpness value})+C\times(\text{tonality value})+D\times(\text{impulsiveness value})+E$$

where A=0.2347697, B=0.3847411, C=2.6283418, D=1.5681529, and E=−3.790295483, using loudness, sharpness, tonality, and impulsiveness of a psycho-acoustic parameter obtained from a sound generated from the image forming apparatus when forming an image onto the recording medium satisfies an inequality $$S \leq 0.5664 \text{Ln}(\text{ppm}) - 2.1364$$

where $14 \leq \text{ppm} \leq 38$, Ln indicates natural log, and ppm is an output number of the recording medium per minute with A4 size in horizontal direction, wherein the sound is collected at a listening position approximately one meter from an edge of the image forming apparatus to be fabricated; and manufacturing the image forming apparatus based on a result of the designing.

55. A method of manufacturing an image forming apparatus that forms an image onto a recording medium, the method comprising:

designing the image forming apparatus so that a discomfort index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S \leq 0.532 \ln(v) - 2.8381$$

where $62.5 \leq v \leq 185$, ln indicates natural log, and v is a speed of forming an image onto the recording medium in millimeters per second, wherein the sound is collected at a listening position approximately one meter from an edge of the image forming apparatus to be fabricated; and fabricating the image forming apparatus based on a result of the designing.

56. A method of manufacturing an image forming apparatus that forms an image onto a recording medium, the method comprising:

designing the image forming apparatus so that a discomfort index S calculated from an equation $$S=A\times(\text{loudness value})+B\times(\text{sharpness value})+C\times(\text{tonality value})+D\times(\text{impulsiveness value})+E$$

where A=0.2347697, B=0.3847411, C=2.6283418, D=1.5681529, and E=−3.790295483, using loudness, sharpness, tonality, and impulsiveness of a psycho-acoustic parameter obtained from a sound generated from the image forming apparatus when forming an image onto the recording medium satisfies an inequality $$S \leq 0.532 \ln(v) - 2.8381$$

where $62.5 \leq v \leq 185$, ln indicates natural log, and v is a speed of forming an image onto the recording medium in millimeters per second, wherein the sound is collected at a listening position approximately one meter from an edge of the image forming apparatus to be fabricated; and manufacturing the image forming apparatus based on a result of the designing.

57. A method of modifying an image forming apparatus that forms an image onto a recording medium, the method comprising:

modifying the image forming apparatus so that a discomfort index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S 0.5664 \text{Ln}(\text{ppm}) - 2.1364$$

where $14 \leq \text{ppm} \leq 38$, Ln indicates natural log, and ppm is an output number of the recording medium per minute with A4 size in horizontal direction, wherein the sound is collected at a listening position approximately one meter from an edge of the image forming apparatus to be modified.

58. A method of modifying an image forming apparatus that forms an image onto a recording medium, the method comprising:

modifying the image forming apparatus so that a discomfort index S calculated from an equation $$S=A\times(\text{loudness value})+B\times(\text{sharpness value})+C\times(\text{tonality value})+D\times(\text{impulsiveness value})+E$$

where A=0.2347697, B=0.3847411, C=2.6283418, D=1.5681529, and E=−3.790295483, using loudness, sharpness, tonality, and impulsiveness of a psycho-acoustic parameter obtained from a sound generated from the image forming apparatus when forming an image onto the recording medium satisfies an inequality $$S 0.5664 \text{Ln}(\text{ppm}) - 2.1364$$

where $14 \leq \text{ppm} \leq 38$, Ln indicates natural log, and ppm is an output number of the recording medium per minute with A4 size in horizontal direction, wherein the sound is collected at a listening position approximately one meter from an edge of the image forming apparatus to be modified.

59. A method of modifying an image forming apparatus that forms an image onto a recording medium, the method comprising:

modifying the image forming apparatus so that an a discomfort index S calculated from an equation $$S=A\times(\text{loudness value})+B\times(\text{sharpness value})+C\times(\text{tonality value})+D\times(\text{impulsiveness value})+E$$

where $0.213845 \leq A \leq 0.255694$, $0.325852 \leq B \leq 0.443631$, $2.049496 \leq C \leq 3.207187$, $1.427895 \leq D \leq 1.708411$, and $-4.224266 \leq E \leq -3.356324$, using loudness, sharpness, tonality, and impulsiveness of a psycho-acoustic parameter obtained from a sound generated from the image forming apparatus when forming an image onto the recording medium satisfies an inequality $$S 0.532 \ln(v) - 2.8381$$

where 62.5v185, In indicates natural log, and v is a speed of forming an image onto the recording medium in millimeters per second, wherein the sound is collected at a listening position approximately one meter from an edge of the image forming apparatus to be modified.

60. A method of modifying an image forming apparatus that forms an image onto a recording medium, the method comprising:

modifying the image forming apparatus so that a discomfort index S calculated from an equation $$S=A(\text{loudness value})+B\times(\text{sharpness value})+C\times(\text{tonality value})+D\times(\text{impulsiveness value})+E$$

where A=0.2347697, B=0.3847411, C2.6283418, D=1.5681529, and E=−3.790295483, using loudness, sharpness, tonality, and impulsiveness of a psycho-acoustic parameter obtained from a sound generated from the image forming apparatus when forming an image onto the recording medium satisfies an inequality $$S \leq 0.532\ln(v)-2.8381$$

where $62.5 \leq v \leq 185$, In indicates natural log, and v is a speed of forming an image onto the recording medium in millimeters per second, wherein the sound is collected at a listening position approximately one meter from an edge of the image forming apparatus to be modified.

61. A method of evaluating sound generated from an image forming apparatus when forming an image onto a recording medium, the method comprising:

evaluating a plurality of kinds of the sound based on a pair comparison method;

performing a multiple linear regression analysis using a difference between scores of the evaluation as a target variable and a difference between psycho-acoustic parameter values as an explanatory variable;

deriving an equation concerning the difference between scores of sound quality from a result of the analysis, as follows $$\alpha i - \alpha j = \sum_{l=1}^{L} b_l(x_{li} - x_{lj})$$

where αn is subjective value with respect to discomfort of the sound where n=1,2, . . . i, . . . j, . . .,n, $b_i$ is a regression coefficient, $x_{1i}$ and $x_{1j}$ are Psycho-acoustic parameter values of two sounds to be compared where i=1,2,3 . . ., n and l=1,2,3 . . ., L;

substituting an average of the psycho-acoustic parameter values used to derive the equation, into the equation;
defining the discomfort of the sound when all the parameter values are average values as zero;
deriving a sound quality evaluation equation to estimate a score of the discomfort of the sound; and
evaluating the sound quality using the sound quality evaluation equation derived.

62. A method of manufacturing an image forming apparatus that forms an image onto a recording medium, the method comprising:

evaluating a plurality of kinds of the sound based on a pair comparison method;
performing a multiple linear regression analysis using a difference between scores of the evaluation as a target variable and a difference between psycho-acoustic parameter values as an explanatory variable;
deriving an equation concerning the difference between scores of sound quality from a result of the analysis, as follows $$\alpha i - \alpha j = \sum_{l=1}^{L} b_l(x_{li} - x_{lj})$$

where αn is subjective value with respect to discomfort of the sound where n=1,2, . . . i, . . . j, . . ., n, $b_i$ is a regression coefficient, $x_{1i}$ and $x_{1j}$ are Psycho-acoustic parameter values of two sounds to be compared where i=1,2,3 . . ., n and l=1,2,3 . . ., L;

substituting an average of the psycho-acoustic parameter values used to derive the equation, into the equation;
defining the discomfort of the sound when all the parameter values are average values as zero;
deriving a sound quality evaluation equation to estimate a score of the discomfort of the sound;
evaluating the sound quality using the sound quality evaluation equation derived;
designing each unit of the image forming apparatus so that a result of the evaluating satisfies a predetermined condition; and
manufacturing the image forming apparatus based on a result of the designing.

63. A method of modifying an image forming apparatus that forms an image onto a recording medium, the method comprising:

evaluating a plurality of kinds of the sound based on a pair comparison method;
performing a multiple linear regression analysis using a difference between scores of the evaluation as a target variable and a difference between psycho-acoustic parameter values as an explanatory variable;
deriving an equation concerning the difference between scores of sound quality from a result of the analysis, as follows $$\alpha i - \alpha j = \sum_{l=1}^{L} b_l(x_{li} - x_{lj})$$

where αn is subjective value with respect to discomfort of the sound where n1,2, . . . i, . . . j, . . ., n, $b_i$ is a regression coefficient, $x_{1i}$, and $x_{1j}$ are Psycho-acoustic parameter values of two sounds to be compared where i=1,2,3 . . ., n and l=1,2,3 . . ., L;

substituting an average of the psycho-acoustic parameter values used to derive the equation, into the equation;
defining the discomfort of the sound when all the parameter values are average values as zero;
deriving a sound quality evaluation equation to estimate a score of the discomfort of the sound;
evaluating the sound quality of sound generated from the image forming apparatus to be modified using the sound quality evaluation equation derived; and
modifying corresponding units of the image forming apparatus to be modified based on a result of the evaluating.

64. An image forming apparatus that forms an image onto a recording medium, wherein
a discomfort probability P calculated from an equation $$P=1/(1+\exp(-z))$$

where $z=A\times(\text{loudness value})+B\times(\text{sharpness value})+C\times(\text{tonality value})+D\times(\text{impulsiveness value})+E$ where $0.76545285 \leq A \leq 0.84940259$,
$1.27685159 \leq B \leq 1.48461447$,
$8.11323413 \leq C \leq 9.98398583$,
$5.30484579 \leq D \leq 5.87837423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P 0.3383 Ln(ppm) - 0.8103$$

where $14 \leq ppm \leq 38$ and ppm is an output number of the recording medium per minute with A4 size in horizontal direction, wherein the sound is collected at a listening position approximately one meter from an edge of the image forming apparatus.

65. The image forming apparatus according to claim 64, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the probability P satisfies the inequality in any one of the operation modes.

66. The image forming apparatus according to claim 64, wherein
the listening position is based on the International Organization for Standardization 7779, and
the probability P obtained from a sound collected from at least front direction of the image forming apparatus satisfies the inequality.

67. The image forming apparatus according to claim 64, wherein
the listening position is based on the International Organization for Standardization 7779, and
an average of the probability P's obtained from sounds collected from front, rear, left, and right directions of the apparatus satisfies the condition.

68. The image forming apparatus according to claim 64, wherein
the listening position is based on the International Organization for Standardization 7779, and
the probability P obtained from a sound collected from at least one direction among front, rear, left, and right directions of the image forming apparatus satisfies the inequality.

69. The image forming apparatus according to claim 64, wherein
the listening position is based on the International Organization for Standardization 7779, and
the probability P obtained from a sound collected from each of front, rear, left, and right directions of the image forming apparatus satisfies the inequality.

70. The image forming apparatus according to claim 64, comprising:
a decreasing unit that decreases the sound generated from the image forming apparatus when forming an image onto the recording medium.

71. The image forming apparatus according to claim 70, further comprising:
a stepping motor that drives predetermined parts of the image forming apparatus when forming an image onto the recording medium; and
a bracket member that holds the stepping motor, wherein the decreasing unit includes an elastic material disposed between the stepping motor and the bracket member.

72. The image forming apparatus according to claim 70, further comprising:
a stepping motor that drives predetermined parts of the image forming apparatus when forming an image onto the recording medium, wherein
the decreasing unit includes a drive control unit that drives the stepping motor in micro-step.

73. The image forming apparatus according to claim 70, further comprising:
a motor that drives predetermined parts of the image forming apparatus when forming an image onto the recording medium, wherein
the decreasing unit includes a Helmholtz resonator that is disposed near the motor.

74. The image forming apparatus according to claim 70, further comprising:
an image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

75. The image forming apparatus according to claim 64, comprising:
a guide member including a flexible sheet that guides the recording medium along a predetermined feeding path, wherein
an edge of the guide member is a bent portion of the flexible sheet, wherein the edge is in contact with the recording medium fed.

76. The image forming apparatus according to claim 70, wherein a toner used to form an image onto the recording medium contains wax.

77. An image forming apparatus that forms an image onto a recording medium, wherein
a discomfort probability P calculated from an equation $$P 1/(1+exp(-z 35\ 2\sigma))$$

where $z = A \times$ (loudness value) $+ B \times$ (sharpness value) $+ C \times$ (tonality value) $+ D \times$ (impulsiveness value) $+ E$ where $A=0.80742768$, $B=1.38073296$, $C=9.04860954$, $D 5.59160971$, and $E-13.28811895$, and a standard deviation $\sigma$ is $0.721307$, using loudness, sharpness, tonality, and impulsiveness of a psycho-acoustic parameter obtained from a sound generated from the image forming apparatus when forming an image onto the recording medium satisfies an inequality $$P \leq 0.3383 Ln(ppm) - 0.8103$$

where $14 \leq ppm \leq 38$, and ppm is an output number of the recording medium per minute with A4 size in horizontal direction, wherein the sound is collected at a listening position approximately one meter from an edge of the image forming apparatus.

78. The image forming apparatus according to claim 77, comprising:
a control unit that controls the image forming apparatus, wherein
the image forming apparatus has a plurality of operation modes,
the control unit selects one from the operation modes, and controls each unit of the image forming apparatus to form an image onto the recording medium, and the probability P satisfies the inequality in any one of the operation modes.

79. The image forming apparatus according to claim 77, wherein
the listening position is based on the International Organization for Standardization 7779, and
the probability P obtained from a sound collected from at least front direction of the image forming apparatus satisfies the inequality.

80. The image forming apparatus according to claim 77, wherein
the listening position is based on the International Organization for Standardization 7779, and
an average of the probability P's obtained from sounds collected from front, rear, left, and right directions of the apparatus satisfies the condition.

81. The image forming apparatus according to claim 77, wherein
the listening position is based on the International Organization for Standardization 7779, and
the probability P obtained from a sound collected from at least one direction among front, rear, left, and right directions of the image forming apparatus satisfies the inequality.

82. The image forming apparatus according to claim 77, wherein
the listening position is based on the International Organization for Standardization 7779, and
the probability P obtained from a sound collected from each of front, rear, left, and right directions of the image forming apparatus satisfies the inequality.

83. The image forming apparatus according to claim 77, comprising:
a decreasing unit that decreases the sound generated from the image forming apparatus when forming an image onto the recording medium.

84. The image forming apparatus according to claim 83, further comprising:
a stepping motor that drives predetermined parts of the image forming apparatus when forming an image onto the recording medium; and
a bracket member that holds the stepping motor, wherein the decreasing unit includes an elastic material disposed between the stepping motor and the bracket member.

85. The image forming apparatus according to claim 83, further comprising:
a stepping motor that drives predetermined parts of the image forming apparatus when forming an image onto the recording medium, wherein
the decreasing unit includes a drive control unit that drives the stepping motor in micro-step.

86. The image forming apparatus according to claim 83, further comprising:
a motor that drives predetermined parts of the image forming apparatus when forming an image onto the recording medium, wherein
the decreasing unit includes a Helmholtz resonator that is disposed near the motor.

87. The image forming apparatus according to claim 83, further comprising:
an image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

88. The image forming apparatus according to claim 77, comprising:
a guide member including a flexible sheet that guides the recording medium along a predetermined feeding path, wherein
an edge of the guide member is a bent portion of the flexible sheet, wherein the edge is in contact with the recording medium fed.

89. The image forming apparatus according to claim 83, wherein a toner used to form an image onto the recording medium contains wax.

90. An image forming apparatus that forms an image onto a recording medium, wherein
a discomfort probability P calculated from an equation $$P=1/(1+\exp(-z))$$

where $z=A\times$(loudness value)$+B\times$(sharpness value)$+C\times$(tonality value)$+D\times$(impulsiveness value)$+E$ where $A=0.80742768$, $B=1.38073296$, $C=9.04860954$, $D=5.59160971$, and $E=-13.28811895$, using loudness, sharpness, tonality, and impulsiveness of a psycho-acoustic parameter obtained from a sound generated from the image forming apparatus when forming an image onto the recording medium satisfies an inequality $$P \leq 0.3383 \mathrm{Ln}(\mathrm{ppm})-0.8103$$

where $14 \leq \mathrm{ppm} \leq 38$, and ppm is an output number of the recording medium per minute with A4 size in horizontal direction, wherein the sound is collected at a listening position approximately one meter from an edge of the image forming apparatus.

91. The image forming apparatus according to claim 90, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the probability P satisfies the inequality in any one of the operation modes.

92. The image forming apparatus according to claim 90, wherein
the listening position is based on the International Organization for Standardization 7779, and
the probability P obtained from a sound collected from at least front direction of the image forming apparatus satisfies the inequality.

93. The image forming apparatus according to claim 90, wherein
the listening position is based on the International Organization for Standardization 7779, and
an average of the probability P's obtained from sounds collected from front, rear, left, and right directions of the apparatus satisfies the condition.

94. The image forming apparatus according to claim 90, wherein
the listening position is based on the International Organization for Standardization 7779, and
the probability P obtained from a sound collected from at least one direction among front, rear, left, and right directions of the image forming apparatus satisfies the inequality.

95. The image forming apparatus according to claim 90, wherein
the listening position is based on the International Organization for Standardization 7779, and
the probability P obtained from a sound collected from each of front, rear, left, and right directions of the image forming apparatus satisfies the inequality.

96. The image forming apparatus according to claim 90, comprising:
a decreasing unit that decreases the sound generated from the image forming apparatus when forming an image onto the recording medium.

97. The image forming apparatus according to claim 96, further comprising:
a stepping motor that drives predetermined parts of the image forming apparatus when forming an image onto the recording medium; and
a bracket member that holds the stepping motor, wherein the decreasing unit includes an elastic material disposed between the stepping motor and the bracket member.

98. The image forming apparatus according to claim 96, further comprising:
a stepping motor that drives predetermined parts of the image forming apparatus when forming an image onto the recording medium, wherein
the decreasing unit includes a drive control unit that drives the stepping motor in micro-step.

99. The image forming apparatus according to claim 96, further comprising:
a motor that drives predetermined parts of the image forming apparatus when forming an image onto the recording medium, wherein
the decreasing unit includes a Helmholtz resonator that is disposed near the motor.

100. The image forming apparatus according to claim 96, further comprising:
an image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

101. The image forming apparatus according to claim 90, comprising:
a guide member including a flexible sheet that guides the recording medium along a predetermined feeding path, wherein
an edge of the guide member is a bent portion of the flexible sheet, wherein the edge is in contact with the recording medium fed.

102. The image forming apparatus according to claim 96, wherein
a toner used to form an image onto the recording medium contains wax.

103. An image forming apparatus that forms an image onto a recording medium, wherein
a discomfort probability P calculated from an equation $$P=1/(1+\exp(-z))$$

where $z=A\times(\text{loudness value})+B\times(\text{sharpness value})+C\times(\text{tonality value})+D\times(\text{impulsiveness value})+E$ where $0.76545285 \leq A \leq 0.84940259$,
$1.27685159 \leq B \leq 1.48461447$,
$8.11323413 \leq C \leq 9.98398583$,
$5.30484579 \leq D \leq 5.87837423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3201\text{Ln}(v)-1/2402$$

where $62.5 \leq v \leq 185$, and v is a speed of forming an image onto the recording medium in millimeters per second, wherein the sound is collected at a listening position approximately one meter from an edge of the image forming apparatus.

104. The image forming apparatus according to claim 103, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the probability P satisfies the inequality in any one of the operation modes.

105. The image forming apparatus according to claim 103, wherein
the listening position is based on the International Organization for Standardization 7779, and
the probability P obtained from a sound collected from at least front direction of the image forming apparatus satisfies the inequality.

106. The image forming apparatus according to claim 103, wherein
the listening position is based on the International Organization for Standardization 7779, and
an average of the probability P's obtained from sounds collected from front, rear, left, and right directions of the apparatus satisfies the condition.

107. The image forming apparatus according to claim 103, wherein
the listening position is based on the International Organization for Standardization 7779, and
the probability P obtained from a sound collected from at least one direction among front, rear, left, and right directions of the image forming apparatus satisfies the inequality.

108. The image forming apparatus according to claim 103, wherein
the listening position is based on the International Organization for Standardization 7779, and
the probability P obtained from a sound collected from each of front, rear, left, and
right directions of the image forming apparatus satisfies the inequality.

109. The image forming apparatus according to claim 103, comprising:
a decreasing unit that decreases the sound generated from the image forming apparatus when forming an image onto the recording medium.

110. The image forming apparatus according to claim 109, further comprising:
a stepping motor that drives predetermined parts of the image forming apparatus when forming an image onto the recording medium; and
a bracket member that holds the stepping motor, wherein the decreasing unit includes an elastic material disposed between the stepping motor and the bracket member.

111. The image forming apparatus according to claim 109, further comprising:
a stepping motor that drives predetermined parts of the image forming apparatus when forming an image onto the recording medium, wherein
the decreasing unit includes a drive control unit that drives the stepping motor in micro-step.

112. The image forming apparatus according to claim 109, further comprising:
a motor that drives predetermined parts of the image forming apparatus when forming an image onto the recording medium, wherein
the decreasing unit includes a Helmholtz resonator that is disposed near the motor.

113. The image forming apparatus according to claim 109, further comprising:
a image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

114. The image forming apparatus according to claim 103, comprising:
a guide member including a flexible sheet that guides the recording medium along a predetermined feeding path, wherein
an edge of the guide member is a bent portion of the flexible sheet, wherein the edge is in contact with the recording medium fed.

115. The image forming apparatus according to claim 109, wherein
a toner used to form an image onto the recording medium contains wax.

116. An image forming apparatus that forms an image onto a recording medium, wherein
a discomfort probability P calculated from an equation $P=1/(1+\exp(-z\pm 2\sigma))$ where $z=A\times$(loudness value)$+B\times$(sharpness value)$+C\times$(tonality value)$+D\times$(impulsiveness value)$+E$ where A=0.80742768, B=1.38073296, C=9.04860954, D=5.59160971, and E=−13.28811895, and a standard deviation σ is 0.721307, using loudness, sharpness, tonality, and impulsiveness of a psycho-acoustic parameter obtained from a sound generated from the image forming apparatus when forming an image onto the recording medium satisfies an inequality $P \leq 0.3202 \text{Ln}(v) - 1.2402$ where $62.5 \leq v \leq 185$, and v is a speed of forming an image onto the recording medium in millimeters per second, wherein the sound is collected at a listening position approximately one meter from an edge of the image forming apparatus.

117. The image forming apparatus according to claim 116, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the probability P satisfies the inequality in any one of the operation modes.

118. The image forming apparatus according to claim 116, wherein
the listening position is based on the International Organization for Standardization 7779, and
the probability P obtained from a sound collected from at least front direction of the image forming apparatus satisfies the inequality.

119. The image forming apparatus according to claim 116, wherein
the listening position is based on the International Organization for Standardization 7779, and
an average of the probability P's obtained from sounds collected from front, rear, left, and right directions of the apparatus satisfies the condition.

120. The image forming apparatus according to claim 116, wherein
the listening position is based on the International Organization for Standardization 7779, and
the probability P obtained from a sound collected from at least one direction among front, rear, left, and right directions of the image forming apparatus satisfies the inequality.

121. The image forming apparatus according to claim 116, wherein
the listening position is based on the International Organization for Standardization 7779, and
the probability P obtained from a sound collected from each of front, rear, left, and
right directions of the image forming apparatus satisfies the inequality.

122. The image forming apparatus according to claim 116, comprising:
a decreasing unit that decreases the sound generated from the image forming apparatus when forming an image onto the recording medium.

123. The image forming apparatus according to claim 122, further comprising:
a stepping motor that drives predetermined parts of the image forming apparatus when forming an image onto the recording medium; and
a bracket member that holds the stepping motor, wherein
the decreasing unit includes an elastic material disposed between the stepping motor and the bracket member.

124. The image forming apparatus according to claim 122, further comprising:
a stepping motor that drives predetermined parts of the image forming apparatus when forming an image onto the recording medium, wherein
the decreasing unit includes a drive control unit that drives the stepping motor in micro-step.

125. The image forming apparatus according to claim 122, further comprising:
a motor that drives predetermined parts of the image forming apparatus when forming an image onto the recording medium, wherein
the decreasing unit includes a Helmholtz resonator that is disposed near the motor.

126. The image forming apparatus according to claim 122, further comprising:
an image carrier of a cylindrical shape having a hollow portion; and
a charging unit that charges a surface of the image carrier, wherein the decreasing unit is disposed in the hollow portion of the image carrier, and includes a damping material that suppresses vibration of the image carrier.

127. The image forming apparatus according to claim 116, comprising:
a guide member including a flexible sheet that guides the recording medium along a predetermined feeding path, wherein
an edge of the guide member is a bent portion of the flexible sheet, wherein the edge is in contact with the recording medium fed.

128. The image forming apparatus according to claim 122, wherein a toner used to form an image onto the recording medium contains wax.

129. An image forming apparatus that forms an image onto a recording medium, wherein
a discomfort probability P calculated from an equation $$P=1/(1+\exp(-z))$$

where $z=A\times$(loudness value)$+B\times$(sharpness value)$+C\times$(tonality value)$+D\times$(impulsiveness value)$+E$ where A=0.80742768, B=1.38073296, C=9.04860954, D=5.59160971, and E=−13.28811895, using loudness, sharpness, tonality, and impulsiveness of a psycho-acoustic parameter obtained from a sound generated from the image forming apparatus when forming an image onto the recording medium satisfies an inequality $$P \leq 0.3201 \mathrm{Ln}(v) - 1.2402,$$

where $62.5 \leq v \leq 185$, and v is a speed of forming an image onto the recording medium in millimeters per second, wherein the sound is
collected at a listening position approximately one meter from an edge of the image forming apparatus.

130. The image forming apparatus according to claim 129, comprising:
a control unit that controls the image forming apparatus, wherein
the image forming apparatus has a plurality of operation modes,
the control unit selects one from the operation modes, and controls each unit of the image forming apparatus to form an image onto the recording medium, and
the probability P satisfies the inequality in any one of the operation modes.

131. The image forming apparatus according to claim 129, wherein
the listening position is based on the International Organization for Standardization 7779, and
the probability P obtained from a sound collected from at least front direction of the image forming apparatus satisfies the inequality.

132. The image forming apparatus according to claim 129, wherein
the listening position is based on the International Organization for Standardization 7779, and
an average of the probability P's obtained from sounds collected from front, rear, left, and right directions of the apparatus satisfies the condition.

133. The image forming apparatus according to claim 129, wherein
the listening position is based on the International Organization for Standardization 7779, and
the probability P obtained from a sound collected from at least one direction among front, rear, left, and right directions of the image forming apparatus satisfies the inequality.

134. The image forming apparatus according to claim 129, wherein
the listening position is based on the International Organization for Standardization 7779, and
the probability P obtained from a sound collected from each of front, rear, left, and right directions of the image forming apparatus satisfies the inequality.

135. The image forming apparatus according to claim 129, comprising:
a decreasing unit that decreases the sound generated from the image forming apparatus when forming an image onto the recording medium.

136. The image forming apparatus according to claim 135, further comprising:
a stepping motor that drives predetermined parts of the image forming apparatus when forming an image onto the recording medium; and
a bracket member that holds the stepping motor, wherein the decreasing unit includes an elastic material disposed between the stepping motor and the bracket member.

137. The image forming apparatus according to claim 135, further comprising:
a stepping motor that drives predetermined parts of the image forming apparatus when forming an image onto the recording medium, wherein
the decreasing unit includes a drive control unit that drives the stepping motor in micro-step.

138. The image forming apparatus according to claim 135, further comprising:
a motor that drives predetermined parts of the image forming apparatus when forming an image onto the recording medium, wherein
the decreasing unit includes a Helmholtz resonator that is disposed near the motor.

139. The image forming apparatus according to claim 135, further comprising:
a image carrier of a cylindrical shape having a hollow portion; and
a charging unit that charges a surface of the image carrier, wherein
the decreasing unit is disposed in the hollow portion of the image carrier, and includes a damping material that suppresses vibration of the image carrier.

140. The image forming apparatus according to claim 129, comprising:
a guide member including a flexible sheet that guides the recording medium along a predetermined feeding path, wherein
an edge of the guide member is a bent portion of the flexible sheet, wherein the edge is in contact with the recording medium fed.

141. The image forming apparatus according to claim 135, wherein a toner used to form an image onto the recording medium contains wax.

142. A method of manufacturing an image forming apparatus that forms an image onto a recording medium, the method comprising:
designing the image forming apparatus so that a discomfort probability P calculated from an equation $$P=1/(1+\exp(-z))$$

where $z=A\times$(loudness value)$+B\times$(sharpness value)$+C\times$(tonality value)$+D\times$(impulsiveness value)$+E$ where $0.76545285 \leq A \leq 0.84940259$,
$1.27685159 \leq B \leq 1.48461447$,
$8.11323413 \leq C \leq 9.98398583$,
$5.30484579 \leq D \leq 5.87837423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3383 \mathrm{Ln}(\mathrm{ppm}) - 0.8103,$$

where $14 \leq \mathrm{ppm} \leq 38$ and ppm is an output number of the recording medium per minute with A4 size in horizontal direction, wherein the sound is collected at a listening position approximately one meter from an edge of the image forming apparatus to be fabricated; and fabricating the image forming apparatus based on a result of the designing.

143. A method of manufacturing an image forming apparatus that forms an image onto a recording medium, the method comprising:

designing the image forming apparatus so that a discomfort probability P calculated from an equation $$P = 1/(1 + \exp(-z \pm 2\sigma))$$

where $z = A \times (\text{loudness value}) + B \times (\text{sharpness value}) + C \times (\text{tonality value}) + D \times (\text{impulsiveness value}) + E$ where $A = 0.80742768$, $B = 1.38073296$, $C = 9.04860954$, $D = 5.59160971$, and $E = -13.28811895$, and a standard deviation $\sigma$ is $0.721307$, using loudness, sharpness, tonality, and impulsiveness of a psycho-acoustic parameter obtained from a sound generated from the image forming apparatus when forming an image onto the recording medium satisfies an inequality $$P \leq 0.3383 \mathrm{Ln}(\mathrm{ppm}) - 0.8103,$$

where $14 \leq \mathrm{ppm} \leq 38$ and ppm is an output number of the recording medium per minute with A4 size in horizontal direction, wherein the sound is collected at a listening position approximately one meter from an edge of the image forming apparatus to be fabricated; and fabricating the image forming apparatus based on a result of the designing.

144. A method of manufacturing an image forming apparatus that forms an image onto a recording medium, the method comprising:

designing the image forming apparatus so that a discomfort probability P calculated from an equation $$P = 1/(1 = \exp(-z))$$

where $z = A \times (\text{loudness value}) + B \times (\text{sharpness value}) + C \times (\text{tonality value}) + D \times (\text{impulsiveness value}) + E$ where $A = 0.80742768$, $B = 1.38073296$, $C = 9.04860954$, $D = 5.59160971$, and $E = -13.28811895$, using loudness, sharpness, tonality, and impulsiveness of a psycho-acoustic parameter obtained from a sound generated from the image forming apparatus when forming an image onto the recording medium satisfies an inequality $$P \leq 0.3383 \mathrm{Ln}(\mathrm{ppm}) - 0.8103,$$

where $14 \leq \mathrm{ppm} \leq 38$, and ppm is an output number of the recording medium per minute with A4 size in horizontal direction, wherein the sound is collected at a listening position approximately one meter from an edge of the image forming apparatus to be fabricated; and fabricating the image forming apparatus based on a result of the designing.

145. A method of manufacturing an image forming apparatus that forms an image onto a recording medium, the method comprising:

designing the image forming apparatus so that a discomfort probability P calculated from an equation $$P = 1/(1 + \exp(-z))$$

where $z = A \times (\text{loudness value}) + B \times (\text{sharpness value}) + C \times (\text{tonality value}) + D \times (\text{impulsiveness value}) + E$ where $0.76545285 \leq A \leq 0.84940259$,
$1.27685159 \leq B \leq 1.48461447$,
$8.11323413 \leq C \leq 9.98398583$,
$5.30484579 \leq D \leq 5.87837423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3201 \mathrm{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be fabricated; and fabricating the image forming apparatus based on a result of the designing.

146. A method of manufacturing an image forming apparatus that forms an image onto a recording medium, the method comprising:

designing the image forming apparatus so that a discomfort probability P calculated from an equation $$P = 1/(1 + \exp(-z \pm 2\sigma))$$

where $z = A \times (\text{loudness value}) + B \times (\text{sharpness value}) + C \times (\text{tonality value}) + D \times (\text{impulsiveness value}) + E$ where $A = 0.80742768$, $B1.38073296$, $C9.04860954$, $D5.59160971$, and $E = -13.28811895$, and a standard deviation $\sigma$ is $0.72\,1307$, using loudness, sharpness, tonality, and impulsiveness of a psycho-acoustic parameter obtained from a sound generated from the image forming apparatus when forming an image onto the recording medium satisfies an inequality $$P \leq 0.3201 \mathrm{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be fabricated; and fabricating the image forming apparatus based on a result of the designing.

147. A method of manufacturing an image forming apparatus that forms an image onto a recording medium, the method comprising:

designing the image forming apparatus so that a discomfort probability P calculated from an equation $$P = 1/(1 + \exp(-z))$$

where $z = A \times (\text{loudness value}) + B \times (\text{sharpness value}) + C \times (\text{tonality value}) + D \times (\text{impulsiveness value}) + E$ where $A = 0.80742768$, $B = 1.38073296$, $C = 9.04860954$, $D = 5.59160971$, and $E = -13.28811895$, using loudness, sharpness, tonality, and impulsiveness of a psycho-acoustic parameter obtained from a sound generated from the image forming apparatus when forming an image onto the recording medium satisfies an inequality $$P \leq 0.3201\text{Ln}(mm/s) - 1.2402,$$

where $62.5 \leq v \leq 185$, and v is a speed of forming an image onto the recording medium in millimeters per second, wherein the sound is collected at a listening position approximately one meter from an edge of the image forming apparatus to be fabricated; and fabricating the image forming apparatus based on a result of the designing.

148. A method of modifying an image forming apparatus that forms an image onto a recording medium, the method comprising:

modifying the image forming apparatus so that a discomfort probability P calculated from an equation $$P = 1/(1 + \exp(-z))$$

where $z = A \times (\text{loudness value}) + B \times (\text{sharpness value}) + C \times (\text{tonality value}) + D \times (\text{impulsiveness value}) + E$ where $A = 0.76545285 \leq A \leq 0.84940259$, $1.27685159 \leq B \leq 1.48461447$, $8.11323413 \leq C \leq 9.98398583$, $5.30484579 \leq D \leq 5.87837423$, $-14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3383\text{Ln}(\text{ppm}) - 0.8103$$

where $14 \leq \text{ppm} \leq 38$, and ppm is an output number of the recording medium per minute with A4 size in horizontal direction, wherein the sound is collected at a listening position approximately one meter from an edge of the image forming apparatus to be modified.

149. A method of modifying an image forming apparatus that forms an image onto a recording medium, the method comprising:

modifying the image forming apparatus so that a discomfort probability P calculated from an equation $$P = 1/(1 + \exp(-z \pm 2\sigma))$$

where $z = A \times (\text{loudness value}) + B \times (\text{sharpness value}) + C \times (\text{tonality value}) + D \times (\text{impulsiveness value}) + E$ where $A = 0.80742768$, $B = 1.38073296$, $C = 9.04860954$, $D = 5.59160971$, and $E = -13.28811895$, and a standard deviation $\sigma$ is 0.72 1307, using loudness, sharpness, tonality, and impulsiveness of a psycho-acoustic parameter obtained from a sound generated from the image forming apparatus when forming an image onto the recording medium satisfies an inequality $$P \leq 0.3383\text{Ln}(\text{ppm}) - 0.8103,$$

where $14 \leq \text{ppm} \leq 38$ and ppm is an output number of the recording medium per minute with A4 size in horizontal direction, wherein the sound is collected at a listening position approximately one meter from an edge of the image forming apparatus to be modified.

150. A method of modifying an image forming apparatus that forms an image onto a recording medium, the method comprising:

modifying the image forming apparatus so that a discomfort probability P calculated from an equation $$P = 1/(1 + \exp(-z))$$

where $z = A \times (\text{loudness value}) + B \times (\text{sharpness value}) + C \times (\text{tonality value}) + D \times (\text{impulsiveness value}) + E$ where $A = 0.80742768$, $B = 1.38073296$, $C = 9.04860954$, $D = 5.59160971$, and $E = -13.28811895$, using loudness, sharpness, tonality, and impulsiveness of a psycho-acoustic parameter obtained from a sound generated from the image forming apparatus when forming an image onto the recording medium satisfies an inequality $$P \leq 0.3383\text{Ln}(\text{ppm}) - 0.8301$$

where $14 \leq \text{ppm} \leq 38$, and ppm is an output number of the recording medium per minute with A=4 size in horizontal direction, wherein the sound is collected at a listening position approximately one meter from an edge of the image forming apparatus to be modified.

151. A method of modifying an image forming apparatus that forms an image onto a recording medium, the method comprising:

modifying the image forming apparatus so that a discomfort probability P calculated from an equation $$P\ 1/(1+\exp(-z))$$

where $z = A \times (\text{loudness value}) + B \times (\text{sharpness value}) + C \times (\text{tonality value}) + D \times (\text{impulsiveness value}) + E$ where $0.76545285 \leq A \leq 0.84940259$, $1.27685159 \leq B \leq 1.48461447$, $8.11323413 \leq C \leq 9$, $98398583$, $5.30484579 \leq D \leq 5.87837423 - 14.10339529 \leq E \leq -12.47284396$, using loudness, sharpness, tonality, and impulsiveness of a psycho-acoustic parameter obtained from a sound generated from the image forming apparatus when forming an image onto the recording medium satisfies an inequality $$P \leq 0.3201\text{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be modified.

152. A method of modifying an image forming apparatus that forms an image onto a recording medium, the method comprising:

modifying the image forming apparatus so that a discomfort probability P calculated from an equation $$P = 1/(1+\exp(-z \pm 2\sigma))$$

where $z = A \times (\text{loudness value}) + B \times (\text{sharpness value}) + C \times (\text{tonality value}) + D \times (\text{impulsiveness value}) + E$ where $A = 0.80742768$, $B = 1.38073296$, $C = 9.04860954$, $D = 5.59160971$, and $E = -13.28811985$, and a standard deviation $\sigma$ is 0.721307, using loudness, sharpness, tonality, and impulsiveness of a psycho-acoustic parameter obtained from a sound generated from the image forming apparatus when forming an image onto the recording medium satisfies an inequality $$P \leq 0.3201\text{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be modified.

153. A method of modifying an image forming apparatus that forms an image onto a recording medium, the method comprising:

modifying the image forming apparatus so that a discomfort probability P calculated from an equation $$P=1/(1+\exp(-z))$$

where $z=A\times$(loudness value)$+B\times$(sharpness value)$+C\times$(tonality value)$+D\times$(impulsiveness value)$+E$ where A=0.80742768, B=1.38073296, C=9.04860954, D=5.59160971, and E=−13.28811895, using loudness, sharpness, tonality, and impulsiveness of a psycho-acoustic parameter obtained from a sound generated from the image forming apparatus when forming an image onto the recording medium satisfies an inequality $$P \leq 0.3201 \mathrm{Ln}(v) - 1.2402,$$

where $62.5 \leq v \leq 185$, and v is a speed of forming an image onto the recording medium in millimeters per second, wherein the sound is collected at a listening position approximately one meter from an edge of the image forming apparatus to be modified.

154. A method of evaluating sound generated from an image forming apparatus when forming an image onto a recording medium, the method comprising:

evaluating a plurality of kinds of the sound based on a pair comparison method;

performing a logistic regression analysis using discomfort probabilities of two sounds based on the evaluating as a target variable and using a difference between psycho-acoustic parameter values as an explanatory variable;

deriving an equation concerning the discomfort probability of sound quality from a result of the analysis, as follows $$\hat{P}_{ij} = 1 \bigg/ \left\{ 1 + \exp\left[-\left(\sum_{l=1}^{L} b_l (x_{li} - x_{lj})\right)\right] \right\}$$

where $b_l$ is a regression coefficient, $x_{li}$ and $x_{lj}$ are Psycho-acoustic parameter values of two sounds to be compared where i=1,2,3 . . ., n and l=1,2,3 . . ., L;

substituting an average of the psycho-acoustic parameter values used to derive the equation, into the equation;

defining a probability P as 0.5;

deriving a sound quality evaluation equation to estimate the discomfort probability of the sound; and evaluating the sound quality using the sound quality evaluation equation derived.

155. A method of manufacturing an image forming apparatus that forms an image onto a recording medium, the method comprising:

evaluating a plurality of kinds of the sound based on a pair comparison method;

performing a logistic regression analysis using discomfort probabilities of two sounds based on the evaluating as a target variable and using a difference between psycho-acoustic parameter values as an explanatory variable;

deriving an equation concerning the discomfort probability of sound quality from a result of the analysis, as follows $$\hat{P}_{ij} = 1 \bigg/ \left\{ 1 + \exp\left[-\left(\sum_{l=1}^{L} b_l (x_{li} - x_{lj})\right)\right] \right\}$$

where $b_l$ is a regression coefficient, $x_{li}$ and $x_{lj}$ are Psycho-acoustic parameter values of two sounds to be compared where i=1,2,3 . . ., n and l=1,2,3 . . ., L;

substituting an average of the psycho-acoustic parameter values used to derive the equation, into the equation;

defining a probability P as 0.5;

deriving a sound quality evaluation equation to estimate the discomfort probability of the sound;

evaluating the sound quality using the sound quality evaluation equation derived;

designing each unit of the image forming apparatus so that a result of the evaluating satisfies a predetermined condition; and manufacturing the image forming apparatus based on a result of the designing.

156. A method of modifying an image forming apparatus that forms an image onto a recording medium, the method comprising:

evaluating a plurality of kinds of the sound based on a pair comparison method;

performing a logistic regression analysis using discomfort probabilities of two sounds based on the evaluating as a target variable and using a difference between psycho-acoustic parameter values as an explanatory variable;

deriving an equation concerning the discomfort probability of sound quality from a result of the analysis, as follows $$\hat{P}_{ij} = 1 \bigg/ \left\{ 1 + \exp\left[-\left(\sum_{l=1}^{L} b_l (x_{li} - x_{lj})\right)\right] \right\}$$

where $b_l$ is a regression coefficient, $x_{li}$ and $x_{lj}$ are Psycho-acoustic parameter values of two sounds to be compared where i=1,2,3 . . ., n and l=1,2,3 . . ., L;

substituting an average of the psycho-acoustic parameter values used to derive the equation, into the equation;

defining a probability P as 0.5;

deriving a sound quality evaluation equation to estimate the discomfort probability of the sound;

evaluating the sound quality using the sound quality evaluation equation derived; and modifying corresponding units of the image forming apparatus to be modified based on a result of the evaluating.

* * * * *